(12) United States Patent
Kunio et al.

(10) Patent No.: US 12,161,426 B2
(45) Date of Patent: Dec. 10, 2024

(54) ARTIFICIAL INTELLIGENCE COREGISTRATION AND MARKER DETECTION, INCLUDING MACHINE LEARNING AND USING RESULTS THEREOF

(71) Applicants: Canon U.S.A., Inc., Melville, NY (US); The General Hospital Corporation, Boston, MA (US)

(72) Inventors: Mie Kunio, Boston, MA (US); Markus Daniel Herrmann, Boston, MA (US); Guillermo J. Tearney, Cambridge, MA (US)

(73) Assignees: Canon U.S.A., Inc., Melville, NY (US); General Hospital Corporation, Boston, MA (US)

(*) Notice: Subject to any disclaimer, the term of this patent is extended or adjusted under 35 U.S.C. 154(b) by 244 days.

(21) Appl. No.: 17/761,561

(22) PCT Filed: Sep. 18, 2020

(86) PCT No.: PCT/US2020/051615
§ 371 (c)(1),
(2) Date: Mar. 17, 2022

(87) PCT Pub. No.: WO2021/055837
PCT Pub. Date: Mar. 25, 2021

(65) Prior Publication Data
US 2022/0346885 A1    Nov. 3, 2022

Related U.S. Application Data

(60) Provisional application No. 62/903,630, filed on Sep. 20, 2019.

(51) Int. Cl.
*A61B 34/00* (2016.01)
*A61B 6/00* (2006.01)
(Continued)

(52) U.S. Cl.
CPC ............ *A61B 34/20* (2016.02); *A61B 6/12* (2013.01); *A61B 6/463* (2013.01); *A61B 6/504* (2013.01);
(Continued)

(58) Field of Classification Search
CPC .......... A61B 34/20; A61B 6/12; A61B 6/463; A61B 6/504; A61B 6/5247;
(Continued)

(56) References Cited

U.S. PATENT DOCUMENTS

| 6,763,261 B2 | 7/2004 | Casscells, III et al. |
| 7,366,376 B2 | 4/2008 | Shishkov et al. |

(Continued)

FOREIGN PATENT DOCUMENTS

| CN | 105188550 A | 12/2015 |
| CN | 109035234 A | 12/2018 |

(Continued)

OTHER PUBLICATIONS

Sepp Hochreiter, et al., "Long Short-term Memory", Neural Computation, vol. 9, Issue 8, Nov. 1997, pp. 1735-1780 (https://dl.acm.org/doi/10.1162/neco.1997.9.8.1735).

(Continued)

*Primary Examiner* — Khai M Nguyen
(74) *Attorney, Agent, or Firm* — Canon U.S.A., Inc. I.P. Division

(57) ABSTRACT

One or more devices, systems, methods, and storage mediums using artificial intelligence application(s) using an apparatus or system that uses and/or controls one or more imaging modalities, such as, but not limited to, angiography, Optical Coherence Tomography (OCT), Multi-modality OCT, near-infrared fluorescence (NIRAF), OCT-NIRAF, etc. are provided herein. Examples of AI applications discussed herein, include, but are not limited to, using one or (Continued)

more of: AI coregistration, AI marker detection, deep or machine learning, computer vision or image recognition task(s), keypoint detection, feature extraction, model training, input data preparation techniques, input mapping to the model, post-processing, and/or interpretation of output data, one or more types of machine learning models (including, but not limited to, segmentation, regression, combining or repeating regression and/or segmentation), marker detection success rates, and/or co-registration success rates to improve or optimize marker detection and/or co-registration.

14 Claims, 34 Drawing Sheets

(51) Int. Cl.
| | | |
|---|---|---|
| A61B 6/12 | (2006.01) | |
| A61B 6/46 | (2024.01) | |
| A61B 6/50 | (2024.01) | |
| A61B 34/20 | (2016.01) | |
| G06T 7/00 | (2017.01) | |
| A61B 90/00 | (2016.01) | |

(52) U.S. Cl.
CPC .......... *A61B 6/5247* (2013.01); *G06T 7/0012* (2013.01); *A61B 2034/2051* (2016.02); *A61B 2090/3966* (2016.02); *G06T 2207/20081* (2013.01); *G06T 2207/20084* (2013.01); *G06T 2207/30004* (2013.01); *G06T 2207/30204* (2013.01)

(58) Field of Classification Search
CPC .... A61B 2034/2051; A61B 2090/3966; A61T 7/0012; G06T 2207/20081; G06T 2207/20054; G06T 2207/30004; G06T 2207/30204
See application file for complete search history.

(56) References Cited

U.S. PATENT DOCUMENTS

| | | |
|---|---|---|
| 7,843,572 B2 | 11/2010 | Tearney et al. |
| 7,872,759 B2 | 1/2011 | Tearney et al. |
| 7,889,348 B2 | 2/2011 | Tearney et al. |
| 8,289,522 B2 | 10/2012 | Tearney et al. |
| 8,676,013 B2 | 3/2014 | Bouma et al. |
| 8,928,889 B2 | 1/2015 | Tearney et al. |
| 9,087,368 B2 | 7/2015 | Tearney et al. |
| 9,119,573 B2 | 9/2015 | Lu et al. |
| 9,332,942 B2 | 5/2016 | Jaffer et al. |
| 9,351,698 B2 | 5/2016 | Dascal et al. |
| 9,557,154 B2 | 1/2017 | Tearney et al. |
| 9,770,172 B2 | 9/2017 | Sturm |
| 9,962,124 B2 | 5/2018 | Najarian et al. |
| 10,152,788 B2 | 12/2018 | Klaiman et al. |
| 10,395,366 B2 | 8/2019 | Isgum et al. |
| 10,674,985 B2 | 6/2020 | Kunio |
| 10,842,589 B2 | 11/2020 | Kunio |
| 10,952,616 B2 | 3/2021 | Watanabe |
| 11,058,385 B2 | 7/2021 | Kunio |
| 2010/0092389 A1 | 4/2010 | Jaffer |
| 2011/0292400 A1 | 12/2011 | Fleming et al. |
| 2012/0101374 A1 | 4/2012 | Tearney et al. |
| 2014/0254900 A1 | 9/2014 | Sturm |
| 2014/0270436 A1* | 9/2014 | Dascal ................ A61B 5/0073 382/130 |
| 2014/0276011 A1 | 9/2014 | Schmitt et al. |
| 2016/0180521 A1 | 6/2016 | Mountney et al. |
| 2016/0228097 A1 | 8/2016 | Jaffer et al. |
| 2017/0135584 A1 | 5/2017 | Tearney et al. |
| 2017/0308997 A1 | 10/2017 | Silver |
| 2018/0129896 A1 | 5/2018 | Wu et al. |
| 2018/0271614 A1 | 9/2018 | Kunio |
| 2019/0029623 A1 | 1/2019 | Kunio |
| 2019/0029624 A1* | 1/2019 | Kunio .................... A61B 90/39 |
| 2019/0099080 A1 | 4/2019 | Kunio et al. |
| 2019/0102906 A1 | 4/2019 | Kunio et al. |
| 2019/0110753 A1* | 4/2019 | Zhang .................. A61B 3/0025 |
| 2019/0318476 A1* | 10/2019 | Isgum .................... G16H 50/50 |
| 2019/0339850 A1 | 11/2019 | Ho |
| 2019/0354882 A1 | 11/2019 | Sharma et al. |
| 2020/0226422 A1 | 7/2020 | Li et al. |
| 2020/0390323 A1 | 12/2020 | Yamada |
| 2021/0077037 A1 | 3/2021 | Kunio |
| 2022/0104786 A1 | 4/2022 | Kunio |

FOREIGN PATENT DOCUMENTS

| | | |
|---|---|---|
| CN | 109830284 A | 5/2019 |
| JP | 2017-131348 A | 8/2017 |
| JP | 2017185007 A | 10/2017 |
| JP | 2020528779 A | 10/2020 |
| WO | 2016/015052 A1 | 1/2016 |
| WO | 2016/144878 A1 | 9/2016 |
| WO | 2019/002510 A1 | 1/2019 |
| WO | 2019/023375 A2 | 1/2019 |
| WO | 2019/023382 A1 | 1/2019 |
| WO | 2020/159984 A1 | 8/2020 |

OTHER PUBLICATIONS

Ilya Sutskever, et al., "Sequence to Sequence Learning with Neural Networks", Advances in Neural Information Processing Systems 27 (NIPS 2014), Dec. 2014, pp. 1-9 (https://papers.nips.cc/paper/5346-sequence-tosequence-learning-with-neural-networks.pdf).

Olaf Ronnenberger, et al., "U-Net: Convolutional Networks for Biomedical Image Segmentation", Computer Science Department and BIOSS Centre for Biological Signalling Studies, Medical Image Computing and Computer-Assisted Intervention, MICCAI 2015, Lecture Notes in Computer Science, vol. 9351, May 18, 2015 (https://arxiv.org/pdf/1505.04597.pdf) (8 pages in PDF file).

Kaiming He, et al., "Deep Residual Learning for Image Recognition", Microsoft Research Tech report, Dec. 10, 2015 (https://arxiv.org/pdf/1512.03385.pdf) (12 pages in PDF file).

Tsung-Yi Lin, et al., "Feature Pyramid Networks for Object Detection", Facebook AI Research (FAIR), Apr. 19, 2017 (https://arxiv.org/abs/1612.03144) (10 pages in PDF file).

Simon Jégou, et al., "The One Hundred Layers Tiramisu: Fully Convolutional DenseNets for Semantic Segmentation", Montreal Institute for Learning Algorithms, IEEE Conference on Computer Vision and Pattern Recognition Workshops (CVPRW), Honolulu, HI, pp. 1175-1183, Oct. 31, 2017 (https://arxiv.org/pdf/1611.09326.pdf; doi: 10.1109/CVPRW.2017.156) (9 pages in PDF file).

Kaiming He, et al., "Mask R-CNN", Facebook AI Research (FAIR), Jan. 24, 2018 (https://arxiv.org/pdf/1703.06870.pdf) (12 pages in PDF file).

Tsung-Yi Lin, et al., "Focal Loss for Dense Object Detection", Facebook AI Research (FAIR), Feb. 2018 (https://arxiv.org/pdf/1708.02002.pdf) (10 pages in PDF file).

Au, et al., "Automated Characterization of Stenosis in Invasive Coronary Angiography Images with Convolutional Neural Networks", Yale Center for Outcomes Research and Evaluation, Yale Cardiovascular Research Group, Jul. 2018 (https://arxiv.org/abs/1807.10597) (12 pages in PDF file).

Nils Gessert, et al., "Automatic Plaque Detection in IVOCT Pullbacks Using Convolutional Neural Networks", IEEE Transactions on Medical Imaging, Aug. 2018, pp. 1-9 (https://arxiv.org/abs/1808.04187).

Ciusdel, et al., "An artificial intelligence based solution for fully automated cardiac phase and end-diastolic frame detection on coronary angiographies", Journal of the American College of Cardiology, vol. 72, Issue 13, Supplement, Sep. 2018, pp. B96-B97 (TCT 2019 abstract, https://www.sciencedirect.com/science/article/pii/S60735109718373637) (2 pages in the PDF file).

Loc Tri Vu, et al., TCT 856: "Using Artificial Intelligence to Match Culprit Lesions in Acute Coronary Syndrome With Turbulent Flow

(56) References Cited

OTHER PUBLICATIONS

Caused by Collision of Antegrade and Retrograde Coronary Flow", Presentation, TCT Abstracts Posters 2019, Sep. 2019 (23 pages in the Presentation slides of the PDF file).

Xuqing Liu, et al., TCT 242: "Detection and Classification of Coronary Bifurcation Lesions by Using Artificial Intelligence", Journal of the American College of Cardiology, vol. 74, No. 13, Supplement B, Oct. 2019, p. B241 (1 page in PDF file).

Alex Sherstinsky, "Fundamentals of Recurrent Neural Network (RNN) and Long Short-Term Memory (LSTM) Network", Elsevier Journal, Physica D: Nonlinear Phenomena, vol. 404, Mar. 2020, pp. 1-43 (https://arxiv.org/abs/1808.03314) (43 pages in PDF file).

Adit Deshpande, "A Beginner's Guide To Understanding Convolutional Neural Networks Part 2", Engineering at Forward, Jul. 2016, obtained at https://adeshpande3.github.io/A-Beginner%27s-Guide-To-Understanding-Convolutional-Neural-Networks-Part-2/ on May 24, 2022 (9 pages in PDF file).

Notification of Transmittal of the International Search Report and the Written Opinion of the ISA, and International Search Report and Written Opinion, for PCT/US2020/051615, dated Dec. 22, 2020.

Liheng Zhang, et al., "Cascade Attention Machine for Occluded Landmark Detection in 2D X-ray Angiography", 2019 IEEE Winter Conference of Applications of Computer Vision (WACV), IEEE, XP033525636, pp. 91-100, Jan. 2019 [retrieved on Mar. 4, 2019].

\* cited by examiner

Marker detection success rate = (Number of frames that the detected and the actual radiopaque marker locations are same) / (Number of total frames during the OCT pullback)

| | Method 1 | Method 2 | Method 3 |
|---|---|---|---|
| | User specifies pullback region on 1 frame. | User points out marker location on multiple frames. | User specifies pullback region on multiple frames. |
| Animal study (N=45, DICOM) | 65.1 ± 13.9 | 62.7 ± 19.6 | 69.6 ± 13.1 |
| Bern Data (N=9, DICOM) | 39.6 ± 17.9 | 58.7 ± 32.3 | 51.1 ± 22.6 |
| MGH Data (N=36, DICOM) | 40.1 ± 18.5 | 41.1 ± 28.6 | 48.2 ± 20.0 |

*All results are shown as average ± standard deviation.

FIG. 5

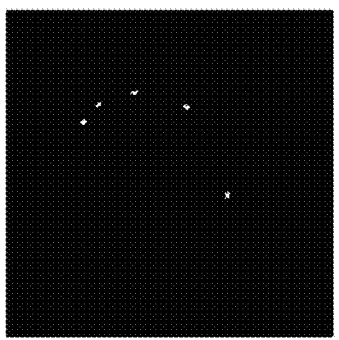
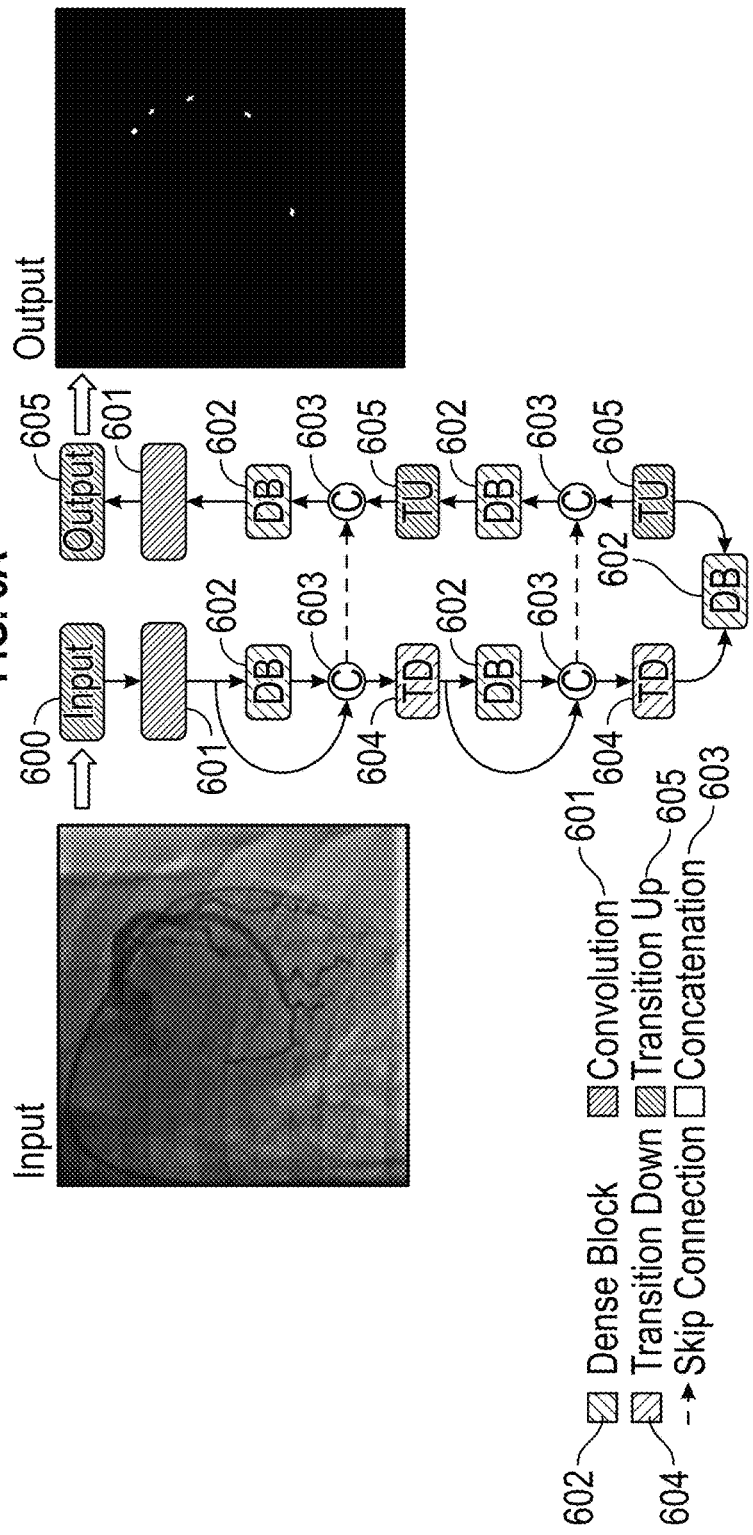
FIG. 6A
FIG. 6B

• RESULTS
SUCCESS RATE = (NUMBER OF FRAMES OF WHICH ROOT MEAN SQUARED ERROR<THRESHOLD CRITERION) / (NUMBER OF TOTAL FRAMES IN ALL PULLBACKS IN THE DATASET)
Training data
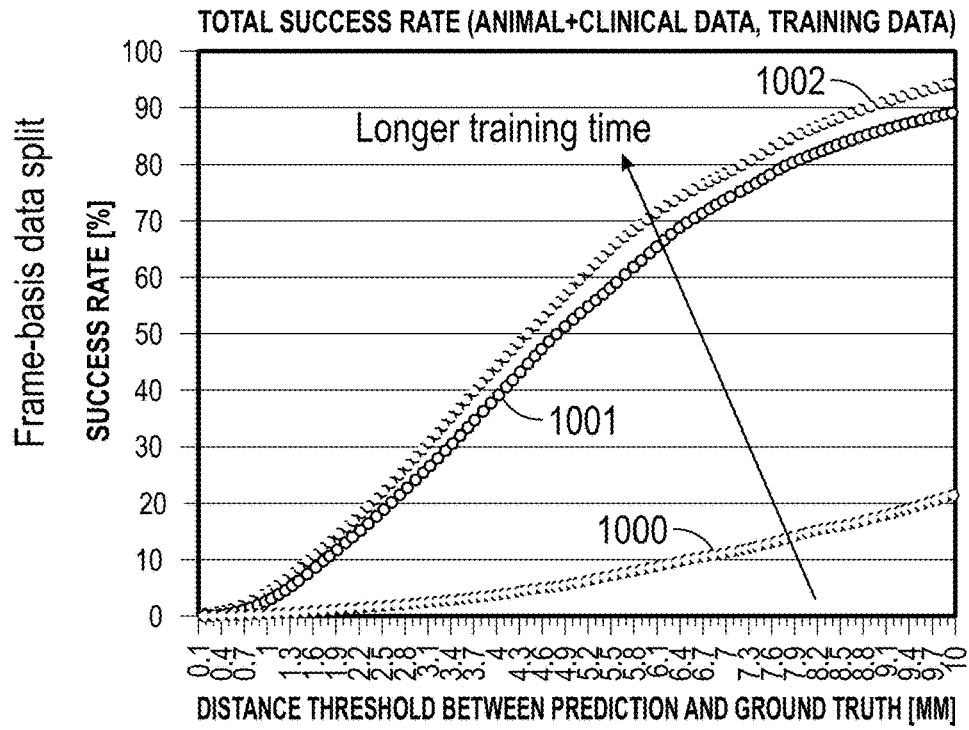
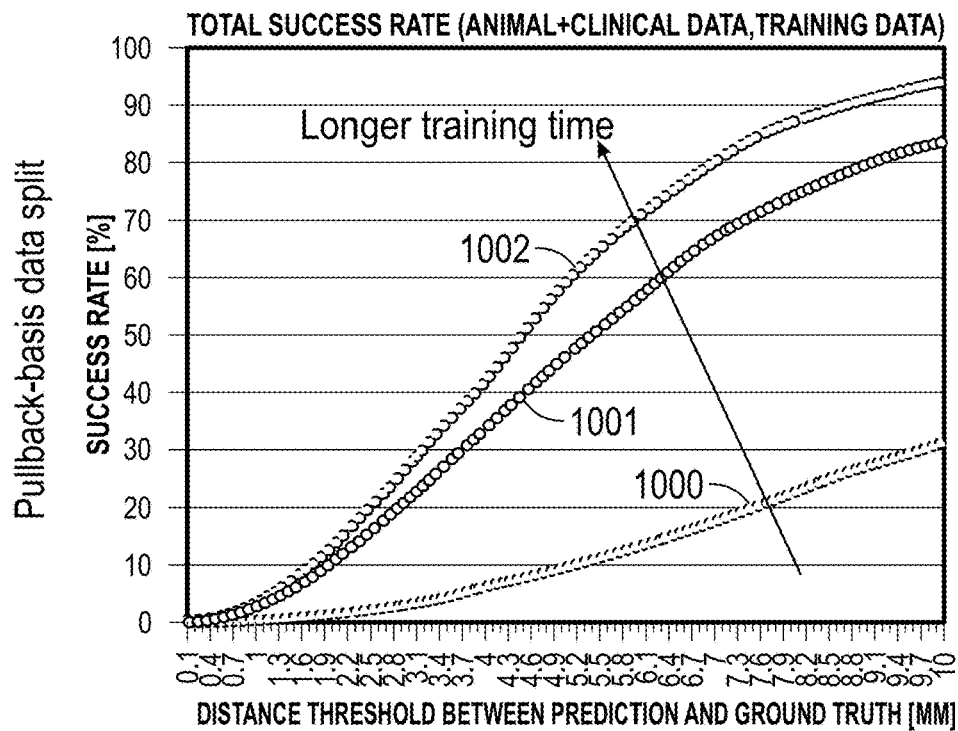
FIG. 10A

Validation data
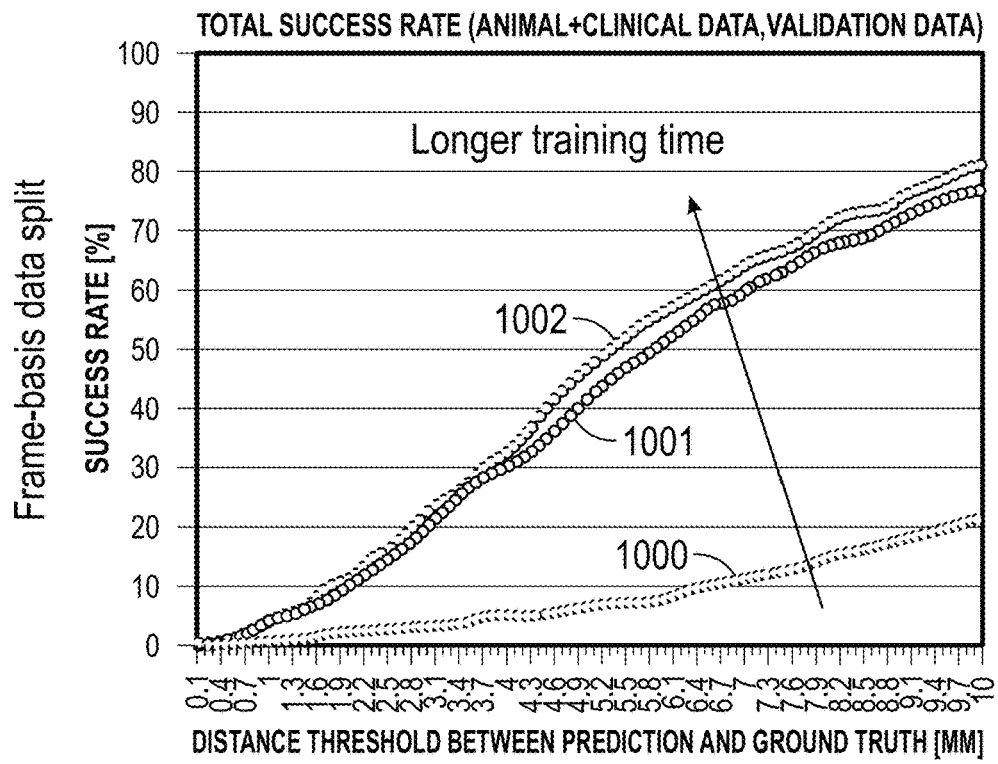
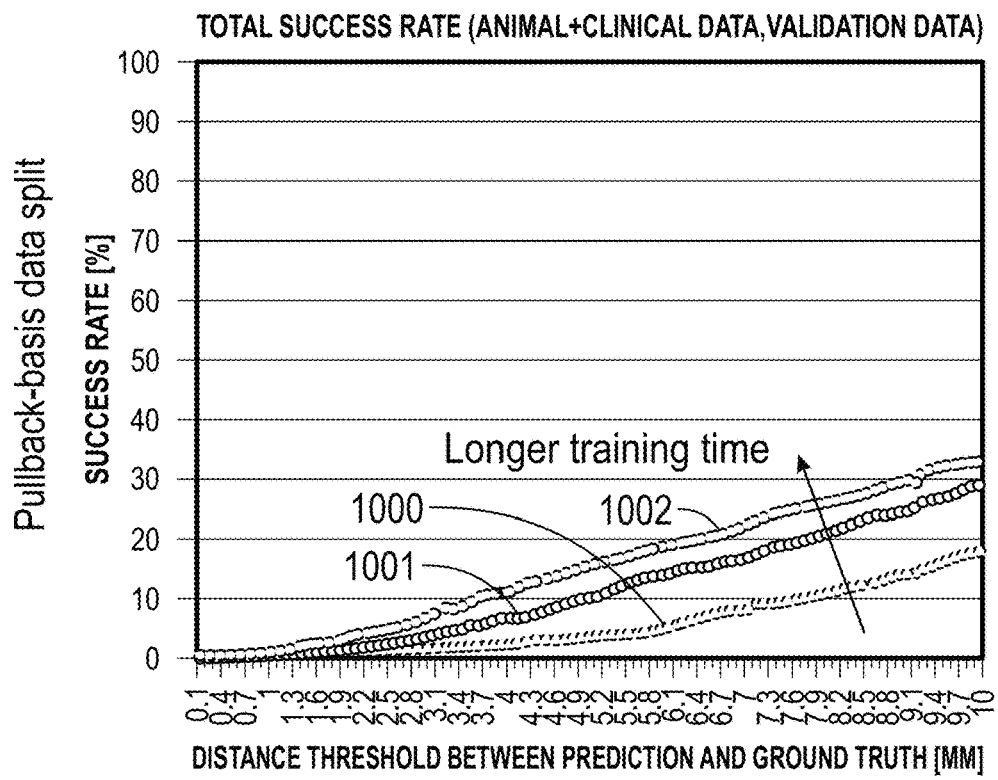
FIG. 10B

Test data
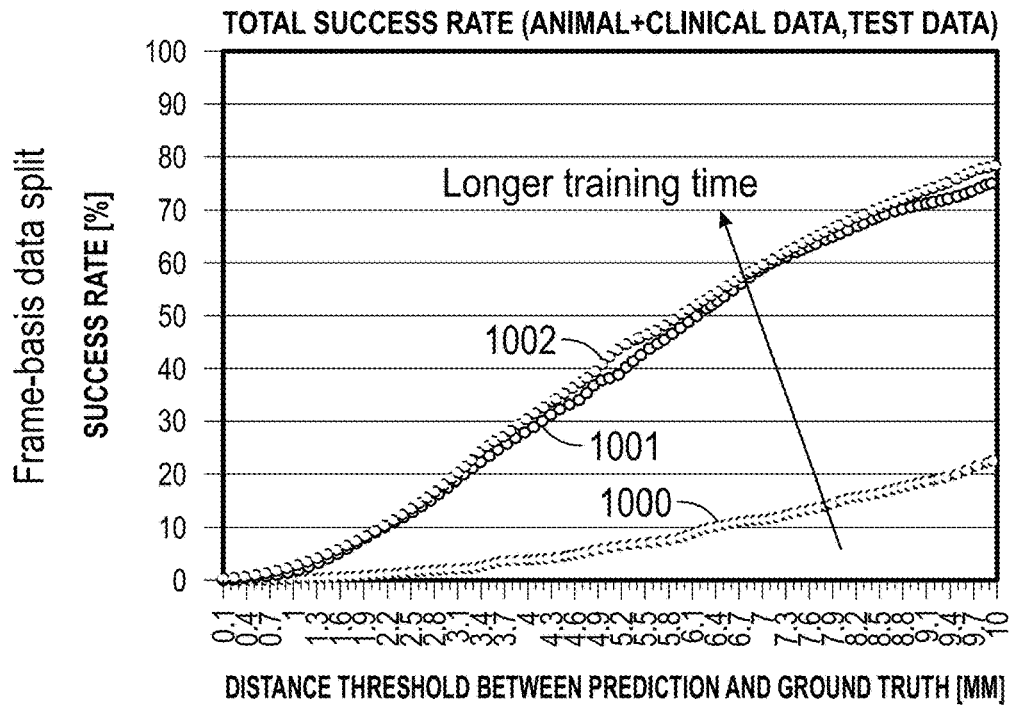
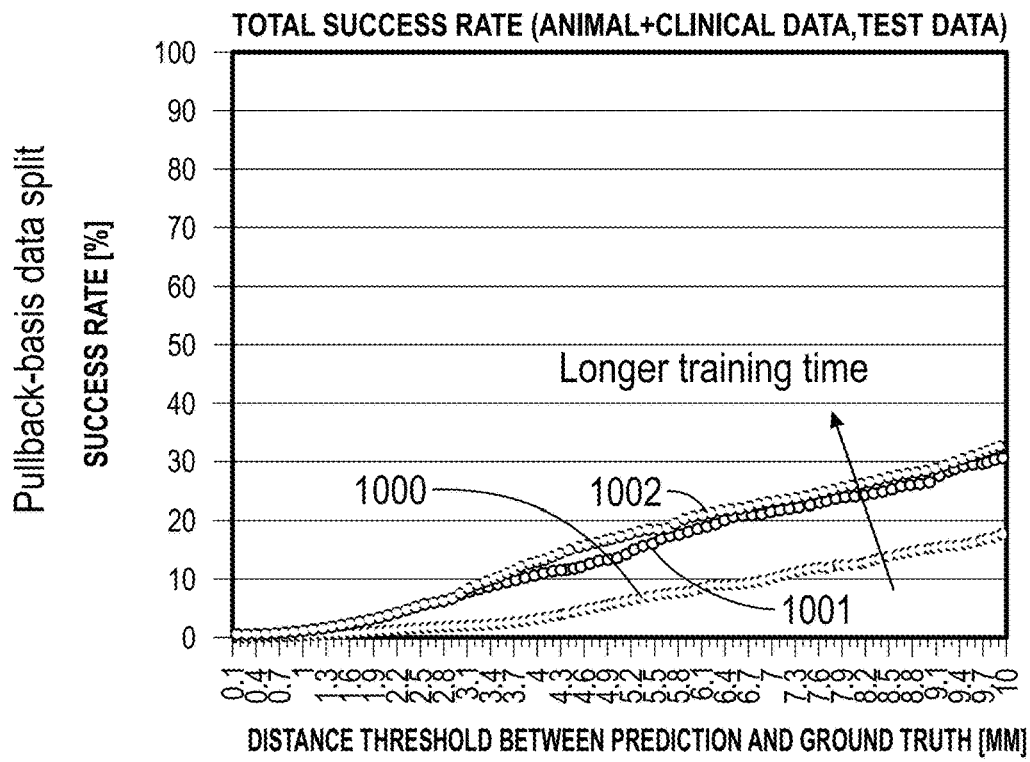
FIG. 10C

Root mean squared error (RMSE)

$$RMSE = \sqrt{\frac{1}{n}\sum_{1}^{n}(\hat{y} - y)^2}$$

where   $\hat{y}$: Predicted/Estimated normalized coordinates
        $y$: Actual normalized coordinates

No residual network (8 convolutional layers)

| Test pullback names | # of frames | n_ds054 (500 epochs) | | n_ds054_add6 (6500 epochs) | |
|---|---|---|---|---|---|
| | | Difference [pixel] | Difference [mm] | Difference [pixel] | Difference [mm] |
| Test TOTAL | 321 | 104.39 ± 41.95 | 30.95 ± 12.35 | 100.94 ± 51.34 | 29.91 ± 15.29 |
| Validation total | 865 | 93.63 ± 55.32 | 19.55 ± 10.60 | 32.35 ± 26.36 | 6.74 ± 5.56 | with residual network (34 convolutional layers)

| Test pullback names | # of frames | o_ds032 (500 epochs) | | o_ds032_add6 (6500 epochs) | |
|---|---|---|---|---|---|
| | | Difference [pixel] | Difference [mm] | Difference [pixel] | Difference [mm] |
| Test TOTAL | 321 | 121.89 ± 35.26 | 36.11 ± 10.52 | 114.47 ± 47.43 | 33.94 ± 14.10 |
| Validation total | 865 | 109.18 ± 58.88 | 22.50 ± 10.66 | 50.66 ± 35.32 | 10.67 ± 7.34 |

FIG. 11

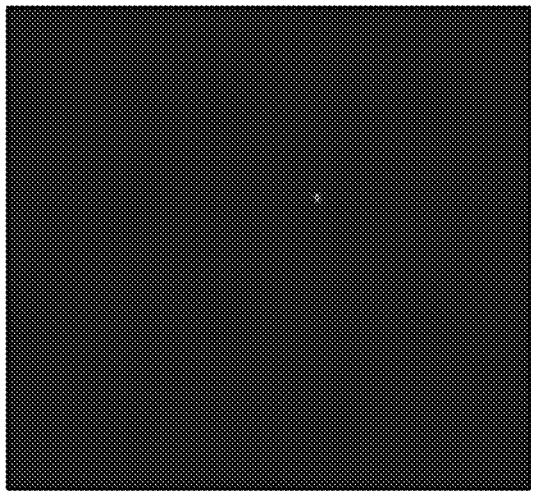
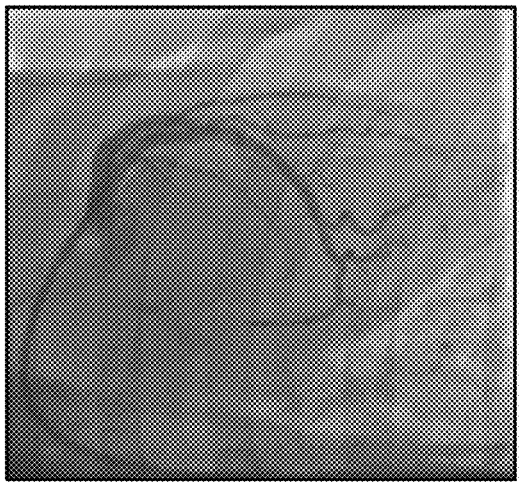
FIG. 17
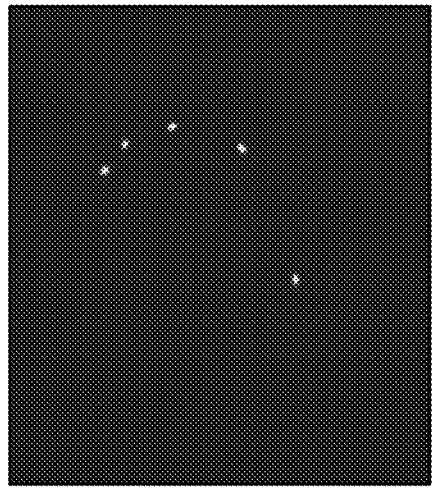
FIG. 18

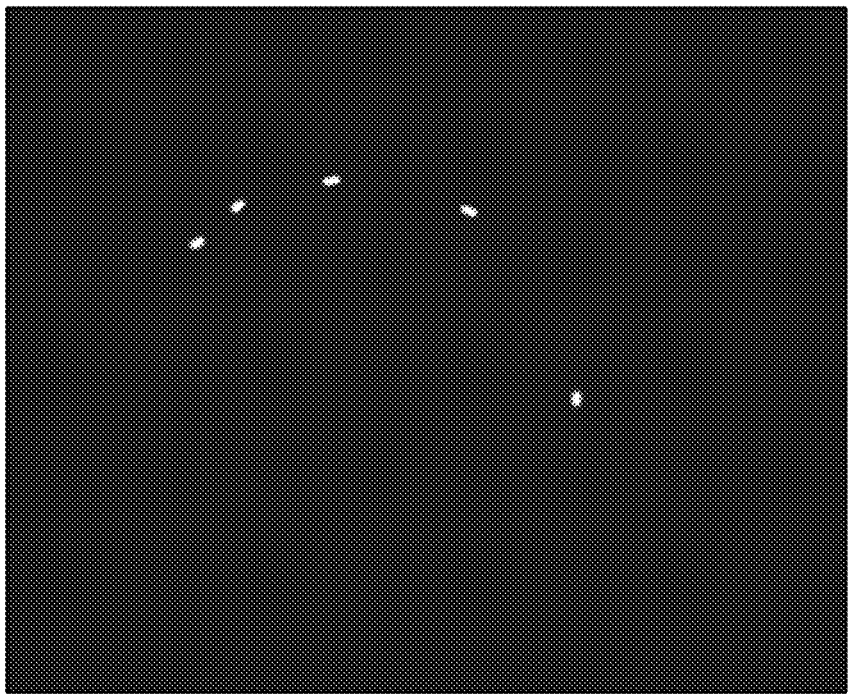
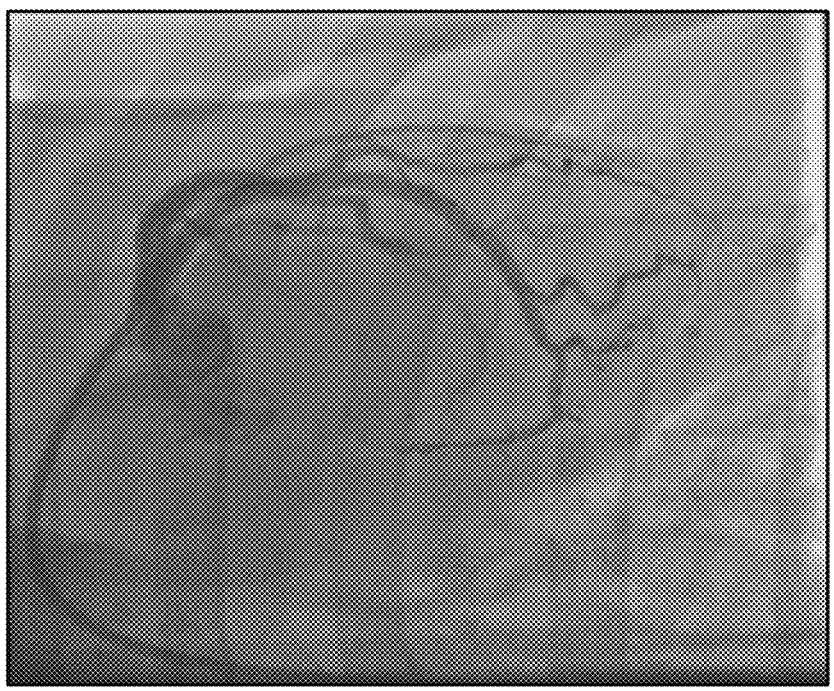
FIG. 20

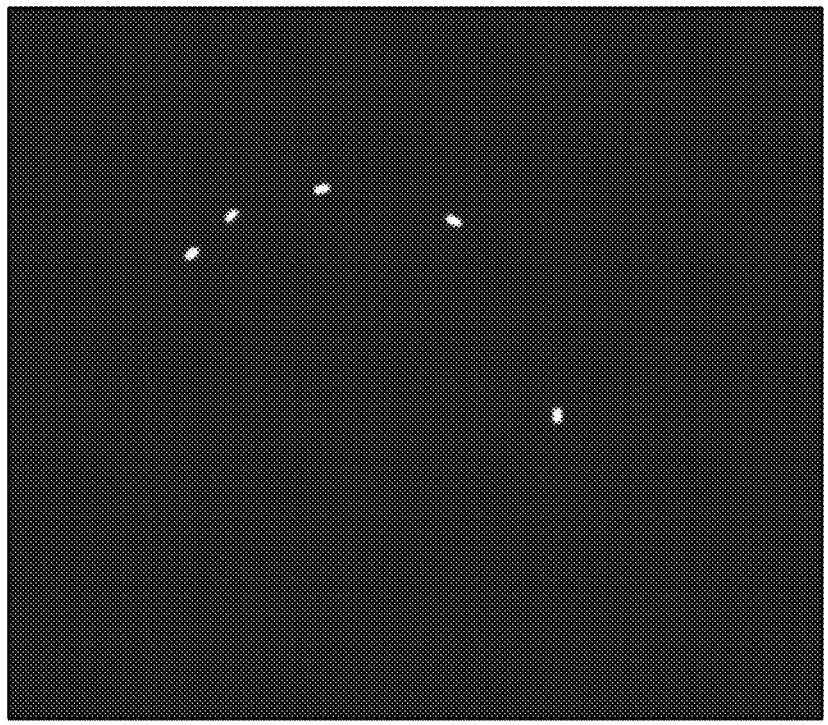
FIG. 23

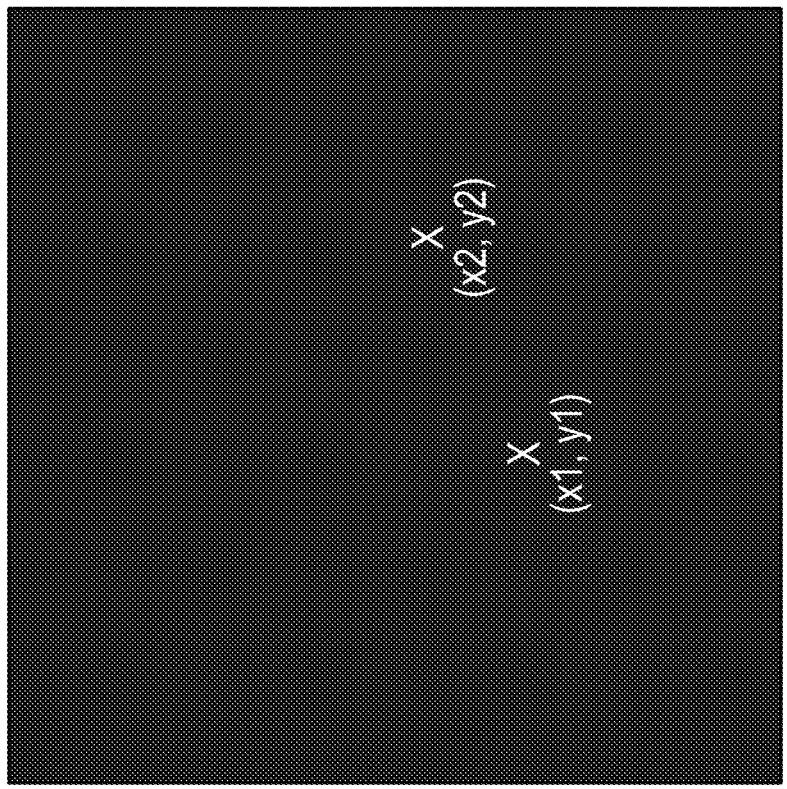
FIG. 25

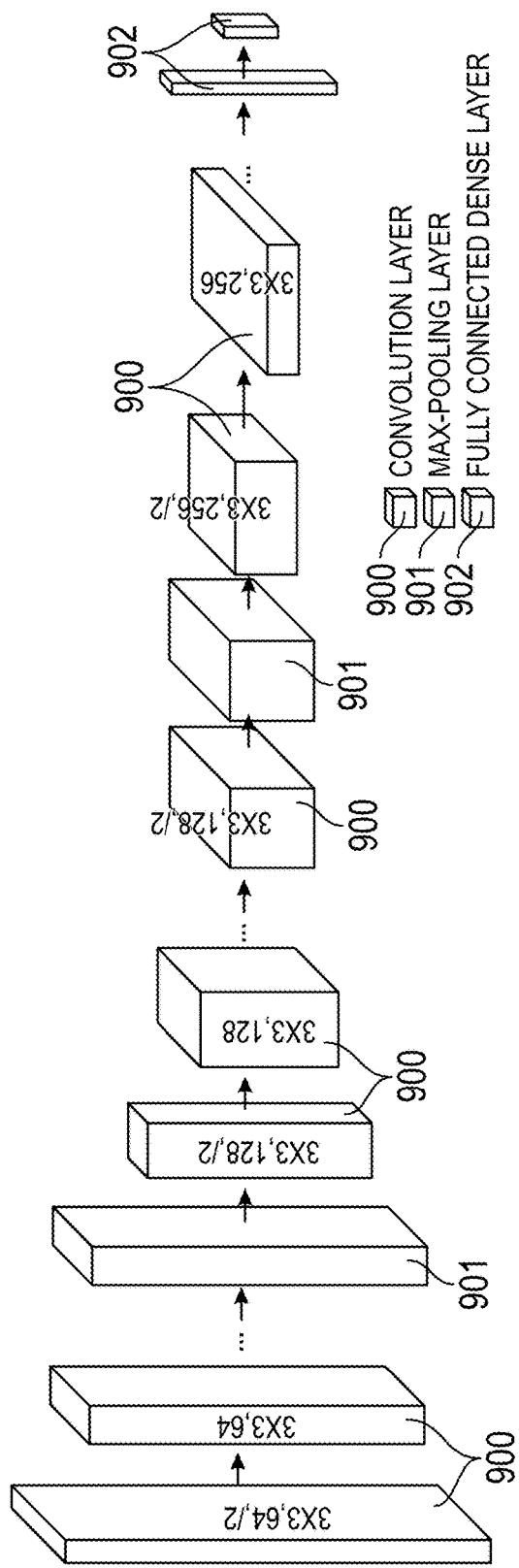
FIG. 26
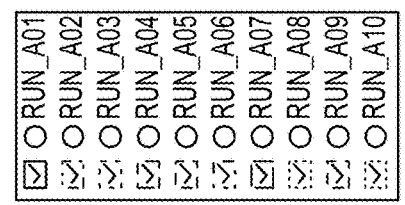
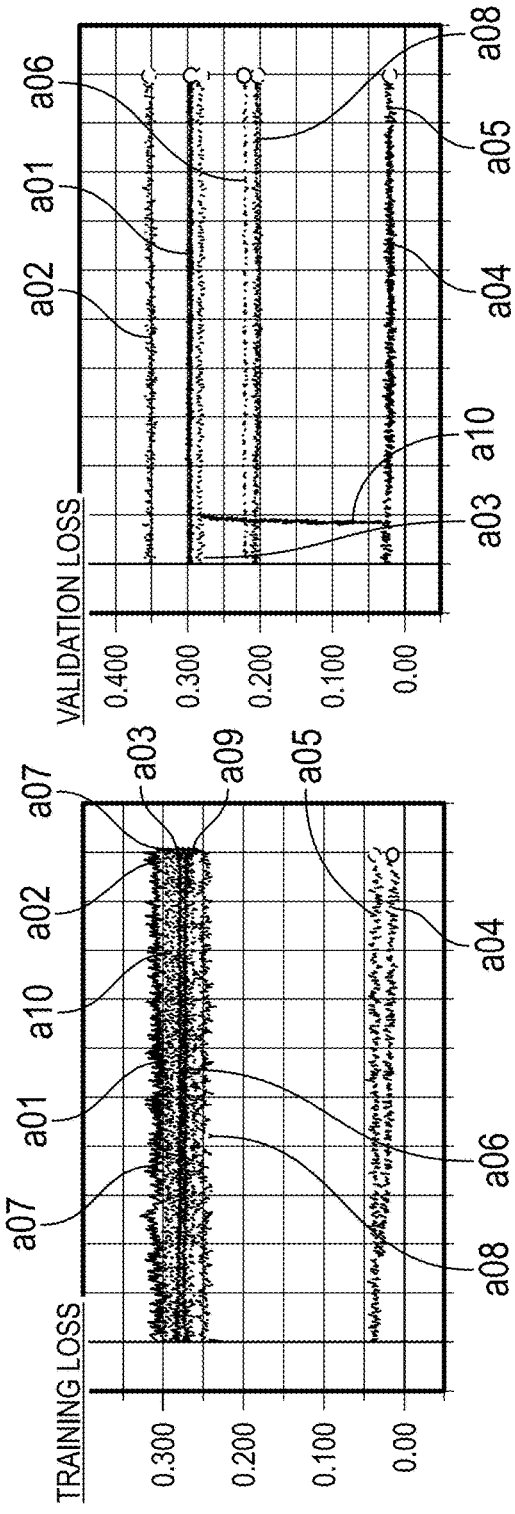
FIG. 27

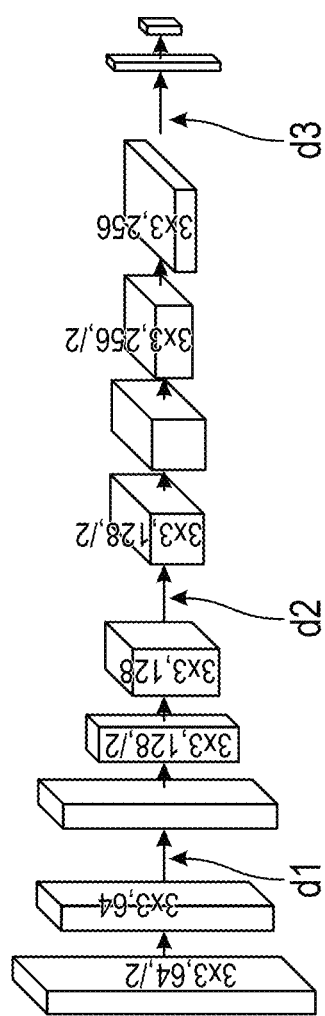
FIG. 28
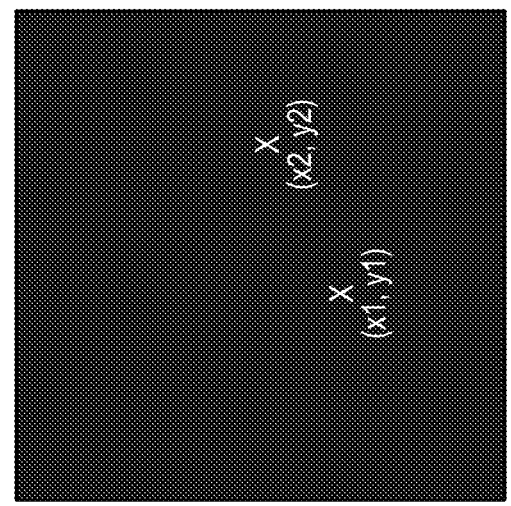
FIG. 29

ARTIFICIAL INTELLIGENCE COREGISTRATION AND MARKER DETECTION, INCLUDING MACHINE LEARNING AND USING RESULTS THEREOF

CROSS-REFERENCE TO RELATED APPLICATION(S)

This application relates, and claims priority, to U.S. Patent Application Ser. No. 62/903,630, filed Sep. 20, 2019, the entire disclosure of which is incorporated by reference herein in its entirety.

FIELD OF THE INVENTION

This present disclosure generally relates to computer imaging, computer vision, and/or to the field of medical imaging, particularly to devices/apparatuses, systems, methods, and storage mediums for artificial intelligence ("AI") co-registration (also referred to herein as "co-registration") and marker detection and/or for using one or more imaging modalities, including but not limited to, angiography, Optical Coherence Tomography (OCT), Multi-modality OCT (MM-OCT), near-infrared fluorescence (NIRAF), OCT-NIRAF, etc. Examples of OCT applications include imaging, evaluating and diagnosing biological objects, including but not limited to, for gastro-intestinal, cardio and/or ophthalmic applications, and being obtained via one or more optical instruments, including but not limited to, one or more optical probes, one or more catheters, one or more endoscopes, one or more capsules, and one or more needles (e.g., a biopsy needle). One or more devices, systems, methods and storage mediums for characterizing, examining and/or diagnosing, and/or measuring viscosity of, a sample or object in artificial intelligence application(s) using an apparatus or system that uses and/or controls one or more imaging modalities are discussed herein.

BACKGROUND OF THE INVENTION

Fiber optic catheters and endoscopes have been developed to gain access to internal organs. For example, in cardiology OCT (optical coherence tomography) has been developed to capture and visualize depth-resolved images of vessels with a catheter. The catheter, which may include a sheath, a coil and an optical probe, may be navigated to a coronary artery.

Optical coherence tomography (OCT) is a technique for obtaining high-resolution cross-sectional images of tissues or materials, and enables real time visualization. The aim of the OCT techniques is to measure the time delay of light by using an interference optical system or interferometry, such as via Fourier Transform or Michelson interferometers. Light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the greater are the differences in path length. Single mode fibers may be used for OCT optical probes, and double clad fibers may be used for fluorescence and/or spectroscopy.

A multi-modality system such as an OCT, fluorescence, and/or spectroscopy system with an optical probe is developed to obtain multiple information at the same time. During vascular diagnosis and intervention procedures, such as Percutaneous Coronary Intervention (PCI), users of optical coherence tomography (OCT) sometimes have difficulty understanding the tomography image in correlation with other modalities because of an overload of information, which causes confusion in image interpretation.

Percutaneous coronary intervention (PCI) has been improved dramatically by innovative imaging modalities, such as coronary angiography and intravascular imaging. Coronary angiography provides longitudinal silhouettes of coronary arteries, while intravascular imaging modalities provide cross-sectional information of coronary arteries. Since intravascular imaging modalities, such as intravascular ultrasound (IVUS) and optical coherence tomography (OCT), provide more precise information about a vessel lesion (e.g., lumen size, plaque morphology, and implanted devices), a system was developed that enables physicians to connect (i.e., coregister) between ex vivo and in vivo imaging modalities. One of the currently available methods requires generating a vessel centerline for coregistration from angiography data that is simultaneously acquired during IVUS/OCT pullback. The other one requires generating an imaging catheter path from angiography data that is acquired prior to IVUS/OCT pullback with user inputs.

More specifically, coronary angiography imaging and intravascular imaging are important imaging modalities for percutaneous coronary intervention (PCI). A coronary angiography provides longitudinal silhouettes of coronary arteries as aforementioned. The longitudinal silhouettes of the coronary artery are displayed on a monitor to help an interventional cardiologist guide a catheter insertion to a targeted region. Using coronary angiography during a PCI procedure may be preferred because it is easier to guide the catheter to a lesion when compared to other types of imaging modalities.

Another imaging modality used in PCI is intravascular imaging which provides cross-sectional information of coronary arteries as aforementioned. Intravascular imaging may include intravascular ultrasound (IVUS) and optical coherence tomography (OCT) that provides more precise lesion information, as aforementioned, than a coronary angiography image. However, relying only on an intravascular imaging modality such as IVUS or OCT in a PCI procedure is difficult when guiding a catheter to a targeted region (e.g., a vessel lesion) to gain information about lumen size, plaque morphology or implanted devices by way of example.

A system that enables physicians to connect between two different imaging modalities including for example both coronary angiography and intravascular imaging during PCI involves co-registration. Co-registration (also referred to herein as "coregistration") refers to the spatial alignment of a series of images. For example, co-registration may refer to the alignment of functional (intravascular imaging) and anatomical (coronary angiography) images of a patient who undergoes PCI to map functional information into anatomical space. One benefit associated with co-registering angiography imaging with intravascular imaging includes determining where along the longitudinal silhouette of the coronary artery in an angiography image frame the intravascular image was acquired.

Coregistration between angiography and intravascular imaging has two steps: (1) time synchronization of angiography and intravascular imaging, and (2) radiopaque marker detection in an angiography image to identify the acquisition location of intravascular images. However, current methods with conventional image processing techniques may provide a limited success rate due to difficulties that exist in step (2). For example, although a radiopaque marker may be seen as a darkest spot in an angiography image, multiple similar dark spots may be found in the same angiography image, which can pose a challenge for conventional computational image processing techniques to reliably identify the correct point (the one representing the marker of interest or target of interest) from a multitude of candidate points that appear similar in the angiography image.

Accordingly, it would be desirable to provide at least one imaging or optical apparatus/device, system, method, and storage medium that applies machine learning, especially deep learning, to identify one or more markers in angiography image frames with a higher success rate when compared to traditional techniques, and to use the result (i.e., identified marker position or positions) to perform coregistration more efficiently.

SUMMARY OF THE INVENTION

Accordingly, it is a broad object of the present disclosure to provide imaging (e.g., OCT, NIRAF, etc.) apparatuses, systems, methods and storage mediums for using and/or controlling multiple imaging modalities, that apply machine learning, especially deep learning, to identify (e.g., detect, locate, or localize, etc.) a marker in an angiography image frame with greater or maximum success, and that use the results to perform coregistration more efficiently or with maximum efficiency. It is also a broad object of the present disclosure to provide OCT devices, systems, methods and storage mediums using an interference optical system, such as an interferometer (e.g., spectral-domain OCT (SD-OCT), swept-source OCT (SS-OCT), multimodal OCT (MM-OCT), etc.).

One or more embodiments of the present disclosure may apply machine learning, especially deep learning, to identify one or more markers in angiography image frames (e.g., one or more frames from a video, one or more frames from an image or images, etc.) without user input(s) that define an area where intravascular imaging pullback occurs. Using artificial intelligence, for example (but not limited to), deep/machine learning, residual learning, a computer vision task (keypoint or object detection and/or image segmentation), using a unique architecture structure of a model or models, using a unique training process, using input data preparation techniques, using input mapping to the model, using post-processing and interpretation of the output data, etc., one or more embodiments of the present disclosure may achieve a better or maximum success rate of marker detection from angiography data without (or with less) user interactions, and may reduce processing and/or prediction time to display coregistration result(s) based on the marker detection result(s). In this present disclosure, a model may be defined as software that takes images as input and returns predictions for the given images as output. In one or more embodiments a model may be a particular instance of a model architecture (set of parameter values) that has been obtained by model training and selection using a machine learning and/or optimization algorithm/process. A model generally consists or is comprised of the following parts: an architecture defined by a source code (e.g., a convolutional neural network comprised of layers of parameterized convolution kernels and activation functions, etc.) and configuration values (parameters, weights or features) that are initially set to random values and are then over the course of the training iteratively optimized given data examples (e.g., image-label pairs), an objective function (loss function), and an optimization algorithm (optimizer).

One or more embodiments of the present disclosure may achieve the efficient marker detection and/or efficient coregistration result(s) by creating an identifier or detector to detect a radiopaque marker on intravascular imaging catheter from angiography image. In one or more embodiments, the angiography data may be acquired during intravascular imaging pullback using a catheter having a radiopaque marker that may be visualized in an angiography image. In one or more embodiments, a ground truth identifies a location of the radiopaque marker. In one or more embodiments, a model (which, in one or more embodiments, may be software, software/hardware combination, or a procedure that utilizes one or more machine or deep learning algorithms/procedures/processes that has/have been trained on data to make one or more predictions for future, unseen data) has enough resolution to predict the marker location with sufficient accuracy depending on the application or procedure being performed. The performance of the model may be further improved by subsequently adding more training data and retraining the model to create a new instance of the model with better or optimized performance. For example, additional training data may include data based on user input, where the user may identify or correct the location of the radiopaque marker in an image. One or more embodiments may use the identifier or detector to detect the radiopaque marker(s).

One or more methods, medical imaging devices, Intravascular Ultrasound (IVUS) or Optical Coherence Tomography ("OCT") devices, imaging systems, and/or computer-readable storage mediums for detecting marker location(s) and/or for performing coregistration using artificial intelligence may be employed in one or more embodiments of the present disclosure.

In one or more embodiments, an artificial intelligence training apparatus may include: a memory; one or more processors in communication with the memory, the one or more processors operating to: acquire or receive angiography image data; establish ground truth for all the acquired angiography image data; split the acquired angiography image data into training, validation, and test sets or groups; choosing or sampling a particular set of hyper-parameter values for model training, including, but not limited to, model architecture, the learning rate, and the initialization of parameter values; iteratively train a model using data examples from the training set or group and evaluate the model using data examples from the validation set or group and a predefined metric over multiple iterations; stop the training and evaluation iterations using one or more predefined or dynamically determined stopping criteria; and save the trained model to memory; etc. One or more embodiments may repeat the training, and evaluation procedure, for a variety of hyper-parameter choices and finally select one or more models with the optimal, highest, and/or improved performance defined by one or more predefined evaluation metrics.

In one or more embodiments, the one or more processors may further operate to split the ground truth data into sets or groups for training, validation, and testing. The one or more processors may further operate to one or more of the following: (i) detect or identify the marker(s) or radiopaque marker(s) in the angiography image data based on the created identifier or detector; (ii) calculate or improve a marker detection success rate using application of machine learning or deep learning; (iii) decide on the model to be trained based on a marker detection success rate associated with the model (e.g., if an apparatus or system embodiment has multiple models to be saved, which have already been trained previously, a method of the apparatus/system may select a model for further training based on a previous success rate, based on a predetermined success factor, or based on which model is more optimal than another(s), etc.); (iv) calculate a coregistration success rate and/or determine whether a location of the detected marker is correct based on the trained model; and (v) evaluate the marker detection success rate and/or the coregistration success rate using a root mean squared error between a predicted location and an actual location of the marker. In one or more embodiments, the one or more processors may further operate to one or more of the following: (i) split the acquired or received angiography image data into data sets or groups having a certain ratio or percentages, for example, 70% training data, 15% validation data, and 15% test data; (ii) split the acquired or received angiography image data randomly; (iii) split the acquired or received angiography image data randomly either on a pullback-basis, or a frame-basis; (iv) split the acquired or received angiography image data based on or using a new set of a certain or predetermined kinds of data; and (v) split the acquired or received angiography image data based on or using a new set of a certain or pre-determined data type, the new set being one or more of the following: a new pullback-basis data set, a new frame-basis data set, new clinical data, new animal data, new potential additional training data, new data for a first type of catheter where the new data has a marker that is similar to a marker of a catheter used for the acquired or received angiography image data, new data having a marker that is similar to a marker of an Optical Coherence Tomography (OCT) catheter. The one or more processors may further operate to one or more of the following: (i) employ data quality control; (ii) allow a user to manually select training samples or training data; (iii) allow the user to identify a marker or a target for detection and to use such a sample as a data point for model training; and (iv) use any angio image that is captured during Optical Coherence Tomography (OCT) pullback for testing. In one or more embodiments, the one or more processors may further operate to one or more of the following: (i) perform image pre-processing; (ii) perform image pre-processing by normalizing pixel values; and (iii) perform image pre-processing by normalizing pixel values for each individual angio frame before training starts and/or for each batch of angio frames that are input to the model for each iteration of the training. The one or more processors may operate to one or more of the following after selecting a model architecture or configuration for training by a user or the system based on a pre-determined criterion, to determine a kind of data to be used, input, and outputs: (i) when the model is a segmentation or classification model, the input is an individual angio image frame, and the output is a corresponding segmented, labeled, or masked image; (ii) when the model is a segmentation or classification model, the input is an individual angio image frame, and the output is a corresponding segmented, labeled, or masked image, where foreground pixels demarcating a marker area have positive values and background pixels have zero values; (iii) when the model is an object detection or regression model, the input is an individual angio image frame, and the output is a corresponding set of spatial coordinate(s) defining the marker location(s) or the target marker; and (iv) when the model performs a combination of segmentation (pixel classification) and/or object detection (spatial coordinate point regression), the input includes a combination of individual angio frames, and the output includes a combination of one or more of the following: a segmented or masked image, a segmented or masked image where foreground pixels demarcating a marker area have positive values and background pixels have zero values, and coordinate(s) of the marker location(s) or a coordinate of the target marker. In one or more embodiments, the segmentation model may use post-processing after obtaining the segmented or masked image to determine coordinate points of the marker location.

One or more embodiments may include or have one or more of the following: (i) the parameters include one or more hyper-parameters; (ii) the saved, trained model is used as a created detector for identifying or detecting a marker(s) or radiopaque marker(s) in angiography image data; (iii) the model is one or a combination of the following: a segmentation model, a segmentation model with post-processing, a model with pre-processing, a model with post-processing, a segmentation model with pre-processing, a deep learning or machine learning model, a semantic segmentation model or classification model, an object detection or regression model, an object detection or regression model, a combination of a semantic segmentation model and an object detection or regression model, a model using repeated segmentation model technique(s), a model using feature pyramid(s), and a model using repeated object detection or regression model technique(s); (iv) the ground truth includes one or more of the following: locations of two endpoints of a major axis of a target marker in each angiography frame, locations of two endpoints of a major axis of a target marker in each angiography frame captured during Optical Coherence Tomography (OCT) pullback, a mask including a line that connects the two endpoint locations with a certain width as a positive area for the segmentation model, all of the markers included in an the acquired or received angiography image data, a centroid of two edge locations, a centroid of two edge locations for the regression or object detection model, and two marker locations in each frame of the acquired or received angiography image data graphically annoted by a user or an expert of the apparatus; (v) the one or more processors further operate to use one or more neural networks, convolutional neural networks, or recurrent neural networks to detect the marker(s) or radiopaque marker(s); (vi) the one or more processors further operate to estimate a generalization error of the trained model with data in the test set or group; and (vii) the one or more processors further operate to estimate a generalization error of multiple trained models (ensemble) with data in the test set or group, and to select one model based on its performance on the validation set or group.

In one or more embodiments, an artificial intelligence detection apparatus may include: one or more processors that operate to: acquire or receive angiography image data; receive a trained model or load a trained model from a memory; apply the trained model to the acquired or received angiography image data; select one angiography frame; detect a marker location on the selected angiography frame with the trained model, the detected marker location defining detected results; check whether the marker location is correct or accurate; in an event that the marker location is not correct or accurate, then modify the detected results or the detected marker location, and repeat the check as to whether the marker location is correct or accurate, or in an event that the marker location is correct or accurate, then check whether all of the angiography frames have been checked for correctness or accuracy; and in an event that all of the angiography frames have not been checked for correctness or accuracy, then select another angiography frame and repeat the detection of a marker location and the check of whether the marker location is correct or accurate or not for the another angiography frame.

In one or more embodiments of a detection apparatus, the one or more processors may further operate to one or more of the following: (i) in an event that all of the angiography frames have been checked for correctness or accuracy, then perform coregistration based on the detected marker location; (ii) display the detected marker location on a display; (iii) display the detected marker location on the display such that the detected marker location is overlayed on angiography data; (iv) display the modified detected results and/or the modified marker location on the display; (v) insert an intravascular imaging catheter that has a marker or radiopaque marker into an object or sample; and (vi) acquire or receive the angiography image data during a pullback operation of the intravascular imaging catheter.

The one or more processors may further operate to use one or more neural networks, convolutional neural networks, and/or recurrent neural networks to one or more of: load the trained model, select a set of angiography frames, detect the marker location for each frame, determine whether the detected marker location is appropriate with respect to given prior knowledge, for example, vessel location and pullback direction, modify the detected results or the detected marker location for each frame, display the detected marker location on the display, perform the coregistration, insert the intravascular image, and acquire or receive the angiography image data during the pullback operation.

In one or more embodiments, the object or sample may include one or more of the following: a vessel, a target specimen or object, and a patient.

The one or more processors may further operate to perform the coregistration by co-registering the acquired or received angiography image and an obtained one or more Optical Coherence Tomography (OCT) or Intravascular Ultrasound (IVUS) images or frames.

In one or more embodiments, a loaded, trained model may be one or a combination of the following: a segmentation (classification) model, a segmentation model with pre-processing, a segmentation model with post-processing, an object detection (regression) model, an object detection model with pre-processing, an object detection model with post-processing, a combination of a segmentation (classification) model and an object detection (regression) model, a deep convolutional neural network model, a recurrent neural network model with long short-term memory that can take temporal relationships across images or frames into account, a model using feature pyramid(s) that can take different image resolutions into account, and/or a model using residual learning technique(s).

In one or more embodiments, the one or more processors may further operate to one or more of the following: (i) display the angiography data along with an image for each of one or more imaging modalities on the display, wherein the one or more imaging modalities include one or more of the following: a tomography image; an Optical Coherence Tomography (OCT) image; a fluorescence image; a near-infrared fluorescence (NIRAF) image; a near-infrared fluorescence (NIRAF) in a predetermined view, a carpet view, and/or an indicator view; a three-dimensional (3D) rendering; a 3D rendering of a vessel; a 3D rendering of a vessel in a half-pipe view or display; a 3D rendering of the object; a lumen profile; a lumen diameter display; a longitudinal view; computer tomography (CT); Magnetic Resonance Imaging (MRI); Intravascular Ultrasound (IVUS); an X-ray image or view; and an angiography view; and (ii) change or update the displays for the angiography data along with each of the one or more imaging modalities based on the modified detection results and/or the modified marker location.

One or more embodiments of a method for training a model using artificial intelligence may include: acquiring or receiving angiography image data; establishing ground truth for all the acquired angiography image data; collecting image data annotations; splitting the acquired angiography image data into training, validation, and test sets or groups; choosing hyper-parameters for model training, including the model architecture, the learning rate, and initialization of parameter values; iteratively training a model using data in the training set or group and evaluate the model using data in the validation set or group over the course of multiple iterations; stop the training and evaluation iterations using one or more predefined or dynamically determined stopping criteria, and save the trained model to memory. One or more embodiments may repeat the selection, training, and evaluation procedure, for a variety of model configurations (e.g., hyper-parameter values) and finally select one or more models with the highest performance defined by one or more predefined evaluation metrics.

One or more embodiments of training methods may include or have one or more of the following conditions: (i) the parameters include one or more hyper-parameters; (ii) the saved, trained model is used as a created detection system for identifying or detecting a marker(s) or radiopaque marker(s) in angiography image data; (iii) the model is one or a combination of the following: a segmentation (classification) model, a segmentation model with pre-processing, a segmentation model with post-processing, an object detection (regression) model, an object detection model with pre-processing, an object detection model with post-processing, a combination of a segmentation (classification) model and an object detection (regression) model, a deep convolutional neural network model, a recurrent neural network model with long short-term memory that can take temporal relationships across images or frames into account, a model using feature pyramid(s) that can take different image resolutions into account, and/or a model using residual learning technique(s); (iv) the ground truth includes one or more of the following: locations of two endpoints of a major axis of a target marker in each angiography frame, locations of two endpoints of a major axis of a target marker in each angiography frame captured during Optical Coherence Tomography (OCT) pullback, a mask including a line that connects the two endpoint locations with a certain width as a positive area for the segmentation model, all of the markers included in an the acquired or received angiography image data, a centroid of two edge locations, a centroid of two edge locations for the regression or object detection model, and two marker locations in each frame of the acquired or received angiography image data graphically annoted by a user or an expert of the apparatus; (v) the one or more processors further operate to use one or more neural networks or convolutional neural networks to one or more of: train the model, estimate the generalization error, determine whether the performance of the trained model is sufficient or not, and/or to detect the marker(s) or radiopaque marker(s); (vi) the method further comprises estimating a generalization error of the trained model with data in the test set or group; and (vii) the method further comprises estimating a generalization error of multiple trained models with data in the test set or group, and selects one model based on its performance on the validation set or group.

One or more embodiments of a non-transitory computer-readable storage medium storing at least one program for causing a computer to execute a method for training a model using artificial intelligence may be used with any method(s) discussed in the present disclosure, including but not limited to, a method including: acquiring or receiving angiography image data; establishing ground truth for all the acquired angiography image data; splitting the acquired angiography image data into training, validation, and test sets or groups; choosing or sampling hyper-parameter values for model training, including model architecture, learning rate, and the initialization of parameter values; training a model with data in the training set or group and evaluate the model with data in the validation set or group; determining whether the performance of the trained model is sufficient; and in the event that the trained model is not sufficient, then repeating the choosing/sampling, the training, and the determining/evaluation, or, in the event that the trained model is sufficient, saving the trained model to a memory.

One or more embodiments of a method for detecting a marker or a radiopaque marker in angiography image data and/or for performing coregistration may include acquiring or receiving angiography image data; receiving a trained model or loading a trained model from a memory; applying the trained model to the acquired or received angiography image data; selecting one angiography frame; detecting a marker location on the selected angiography frame with the trained model, the detected marker location defining detected results; checking whether the marker location is correct or accurate; in an event that the marker location is not correct or accurate, then modifying the detected results or the detected marker location, and repeating the check as to whether the marker location is correct or accurate, or in an event that the marker location is correct or accurate, then checking whether all of the angiography frames have been checked for correctness or accuracy; and in an event that all of the angiography frames have not been checked for correctness or accuracy, then selecting another angiography frame and repeating the detection of a marker location and the check of whether the marker location is correct or accurate or not for the another angiography frame. The method may include one or more of the following: (i) in an event that all of the angiography frames have been checked for correctness or accuracy, performing coregistration based on the detected marker location; (ii) displaying the detected marker location on a display; (iii) displaying the detected marker location on the display such that the detected marker location is overlayed on angiography data; (iv) displaying the modified detected results and/or the modified marker location on the display; (v) inserting an intravascular imaging catheter that has a marker or radiopaque marker into an object or sample; and (vi) acquiring or receiving the angiography image data during a pullback operation of the intravascular imaging catheter.

One or more embodiments of any method discussed herein (e.g., training method(s), detecting method(s), imaging or visualization method(s), artificial intelligence method(s), etc.) may be used with any feature or features of the apparatuses, systems, other methods, storage mediums or other structures discussed herein.

One or more embodiments of a non-transitory computer-readable storage medium storing at least one program for causing a computer to execute a method for detecting a marker using artificial intelligence and/or performing coregistration using artificial intelligence may be used with any method(s) discussed in the present disclosure, including but not limited to, a method including: acquiring or receiving angiography image data; receiving a trained model or loading a trained model from a memory; applying the trained model to the acquired or received angiography image data; selecting one angiography frame; detecting a marker location on the selected angiography frame with the trained model, the detected marker location defining detected results; checking whether the marker location is correct or accurate; in an event that the marker location is not correct or accurate, then modifying the detected results or the detected marker location, and repeating the check as to whether the marker location is correct or accurate, or in an event that the marker location is correct or accurate, then checking whether all of the angiography frames have been checked for correctness or accuracy; and in an event that all of the angiography frames have not been checked for correctness or accuracy, then selecting another angiography frame and repeating the detection of a marker location and the check of whether the marker location is correct or accurate or not for the another angiography frame.

One or more embodiments of a method for detecting a marker or a radiopaque marker in angiography image data and/or for performing coregistration may include one or more of the following: (i) in an event that all of the angiography frames have been checked for correctness or accuracy, performing coregistration based on the detected marker location; (ii) displaying the detected marker location on a display; (iii) displaying the detected marker location on the display such that the detected marker location is overlayed on angiography data; (iv) displaying the modified detected results and/or the modified marker location on the display; (v) inserting an intravascular imaging catheter that has a marker or radiopaque marker into an object or sample; and (vi) acquiring or receiving the angiography image data during a pullback operation of the intravascular imaging catheter.

One or more of the artificial intelligence features discussed herein that may be used in one or more embodiments of the present disclosure, includes but is not limited to, using one or more of deep learning, a computer vision task, keypoint detection, a unique architecture of a model or models, a unique training process or algorithm, a unique optimization process or algorithm, input data preparation techniques, input mapping to the model, post-processing, and/or interpretation of the output data as substantially described herein or as shown in any one of the accompanying drawings.

In one or more embodiments, a radiopaque marker may be detected and tracked using an algorithm, such as, but not limited to, the Viterbi algorithm.

One or more embodiments may automate characterization of stenosis in angiography images using convolutional neural networks, any other types of neural network(s), and may fully automate frame detection on angiographies using training (e.g., offline training) and using applications (e.g., online application(s)) to extract and process frames via deep learning.

One or more embodiments of the present disclosure may track and/or calculate a radiopaque marker detection success rate.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

According to other aspects of the present disclosure, one or more additional devices, one or more systems, one or more methods and one or more storage mediums using OCT and/or other imaging modality technique(s) to detect marker(s) and to perform coregistration using artificial intelligence, including, but not limited to, deep or machine learning, using results of the marker detection for performing coregistration, etc., are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 5 is a diagram showing several examples of measuring marker detection success rate in accordance with one or more aspects of the present disclosure;

FIGS. 6A-6B are an example ground truth for at least one embodiment of a segmentation model and an input through an output of at least one embodiment of a segmentation model method, respectively, in accordance with one or more aspects of the present disclosure;

FIG. 10 (made of FIGS. 10A, 10B, and 10C) includes several examples of training data, validation data, and test data along with a measure of success rate in accordance with one or more aspects of the present disclosure;

FIG. 11 includes several examples of test and validation data along with root mean squared error calculations for one or more embodiments of an object detection model in accordance with one or more aspects of the present disclosure;

FIG. 17 shows an example input image (left) and the corresponding output image (right) for one or more machine-learning applications in accordance with one or more aspects of the present disclosure;

FIG. 18 shows an example input image (left) and the corresponding output image (right) after updating segmentation in accordance with one or more aspects of the present disclosure;

FIG. 20 shows an example input image (left) and the corresponding output image (right) in accordance with one or more aspects of the present disclosure;

FIG. 23 shows an example input image (left) and the corresponding output image (right) for segmentation model (s) in accordance with one or more aspects of the present disclosure;

FIG. 25 shows an example input image (left) and the corresponding output image (right) for regression model(s) in accordance with one or more aspects of the present disclosure;

FIG. 26 shows a created architecture of or for a regression model(s) in accordance with one or more aspects of the present disclosure;

FIG. 27 shows at least one embodiment example of model selection (e.g., showing a plot of loss values of models with different hyper-parameter configurations on the training and validation sets at different time points during model training) in accordance with one or more aspects of the present disclosure;

FIG. 28 shows a convolutional neural network architecture in accordance with one or more aspects of the present disclosure;

FIG. 29 shows an example input image (left) and the corresponding output image (right) for regression model(s) in accordance with one or more aspects of the present disclosure;

DETAILED DESCRIPTION OF THE PRESENT INVENTION

One or more devices, systems, methods and storage mediums for characterizing tissue, or an object, using one or more imaging techniques or modalities (such as, but not limited to, OCT, fluorescence, NIRAF, etc.), and using artificial intelligence for detecting a marker(s) and/or performing coregistration are disclosed herein. Several embodiments of the present disclosure, which may be carried out by the one or more embodiments of an apparatus, system, method and/or computer-readable storage medium of the present disclosure are described diagrammatically and visually in at least FIGS. 1A through 31 and other tables and figures included herein below.

Turning now to the details of the figures, imaging modalities may be displayed in one or more ways as discussed herein. One or more displays discussed herein may allow a user of the one or more displays to use, control and/or emphasize multiple imaging techniques or modalities, such as, but not limited to, OCT, NIRAF, etc., and may allow the user to use, control, and/or emphasize the multiple imaging techniques or modalities synchronously.

Figure 1A:
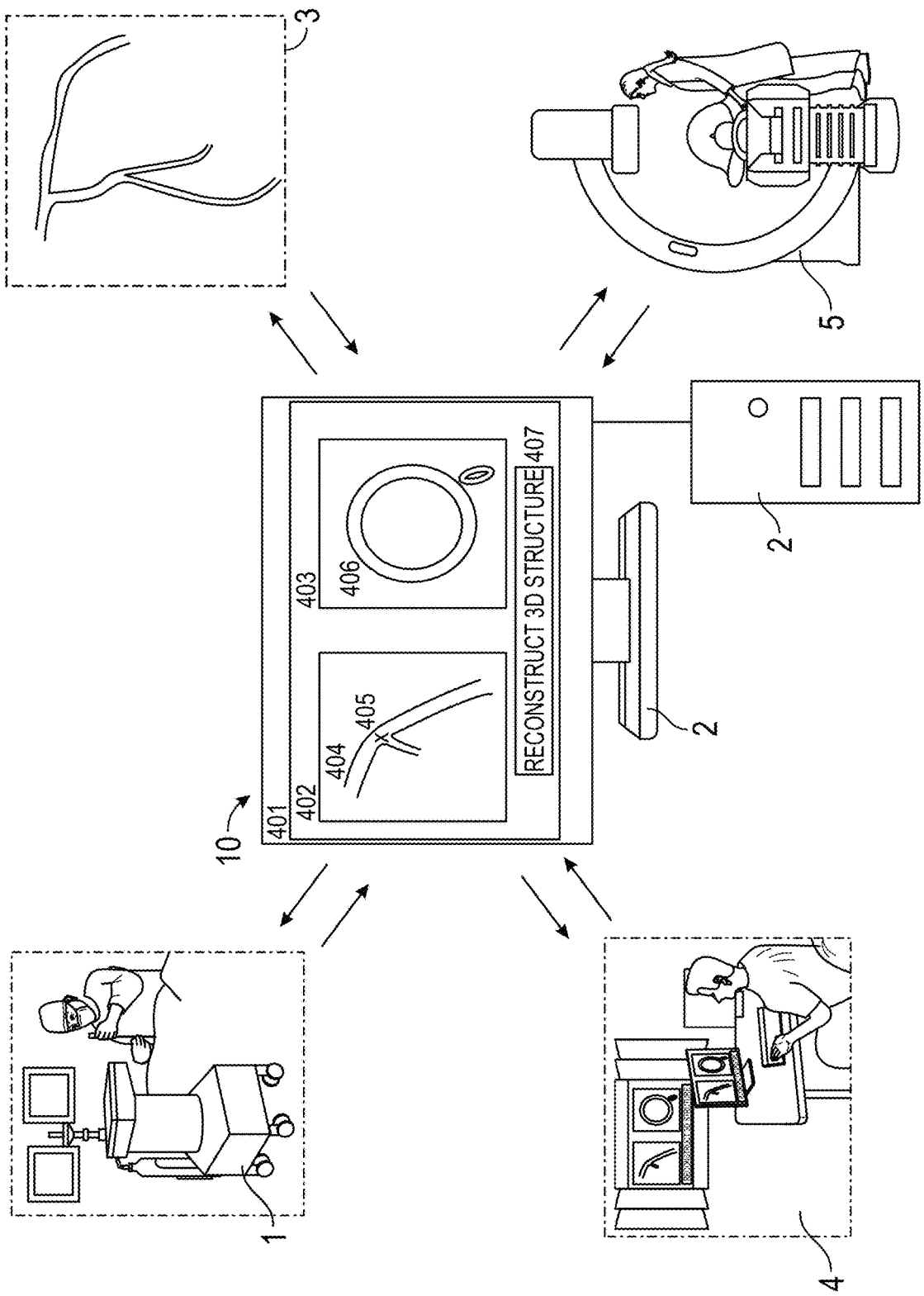
FIG. 1A is a schematic diagram showing at least one embodiment of a system that may be used for performing one or multiple imaging modality viewing and control in accordance with one or more aspects of the present disclosure.

As shown diagrammatically in FIG. 1A, one or more embodiments for visualizing, emphasizing and/or controlling one or more imaging modalities and artificial intelligence (such as, but not limited to, machine and/or deep learning, residual learning, using results of marker detection to perform coregistration, etc.) for detecting marker(s) and/or performing coregistration of the present disclosure may be involved with one or more predetermined or desired procedures, such as, but not limited to, medical procedure planning and performance (e.g., PCI as aforementioned). For example, the system 2 may communicate with the image scanner 5 (e.g., a CT scanner, an X-ray machine, etc.) to request information for use in the medical procedure (e.g., PCI) planning and/or performance, such as, but not limited to, bed positions, and the image scanner 5 may send the requested information along with the images to the system 2 once a clinician uses the image scanner 5 to obtain the information via scans of the patient. In some embodiments, one or more angiograms 3 taken concurrently or from an earlier session are provided for further planning and visualization. The system 2 may further communicate with a workstation such as a Picture Archiving and Communication System (PACS) 4 to send and receive images of a patient to facilitate and aid in the medical procedure planning and/or performance. Once the plan is formed, a clinician may use the system 2 along with a medical procedure/imaging device 1 (e.g., an imaging device, an OCT device, an IVUS device, a PCI device, an ablation device, a 3D structure construction or reconstruction device, etc.) to consult a medical procedure chart or plan to understand the shape and/or size of the targeted biological object to undergo the imaging and/or medical procedure. Each of the medical procedure/imaging device 1, the system 2, the locator device 3, the PACS 4 and the scanning device 5 may communicate in any way known to those skilled in the art, including, but not limited to, directly (via a communication network) or indirectly (via one or more of the other devices such as 1 or 5, or additional flush and/or contrast delivery devices; via one or more of the PACS 4 and the system 2; via clinician interaction; etc.).

In medical procedures, improvement or optimization of physiological assessment is preferable to decide a course of treatment for a particular patient. By way of at least one example, physiological assessment is very useful for deciding treatment for cardiovascular disease patients. In a catheterization lab, for example, physiological assessment may be used as a decision-making tool—e.g., whether a patient should undergo a PCI procedure, whether a PCI procedure is successful, etc. While the concept of using physiological assessment is theoretically sound, physiological assessment still waits for more adaption and improvement for use in the clinical setting(s). This situation may be because physiological assessment may involve adding another device and medication to be prepared, and/or because a measurement result may vary between physicians due to technical difficulties. Such approaches add complexities and lack consistency. Therefore, one or more embodiments of the present disclosure may employ CFD-based physiological assessment that may be performed from imaging data to eliminate or minimize technical difficulties, complexities and inconsistencies during the measurement procedure. To obtain accurate physiological assessment, an accurate 3D structure of the vessel may be reconstructed from the imaging data as disclosed in U.S. Provisional Pat. App. No. 62/901,472, filed on Sep. 17, 2019, the disclosure of which is incorporated by reference herein in its entirety.

In at least one embodiment of the present disclosure, a method may be used to provide more accurate 3D structure (s) compared to using only one imaging modality. In one or more embodiments, a combination of multiple imaging modalities may be used, marker(s) may be detected, and coregistration may be processed/performed using artificial intelligence.

One or more embodiments of the present disclosure may apply machine learning, especially deep learning, to detect a marker in an angiography image frame without user input(s) that define an area where intravascular imaging pullback occurs. Using artificial intelligence, for example, deep learning, one or more embodiments of the present disclosure may achieve a better or maximum success rate of marker detection from angiography data without (or with less) user interactions, and may reduce processing and/or prediction time to display coregistration result(s) based on the marker detection result(s).

One or more embodiments of the present disclosure may achieve the efficient marker detection and/or efficient coregistration result(s) by creating a detector to identify and localize a radiopaque marker on intravascular imaging catheter from angiography image. In one or more embodiments, the angiography data may be acquired during intravascular imaging pullback using a catheter having a radiopaque marker that may be visualized in an angiography image. In one or more embodiments, a ground truth identifies a location of the radiopaque marker. In one or more embodiments, a model has enough resolution to predict the marker location in a given image with sufficient accuracy depending on the application or procedure being performed. The performance of the model may be further improved by adding more training data. For example, additional training data may include image annotations, where a user labels or corrects the radiopaque marker in each image. One or more embodiments may use the detector to identify and localize the radiopaque marker(s).

In one or more embodiments, a radiopaque marker may be detected and tracked using an algorithm, such as, but not limited to, the Viterbi algorithm.

One or more embodiments may automate characterization of stenosis in angiography images using convolutional neural networks, and may fully automate frame detection on angiographies using training (e.g., offline training) and using applications (e.g., online application(s)) to extract and process frames via deep learning.

One or more embodiments of the present disclosure may track and/or calculate a radiopaque marker detection success rate.

In at least one further embodiment example, a method of 3D reconstruction without adding any imaging requirements or conditions may be employed. One or more methods of the present disclosure may use intravascular imaging, e.g., IVUS, OCT, etc., and one (1) view of angiography. In the description below, while intravascular imaging of the present disclosure is not limited to OCT, OCT is used as a representative of intravascular imaging for describing one or more features herein.

Figure 1B:
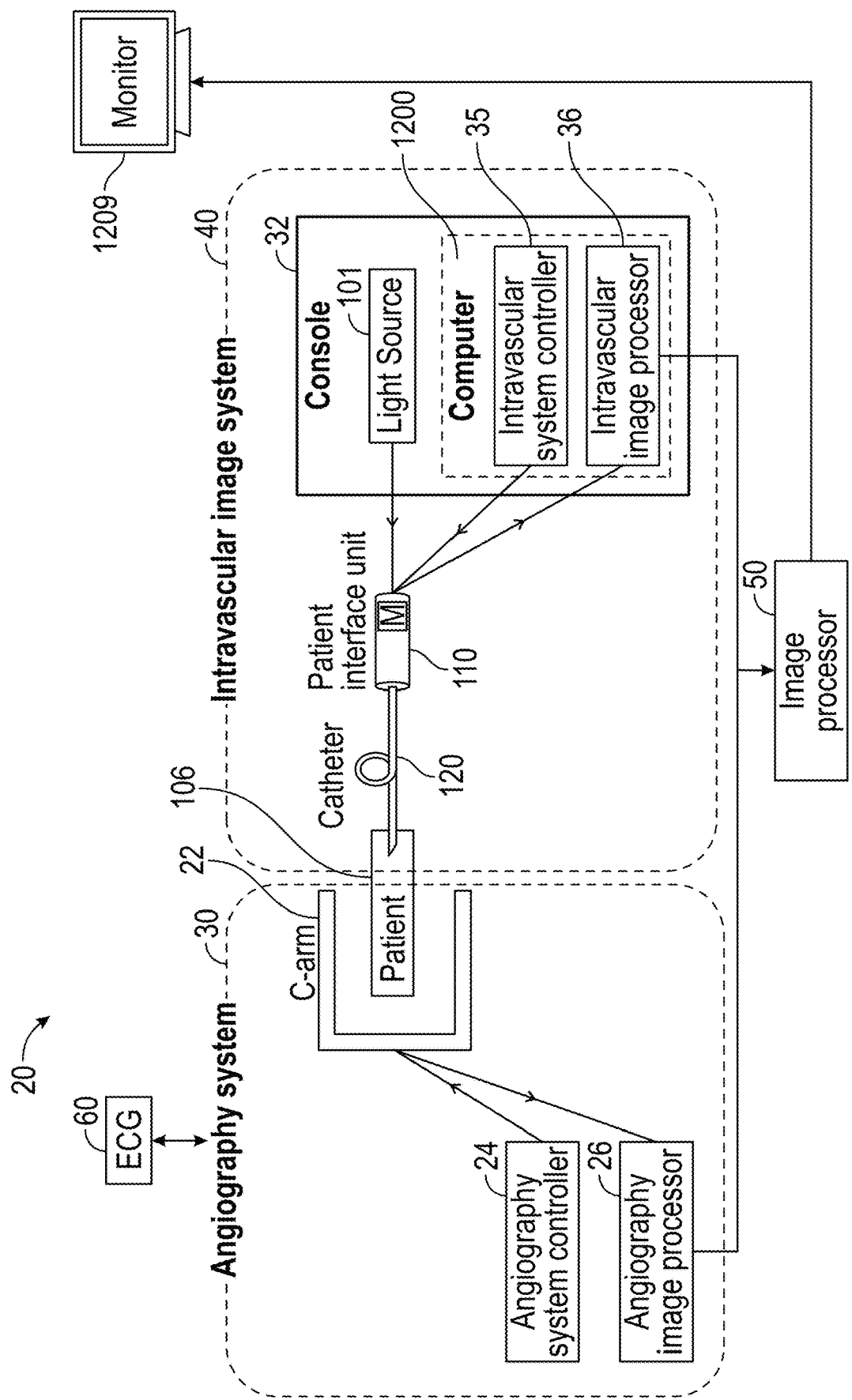
FIG. 1B is a schematic diagram illustrating an imaging system for executing one or more steps to process image data in accordance with one or more aspects of the present disclosure.

Referring now to FIG. 1B, shown is a schematic diagram of at least one embodiment of an imaging system 20 for generating an imaging catheter path based on either a directly detected location of a radiopaque marker on the imaging catheter or a regression line representing the imaging catheter path by using an angiography image frame that is simultaneously acquired during intravascular imaging pullback. The embodiment of FIG. 1B may be used with one or more of the artificial intelligence feature(s) discussed herein. The imaging system 20 may include an angiography system 30, an intravascular imaging system 40, an image processor 50, a display or monitor 1209, and an electrocardiography (ECG) device 60. The angiography system 30 includes an X-ray imaging device such as a C-arm 22 that is connected to an angiography system controller 24 and an angiography image processor 26 for acquiring angiography image frames of an object or patient 106.

The intravascular imaging system 40 of the imaging system 20 may include a console 32, a catheter 120 and a patient interface unit or PIU no that connects between the catheter 120 and the console 32 for acquiring intravascular image frames. The catheter 120 may be inserted into a blood vessel of the patient 106. The catheter 120 may function as a light irradiator and a data collection probe that is disposed in the lumen of a particular blood vessel, such as, for example, a coronary artery. The catheter 120 may include a probe tip, one or more radiopaque markers, an optical fiber, and a torque wire. The probe tip may include one or more data collection systems. The catheter 120 may be threaded in an artery of the patient 106 to obtain images of the coronary artery. The patient interface unit no may include a motor M inside to enable pullback of imaging optics during the acquisition of intravascular image frames. The imaging pullback procedure may obtain images of the blood vessel. The imaging pullback path may represent the co-registration path, which may be a region of interest or a targeted region of the vessel.

The console 32 may include a light source(s) 101 and a computer 1200. The computer 1200 may include features as discussed herein and below (see e.g., FIG. 14, FIG. 16, etc.), or alternatively may be a computer 1200' (see e.g., FIG. 15, FIG. 16, etc.) or any other computer or processor discussed herein. In one or more embodiments, the computer 1200 may include an intravascular system controller 35 and an intravascular image processor 36. The intravascular system controller 35 and/or the intravascular image processor 36 may operate to control the motor M in the patient interface unit 110. The intravascular image processor 36 may also perform various steps for image processing and control the information to be displayed.

Various types of intravascular imaging systems may be used within the imaging system 20. The intravascular imaging system 40 is merely one example of an intravascular imaging system that may be used within the imaging system 20. Various types of intravascular imaging systems may be used, including, but not limited to, an OCT system, a multi-modality OCT system or an IVUS system, by way of example.

The imaging system 20 may also connect to an electrocardiography (ECG) device 60 for recording the electrical activity of the heart over a period of time using electrodes placed on the skin of the patient 106. The imaging system 20 may also include an image processor 40 for receiving angiography data, intravascular imaging data, and data from the ECG device 60 to execute various image-processing steps to transmit to a display 1209 for displaying an angiography image frame with a co-registration path. Although the image processor 40 associated with the imaging system 20 appears external to both the angiography system 20 and the intravascular imaging system 30 in FIG. 1B, the image processor 40 may be included within the angiography system 30, the intravascular imaging system 40, the display 1209 or a stand-alone device. Alternatively, the image processor 40 may not be required if the various image processing steps are executed using one or more of the angiography image processor 26, the intravascular image processor 36 of the imaging system 20, or any other processor discussed herein (e.g., computer 1200, computer 1200', computer or processor 2, etc.).

Figure 2:
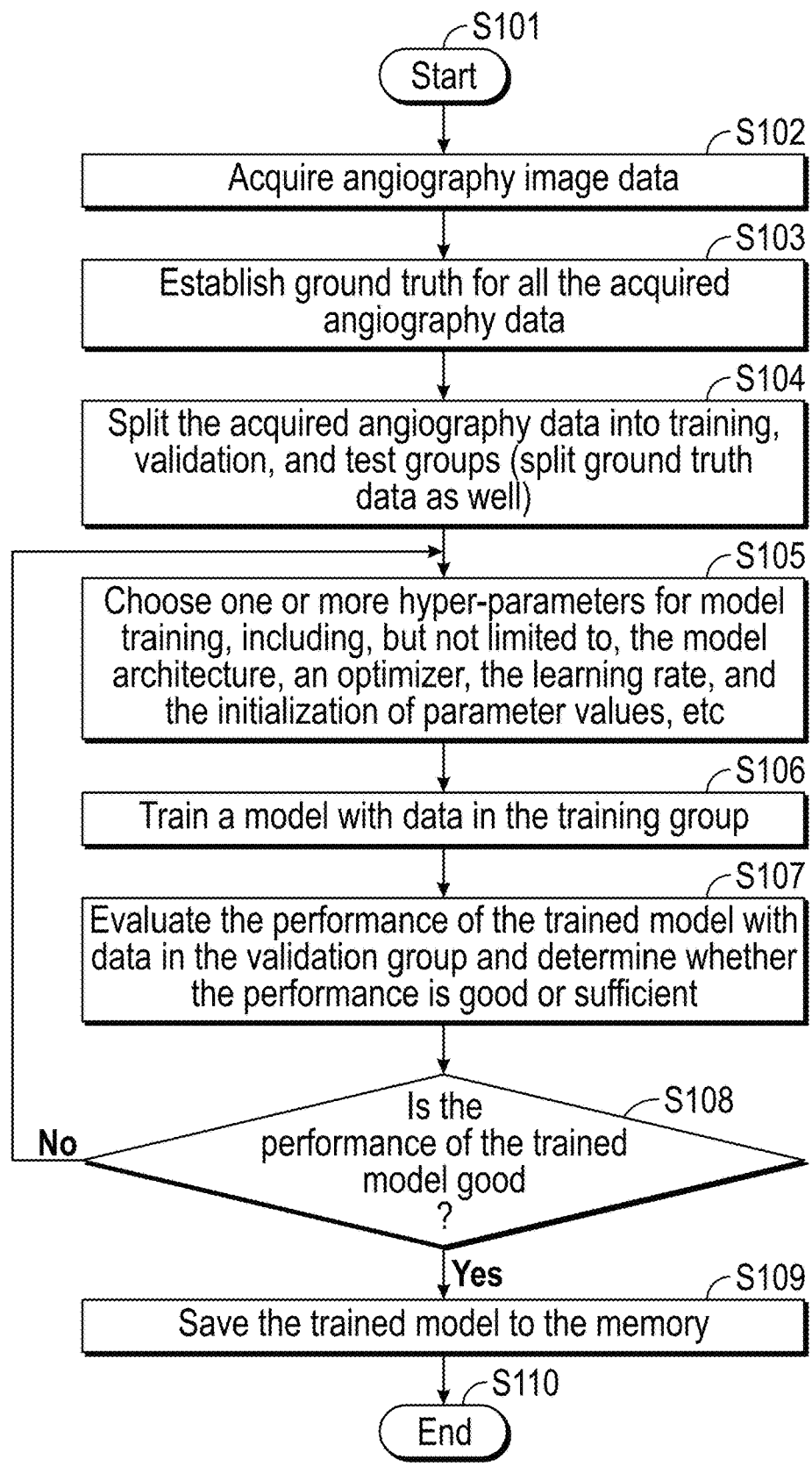
FIG. 2 is a flowchart of at least one embodiment of a method for creating an identifier or detector using trained deep learning that may be used in accordance with one or more aspects of the present disclosure.

FIG. 2 shows at least one embodiment of a method for creating an identifier or detector using trained deep learning that may be used in accordance with one or more aspects of the present disclosure.

Figure 3:
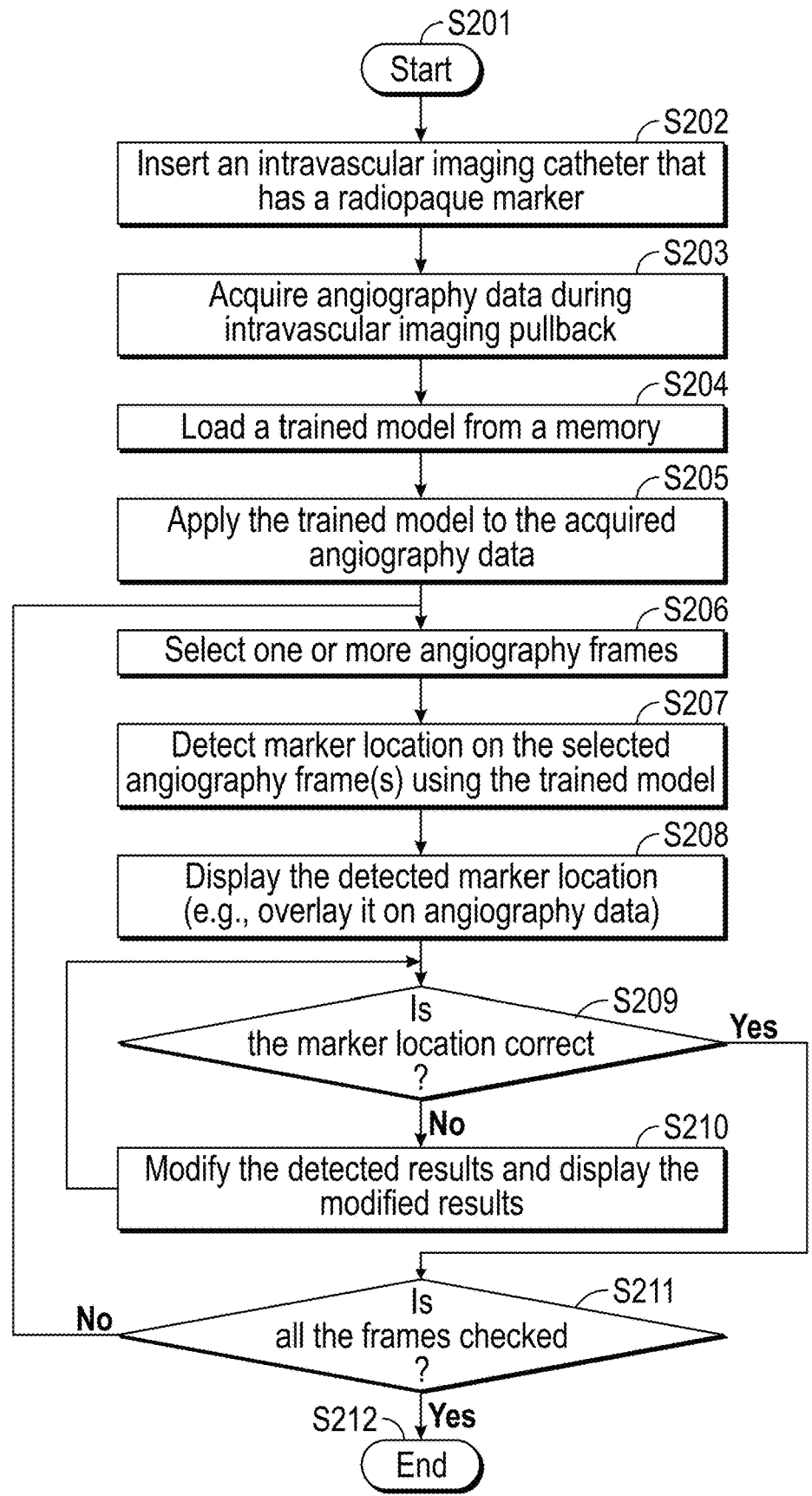
FIG. 3 is a flowchart of at least one embodiment of a method for using an identifier or detector to detect a radiopaque marker that may be used in accordance with one or more aspects of the present disclosure.

FIG. 3 shows at least one embodiment of a method for using an identifier or detector to detect a radiopaque marker that may be used in accordance with one or more aspects of the present disclosure.

Embodiments of a method or methods for creating an identifier or detector and embodiments of using an identifier or detector to detect a marker may be used independently or in combination. While not limited to the discussed combination or arrangement, one or more steps may be involved in both of the workflows or processes in one or more embodiments of the present disclosure, for example, as shown in FIG. 2 and/or FIG. 3 and as discussed below.

One or more embodiments of the present disclosure improve or maximize a marker detection success rate by, for example, improving the method/algorithm for selecting points among or from candidate points, improving the detection method/algorithm that may utilize features that are difficult to capture via other image processing techniques (e.g., via the use of artificial intelligence, via the application of machine or deep learning, via the use of artificial intelligence results to perform coregistration, etc.), etc. In one or more embodiments, at least one artificial intelligence, computer-implemented task may be co-registration of images between images acquired by one or more imaging modalities, where one image is an angiography image that is acquired during intravascular imaging of a sample or object, such as, but not limited to, the coronary arteries, using an OCT probe (pullback of OCT probe upon contrast agent application, for example), and where the other intravascular imaging may be, but is not limited to, IVUS. In one or more embodiments, at least another artificial intelligence, computer-implemented task may be a specific machine learning task: keypoint detection, where the keypoint is a radiopaque marker that has been "introduced" into angiography images to facilitate detection.

Returning to the details of FIG. 2, one or more methods or processes of the present disclosure may include one or more of the following steps (starting at step S101 in FIG. 2): (i) acquiring angiography image data (see step S102 in FIG. 2); (ii) establishing a ground truth for the marker location in acquired angiography data/images (see step S103 in FIG. 2); (iii) splitting the acquired angiography data/image set (examples of images and/or corresponding ground truths) into training, validation, and test groups or sets (see step S104 in FIG. 2); (iv) choosing the hyper-parameters for model training, including, but not limited to, the model architecture, the learning rate, and the initialization of parameter values (see step S105 in FIG. 2); (v) training a model with data in the training group or training set and evaluating it with data in the validation group or validation set (see step S106 in FIG. 2); (vi) determining whether the performance of the trained model is good or sufficient (see step S107 in FIG. 2); (vii) in the event that step S107 results in a "No", then return to before step S105 and repeat steps S105-S106, or in the event that step S107 results in a "Yes", then proceed to step S108; (viii) estimating a generalization error of the trained model with data in the test group or test set (see step S108 in FIG. 2); and (ix) saving the trained model to a memory (see step S109 in FIG. 2) (and then ending the process at step S110 in FIG. 2). The steps shown in FIG. 2 may be performed in any logical sequence and may be omitted in parts in one or more embodiments. In one or more embodiments, step S109 may involve saving the trained model to the memory or a disk, and may automatically save the trained model or may prompt a user (one or more times) to save the trained model. In one or more embodiments, a model may be selected based on its performance on the validation set, and the generalization error may be estimated on the test using the selected model. In one or more embodiments, an apparatus, system, method, or storage medium may have multiple models to be saved, which have already been trained previously, and the apparatus, system, method, or storage medium may select a model for further training based on a previous or prior success rate. In one or more embodiments, any trained model works for any angio apparatus or system with a same or similar success rate; in a situation where more data exists from different angio apparatuses or systems, one model may work better for a certain angio apparatus or system whereas another model may work better for a different angio apparatus or system. In this scenario, one or more embodiments may create test or validation data set(s) for specific angio apparatus(es) or system(s), and may identify which model works best for a specific angio apparatus(es) or system(s) with the test set(s) and/or validation set(s).

While an intravascular image and an angiography image may be acquired simultaneously in one or more embodiments, such image acquisition may be performed at different times (or not being simultaneously acquired) in one or more other embodiments, such as, but not limited to, embodiment(s) as discussed in U.S. Pat. App. No. 62/798,885, filed on Jan. 30, 2019, the application of which is incorporated by reference herein in its entirety. Indeed, co-registration may be performed under either scenario. In one or more embodiments where an angiography image is acquired simultaneously with an intravascular image, the one or more such embodiments may increase the accuracy of the co-registration because a radiopaque marker location, which is the acquisition location of an intravascular (e.g., OCT) image, may be detected. In one or more embodiments, OCT/IVUS and angiography modalities are available when using images that are acquired during a procedure (e.g., a PCI procedure). In one or more embodiments, where a CT image is acquired prior to the PCI procedure, co-registration between CT and angiography, and/or between CT and OCT/IVUS, may be performed. Using CT and OCT/IVUS is further discussed in U.S. Pat. Pub. No. 2018/0271614, which publication is incorporated by reference herein in its entirety. While one or more PCI procedures discussed herein discusses stent implantation, balloon angioplasty or other procedures in coronary arteries and other arteries (e.g., arteries located in one or more legs or other body parts), PCT procedures are not limited thereto. For example, in addition to uses for coronary procedures, OCT/IVUS may be used in other region(s) of vasculature. In one or more embodiments, the angiography image(s) obtained in step S102 may be used for an initial analysis of a patent or the case, and/or may be used for co-registration. The angiography image(s) may be obtained during OCT pullback to achieve more accurate co-registration, or may be received from a memory or database as further discussed below.

In step S103 discussed above, establishing ground truth may be performed in one or more ways for one or more architectural models for the artificial intelligence methods or algorithms discussed herein. In one or more embodiments, a ground truth may be locations of two endpoints of the major axis of the target marker in each angiography frame captured during OCT pullback. While architectural models discussed herein focus on a segmentation model, an object model (also referred to as a "regression model", a regression model with residual learning, and a model that combines one or more features of the segmentation model and the regression model, the architectural models are not limited thereto. For the segmentation model, ground truth may involve a mask image that contains the line that connects these two locations with a certain width as a positive area (see e.g., FIG. 6A discussed further below). In one or more embodiments were a target marker may not be distinguishable yet from other markers, all of the markers may be marked as ground truth. In one or more embodiments where more data exists for training and/or a time series of frames (e.g., a video sequence) is utilized, a model may be improved to train a model with ground truth that includes only the target marker being masked. In one or more embodiments for a regression model or object model, a centroid of two edge locations may be considered as the ground truth location of a target marker in each image. In one or more embodiments, ground truth may be established, for example, by an expert graphically annotating the two marker locations in each frame of an angiographic image.

In step S104, splitting the acquired angiography data set (examples of images and/or corresponding ground truths) into training, validation, and test sets or groups may occur in one or more ways for the artificial intelligence methods or algorithms discussed herein. While several examples of splitting data are discussed herein, the methods and algorithms are not limited thereto. By way of at least one embodiment example, input data may be split into training (70%), validation (15%), and test (15%) data sets or groups. The data splitting may be performed randomly (e.g., on a pullback-basis, on a frame-basis, etc.). In one or more embodiments, the data set may be split such that the training, validation, and test sets or groups are maximally de-correlated and the examples in each set or group may be sampled from different image acquisition procedure(s). For example, in one or more embodiments where a final application may process or seek to process a new pullback example, all images in the validation and test sets or groups may be sampled from pullbacks that have not been part of the training set or group and not been used for model training. Different kinds of data may be used for the data split. In situations where there were limited availability of data from clinical studies for model training, data from animal studies may be included in the training set or group. In at least one embodiment, the training set or group may be primarily composed of examples obtained as part of an animal study or animal studies, whereas the validation and test sets or groups may be primarily or only composed of examples obtained during clinical studies. In one or more embodiments, different combinations of data from animal studies and/or clinical studies may be used for one or more of the following: the training set(s) or group(s), the validation set(s) or group(s), and/or the test set(s) or group(s). Usage of animal data in training may enable adding the data that is acquired in rare clinical situation(s), and, in one or more embodiments, may, therefore, be applicable in clinical setting(s). Once more clinical data is available, one or more embodiments may use the clinical data (e.g., without animal data) for all data subsets. One or more embodiments may employ potential additional training data. For example, if a radiopaque marker in angio images that are acquired during a stent or balloon catheter delivery looks similar to the marker in an OCT catheter, one or more embodiments may include examples of stent or balloon catheter angio data/images and corresponding ground truths in form of user-annotated radiopaque marker locations into the training set(s) and use these examples to train a model to detect the marker in an OCT catheter. Similarly, in one or more embodiments, any other angio images of a catheter/probe with a radiopaque marker that looks similar to that on or of an OCT catheter may be used as additional training data. Preferably, one or more embodiments employs data quality control. For example, selection of training samples may be performed manually in one or more embodiments. If a human may identify the radiopaque marker (the target for detection) by eye, such a sample may be a good data point for training. For testing, any angio image that is captured during OCT pullback may be used as long as a ground truth may be established by a human expert reader or clinician. One or more embodiments may involve image pre-processing. Since a range of image contrast is different between frames/pullbacks, normalization of image pixel values or other image transformations may be performed as a pre-processing step. Normalization may be performed for each individual angio frame before training starts or for each batch of angio frames that are passed to the model for each training iteration.

In step S105, choosing the hyper-parameters for model training, including the model architecture, the learning rate, and initialization of parameter values may vary depending on a predetermined or desired objective and/or application(s). For example, the choice of a model architecture may depend on a success rate of coregistration (which may be affected by a marker detection success rate) in the setting of a final application on validation and/or test data set(s). Such consideration(s) may be balanced with time (e.g., a predetermined time period, a desired time period, an available time period, a target time period, etc.) for processing/predicting and user interaction. In one or more embodiments, a success rate or rates of coregistration and/or marker detection is/are evaluated with a pre-determined metric, such as, but not limited to, a root mean squared error between the prediction and the actual location. In one or more embodiments, a model architecture may be selected depending on an input and an output. For example, in the segmentation or semantic segmentation model (also referred to as the classification model), an input may be an individual angio frame, and the output may be a segmented/masked image, for example, where foreground pixels demarcating a marker area have positive values and background pixels have zero values. The segmentation (classification) model may apply post-processing after obtaining the segmented/masked image to determine coordinate points of the marker location, which may affect the success rate of the marker detection and ultimately may affect the success rate of the coregistration. By way of another example, in the object detection (regression) model, an input may be an individual angio frame, and an output may be a coordinate of the marker location (e.g., only the target marker). By way of a further example, a combined architectural model may use a combination of the aforementioned inputs and outputs.

While not limited to this process or steps thereof, using a detector to detect (or identify and localize) a radiopaque marker may be performed, for example, as shown in FIG. 3. For example, one or more methods or processes of the present disclosure may include one or more of the following steps (starting at step S201 in FIG. 3): (i) inserting (e.g., into a vessel, a target specimen or object, into a patient, etc.) an intravascular imaging catheter that has a radiopaque marker (see step S202 in FIG. 3); (ii) acquiring angiography data during intravascular pullback (see step S203 in FIG. 3); (iii) loading a trained model from a memory (which, for example, may be one or more of the memories discussed herein) (see step S204 in FIG. 3); (iv) applying the trained model to the acquired angiography data (see step S205 in FIG. 3); (v) selecting one angiography frame (see step S206 in FIG. 3); (vi) detecting marker location on the selected angiography frame with the trained model (see step S207 in FIG. 3); (vii) displaying the detected marker location (e.g., overlay the detected marker location on angiography data) (see step S208 in FIG. 3); (viii) check whether the marker location is correct or accurate (see step S209 in FIG. 3); (ix) in the event that step S209 results in a "No", then modifying the detected results, displaying the modified results (see step S210 in FIG. 3) and returning to step S209 to determine whether the marker location is correct (e.g., in the modified results), or in the event that step S209 results in a "Yes", then check whether all frames have been checked (see step S211 in FIG. 3); and (x) in the event that step S211 results in a "No", then returning to before step S206 and repeat steps S206 through S211 (e.g., for each additional frame in the set of frames, for each additional frame that remain to be checked, for an additional frame that has not been checked yet, etc.), or, in the event that step S211 results in a "Yes", then end the process (see step S212 in FIG. 3). The steps shown in FIG. 3 may be performed in any logical sequence and may be omitted in parts in one or more embodiments.

Figure 4:
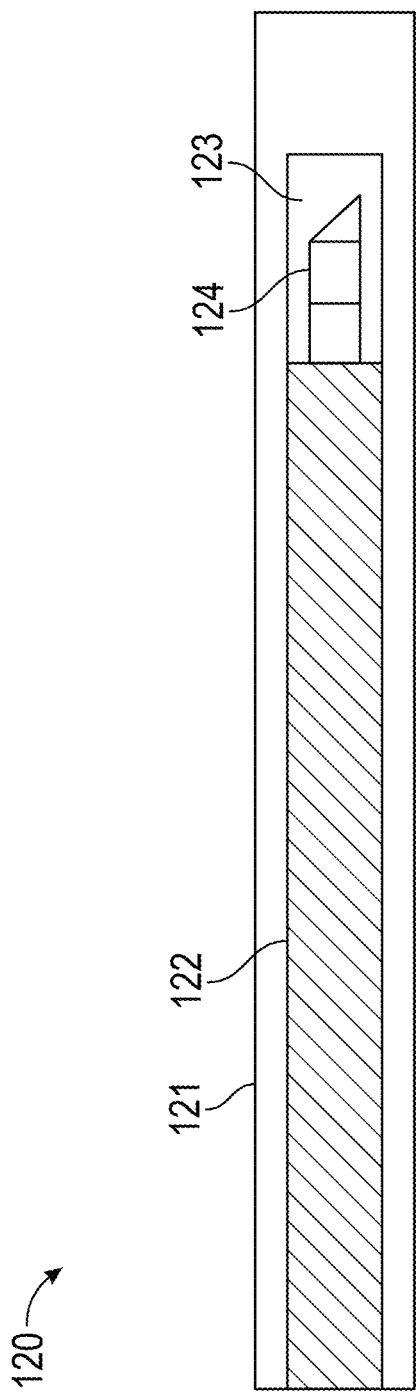
FIG. 4 is a diagram of at least one embodiment of a catheter that may be used with one or more embodiments for detecting a marker and/or performing coregistration in accordance with one or more aspects of the present disclosure.

FIG. 4 shows at least one embodiment of a catheter 120 that may be used in one or more embodiments of the present disclosure for obtaining images; for using and/or controlling multiple imaging modalities, that apply machine learning, especially deep learning, to identify a marker in an angiography image frame with greater or maximum success; and for using the results to perform coregistration more efficiently or with maximum efficiency. FIG. 4 shows an embodiment of the catheter 120 including a sheath 121, a coil 122, a protector 123 and an optical probe 124. As shown schematically in FIGS. 12A-12C (discussed further below), the catheter 120 may be connected to a patient interface unit (PIU) 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of the object (e.g., a biological organ, sample or material being evaluated, such as, but not limited to, hollow organs such as vessels, a heart, a coronary artery, etc.). For example, fiber optic catheters and endoscopes may reside in the sample arm (such as the sample arm 103 as shown in one or more of FIGS. 12A-12C discussed below) of an OCT interferometer in order to provide access to internal organs, such as intravascular images, gastro-intestinal tract or any other narrow area, that are difficult to access. As the beam of light through the optical probe 124 inside of the catheter 120 or endoscope is rotated across the surface of interest, cross-sectional images of one or more objects are obtained. In order to acquire imaging data or three-dimensional data, the optical probe 124 is simultaneously translated longitudinally during the rotational spin resulting in a helical scanning pattern. This translation is most commonly performed by pulling the tip of the probe 124 back towards the proximal end and therefore referred to as a pullback.

The catheter 120, which, in one or more embodiments, comprises the sheath 121, the coil 122, the protector 123 and the optical probe 124 as aforementioned (and as shown in FIG. 4), may be connected to the PIU 110. In one or more embodiments, the optical probe 124 may comprise an optical fiber connector, an optical fiber and a distal lens. The optical fiber connector may be used to engage with the PIU 110. The optical fiber may operate to deliver light to the distal lens. The distal lens may operate to shape the optical beam and to illuminate light to the object (e.g., the object 106 (e.g., a vessel) discussed herein), and to collect light from the sample (e.g., the object 106 (e.g., a vessel) discussed herein) efficiently.

As aforementioned, in one or more embodiments, the coil 122 delivers torque from a proximal end to a distal end thereof (e.g., via or by a rotational motor in the PIU no). There may be a mirror at the distal end so that the light beam is deflected outward. In one or more embodiments, the coil 122 is fixed with/to the optical probe 124 so that a distal tip of the optical probe 124 also spins to see an omnidirectional view of an object (e.g., a biological organ, sample or material being evaluated, such as, but not limited to, hollow organs such as vessels, a heart, a coronary artery, etc.). In one or more embodiments, the optical probe 124 may include a fiber connector at a proximal end, a double clad fiber and a lens at distal end. The fiber connector operates to be connected with the PIU 110. The double clad fiber may operate to transmit & collect OCT light through the core and, in one or more embodiments, to collect Raman and/or fluorescence from an object (e.g., the object 106 (e.g., a vessel) discussed herein, an object and/or a patient (e.g., a vessel in the patient), etc.) through the clad. The lens may be used for focusing and collecting light to and/or from the object (e.g., the object 106 (e.g., a vessel) discussed herein). In one or more embodiments, the scattered light through the clad is relatively higher than that through the core because the size of the core is much smaller than the size of the clad.

As discussed above, selecting a model (segmentation model (classification model), object or keypoint detection model (regression model), or a combination thereof) may depend on a success rate of coregistration, which may be affected by a marker detection success rate, in the setting of a final application on validation and/or test data set(s). Such consideration(s) may be balanced with time (e.g., a predetermined time period, a desired time period, an available time period, a target time period, etc.) for processing/predicting and user interaction. Because there are many factors to consider when choosing a model, such as, but not limited to, the marker detection success rate and/or coregistration success rate, etc., and because success rates may vary from method to method depending on the conditions for such methods, examples of different marker detection success rate are shown in FIG. 5. While marker detection success rate may be calculate in various ways, one example of a marker detection success rate is to calculate the number of frames for which the predicted and the true radiopaque marker locations are considered the same (e.g., when the distance between predicted and true marker positions is within a certain tolerance or below a pre-defined distance threshold, which is defined by a user or pre-defined in the system (e.g., the distance threshold may be set at 1.0 mm); etc.) divided by the total number of frames obtained, received, or imaged during the OCT pullback. According to a first method where a user specifies a pullback region on one frame, according to a second method where a user points out marker location on several or multiple frames, and according to a third method where a user specifies a pullback region on multiple frames, several success rates are shown for three categories of data in FIG. 5 to highlight success rate variation(s). Additionally, coregistration success rates (based on user interviews) may be successful in 80% of cases or higher. Experiments revealed that candidate points (predicted segments) intersect with the true marker location in at least 80-90% of total clinical angiography images using one or more features of the present disclosure. By applying machine or deep learning as discussed herein, marker detection success rates and coregistration success rates may be improved or maximized. The success rate of marker detection (and consequently the success rate of coregistration) may depend on how good the prediction of a marker location is across all frames. As such, by improving estimation of the marker location, the success rate of the marker detection may be improved and likewise the success rate of coregistration may be improved.

For the segmentation model (also referred to as classification model or a semantic segmentation model) architecture, one or more certain area(s) of an image are predicted to belong to one or more classes in one or more embodiments. There are many different segmentation model architectures or ways to formulate or frame the image segmentation task or issue. By way of at least one example, a segmentation may involve classifying a given area or region within an image into one of two classes (foreground and background). By way of a non-limiting, non-exhaustive embodiment example, the two classes may indicate whether a target (e.g., a pixel, an area of an image, a target object in an image, etc.) represents a radiopaque marker (first class, foreground, etc.) or does not represent a marker (second class, background, etc.). In one or more output examples, each pixel may be classified into either representing a marker or not representing a marker. One or more embodiments of a semantic segmentation model may be performed using the One-Hundred Layers Tiramisu method discussed in "The One Hundred Layers Tiramisu: Fully Convolutional DenseNets for Semantic Segmentation" to Simon Jégou, et al., Montreal Institute for Learning Algorithms, published Oct. 31, 2017 (https://arxiv.org/pdf/1611.09326.pdf), which is incorporated by reference herein in its entirety. Convolutional Neural Networks (CNNs) may be used for one or more features of the present invention, including, but not limited to, artificial intelligence feature(s), detecting one or more markers, using the marker detection results to perform coregistration, image classification, semantic image segmentation, etc. For example, while other architectures may be employed, one or more embodiments may combine U-net, ResNet, and DenseNet architectural components to perform segmentation. U-net is a popular convolutional neural network architecture for image segmentation, ResNet improves training deep convolutional neural network models due to its skip connections, and DenseNet has reliable and good feature extractors because of its compact internal representations and reduced feature redundancy. In one or more embodiments, a network may be trained by slicing the training data set, and not down-sampling the data (in other words, image resolution may be preserved or maintained). As aforementioned, FIG. 6A shows an example ground truth for a segmentation model, which may be an output in one or more embodiments of a semantic segmentation model. Turning to the details of FIG. 6B, at least one embodiment may utilize an input 600 as shown to obtain an output 605 (e.g., as shown in FIG. 6A, FIG. 6B, etc.) of at least one embodiment of a segmentation model method. For example, by applying the One-Hundred Layers Tiramisu method(s) as aforementioned, one or more features, such as, but not limited to, convolution 601, concatenation 603, transition up 605, transition down 604, dense block 602, etc., may be employed by slicing the training data set. While not limited to only or by only these embodiment examples, in one or more embodiments, a slicing size may be one or more of the following: 100×100, 224×224, 512×512, and, in one or more of the experiments performed, a slicing size of 224×224 performed the best. A batch size (of images in a batch) may be one or more of the following: 2, 4, 8, 16, and, from the one or more experiments performed, a bigger batch size typically performs better (e.g., with greater accuracy). In one or more embodiments, 16 images/batch may be used. The optimization of all of these hyper-parameters depends on the size of the available data set as well as the available computer/computing resources; thus, once more data is available, different hyper-parameter values may be chosen. Additionally, in one or more embodiments, steps/epoch may be 100, and the epochs may be greater than (>) 1000. In one or more embodiments, an evaluation term may be categorical_crossentropy. In one or more embodiments, a convolutional autoencoder (CAE) may be used.

In addition to detection of the marker location, a segmentation model may be used to demarcate regions of interest in an image representing a blood vessel. Since we know that the marker is located inside a vessel (intravascular OCT imaging probe), demarcation of vessels can be used to improve the accuracy and precision of marker detection. Vessel and marker regions may be simultaneously predicted by a segmentation model, which predicts at least three classes: 1) vessel, 2) marker and 3) non-vessel, non-marker. Alternatively, a segmentation model may be used to predict at least two classes: 1) vessel and 2) non-vessel. Additional classes may be used to distinguish between different vessel branches. The predictions of a segmentation model (labeled or masked images) that demarcates vessels may be used to improve training or evaluation of an object/keypoint detection model that predicts the marker location by incorporating the segmentation results into the loss function or evaluation function used to train or evaluate the object detection model, respectively. In this case, segmentation and object detection model may be trained jointly or separately. In addition, segmentation may only be performed for a subset of frames and may only be performed during training and evaluation of the object detection model, but not necessarily upon model inference.

Figure 7:
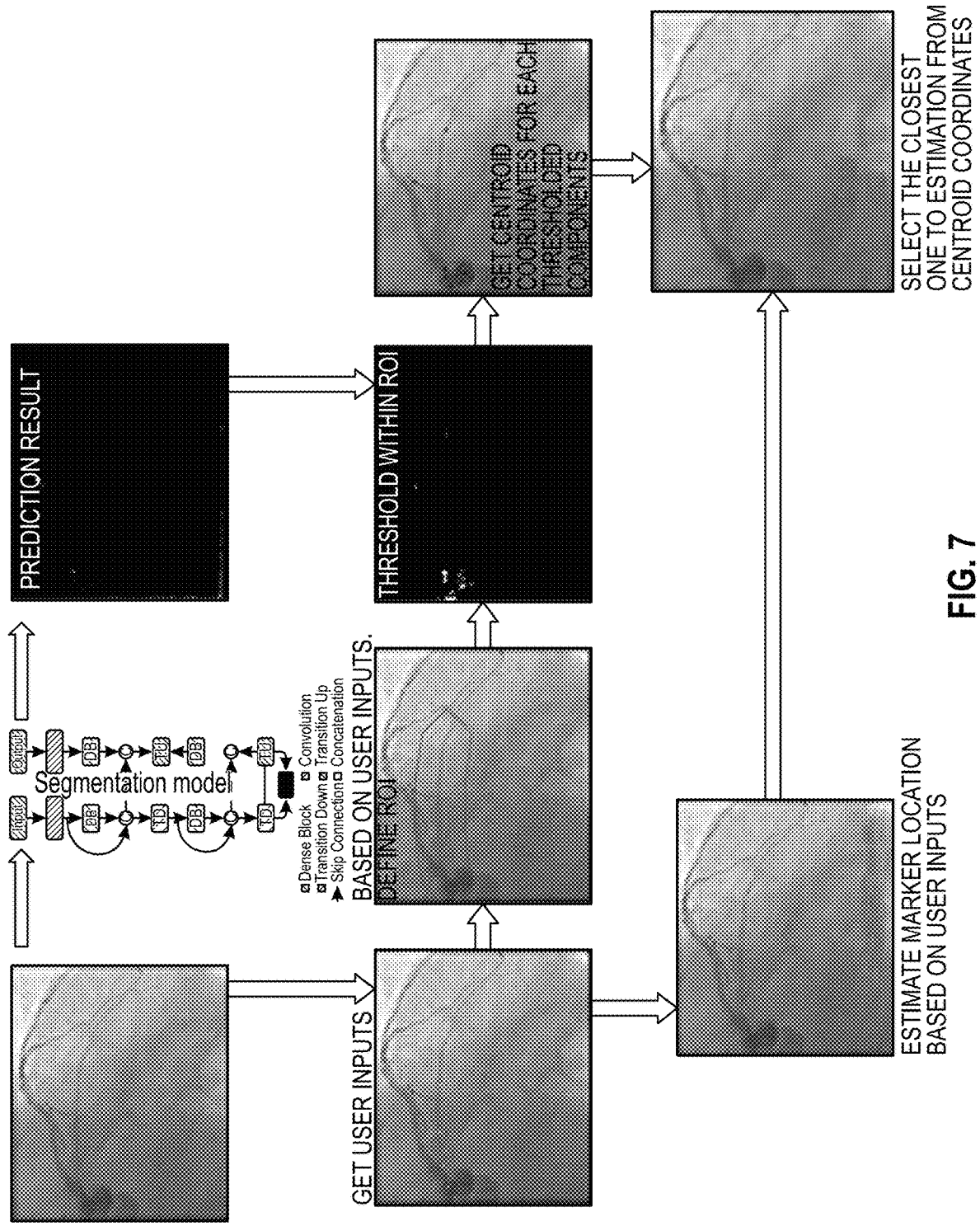
FIG. 7 is an example of at least one embodiment of post-processing, after applying a segmentation model embodiment, that may be used to identify final coordinate(s) in accordance with one or more aspects of the present disclosure.

FIG. 7 shows at least one embodiment of post-processing, after applying a segmentation model embodiment, that may be used to identify final coordinate(s) in accordance with one or more aspects of the present disclosure. For example, a post-processing algorithm or method may include one or more of the following (best seen in FIG. 7): getting user inputs; based on the user inputs, define a region of interest (ROI); estimate a marker location based on the user inputs; determine, establish or set a threshold within the ROI; get centroid coordinates for each thresholded components; and selecting a centroid coordinate from the centroid coordinates, the selected centroid coordinate being closest to the estimation of the marker location based on the user inputs.

Figure 8:
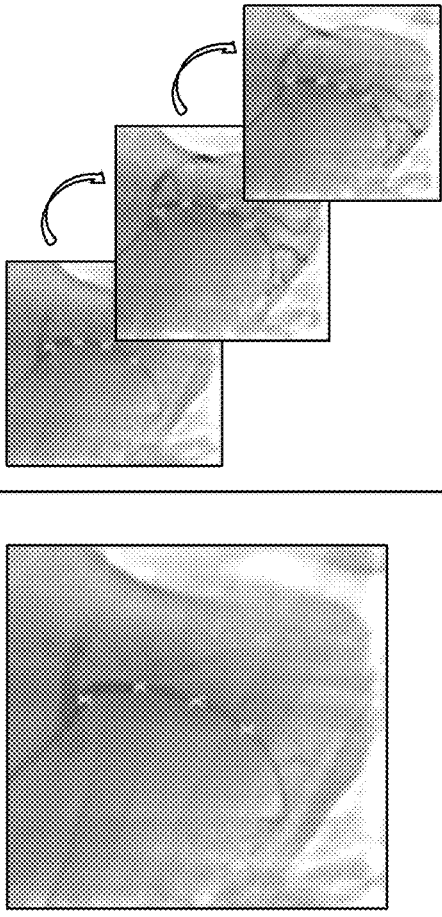
FIG. 8 is a diagram showing several examples of measuring marker detection success rate, including at least one embodiment example of a segmentation model with post-processing, in accordance with one or more aspects of the present disclosure.

FIG. 8 is a diagram showing several examples of measuring marker detection success rate, including at least one embodiment example of a segmentation model with post-processing, in accordance with one or more aspects of the present disclosure. As shown on the left side of FIG. 8, a segmentation model being used with post-processing may increase the success rate substantially compared with other image processing methods in one or more embodiments. For example, the success rate for the segmentation model with post-processing in FIG. 8 was obtained using segmentation model training with only animal data (20 pullbacks, ~60 frames/pullback). Batch size used was 16, training image size used was 224 pixel×224 pixel, steps/iteration used was 200, and iteration used was 5000. In one or more embodiments, the iterations may be limited based on memory size resources available or processing preferences (e.g., a preferred timeline for completed processing, a success rate threshold, etc.). For example, while the iterations used was set to 5000, the success rate obtained with post-processing used training that was terminated at the $4,923^{rd}$ iteration. Test data for all three methods shown in FIG. 8 was all clinical data (45 pullbacks, ~30 frames/pullback).

In one or more embodiments, the segmentation model with post-processing may be used with one or more features from "The One Hundred Layers Tiramisu: Fully Convolutional DenseNets for Semantic Segmentation" to Simon Jégou, et al., Montreal Institute for Learning Algorithms, published Oct. 31, 2017 (https://arxiv.org/pdf/1611.09326.pdf), which is incorporated by reference herein in its entirety.

For the object detection model (also referred to as the regression model or keypoint detection model as aforementioned) architecture, one or more embodiments may use an angio image or images as an input and may predict the marker location in a form of a spatial coordinate. This approach/architecture has advantages over semantic segmentation because the object detection model predicts the marker location directly, and may avoid post-processing in one or more embodiments. The object detection model architecture may be created or built by using or combining convolutional layers, max-pooling layers, fully-connected dense layers, and/or multi-scale image or feature pyramids. Different combinations may be used to determine the best performance test result. The performance test result(s) may be compared with other model architecture test results to determine which architecture to use for a given application or applications.

One or more embodiments of architecture model(s) discussed herein may be used with one or more of: a neural network(s), a convolutional neural network(s), and a random forest.

While experiments were conducted using the following two example architectures, the subject examples are not limiting, and other architectures may be employed (other methods are being tested as well). The first example architecture used is discussed in "Focal Loss for Dense Object Detection" to Tsung-Yi Lin, et al., Facebook AI Research (FAIR), February 2018 (https://arxiv.org/pdf/1708.02002.pdf), which is incorporated by reference herein in its entirety. The second example architecture used is discussed in "Mask R-CNN" to Kaiming He, et al., Facebook AI Research (FAIR), Jan. 24, 2018 (https://arxiv.org/pdf/1703.06870.pdf), which is incorporated by reference herein in its entirety. One or more features from either of the "Focal Loss for Dense Object Detection" to Tsung-Yi Lin, et al. reference or the "Mask R-CNN" to Kaiming He, et al. reference may be used with any other architecture model discussed herein (e.g., semantic segmentation, a combination of semantic segmentation and object detection/regression, regression with residual learning, etc.).

Figure 9A:
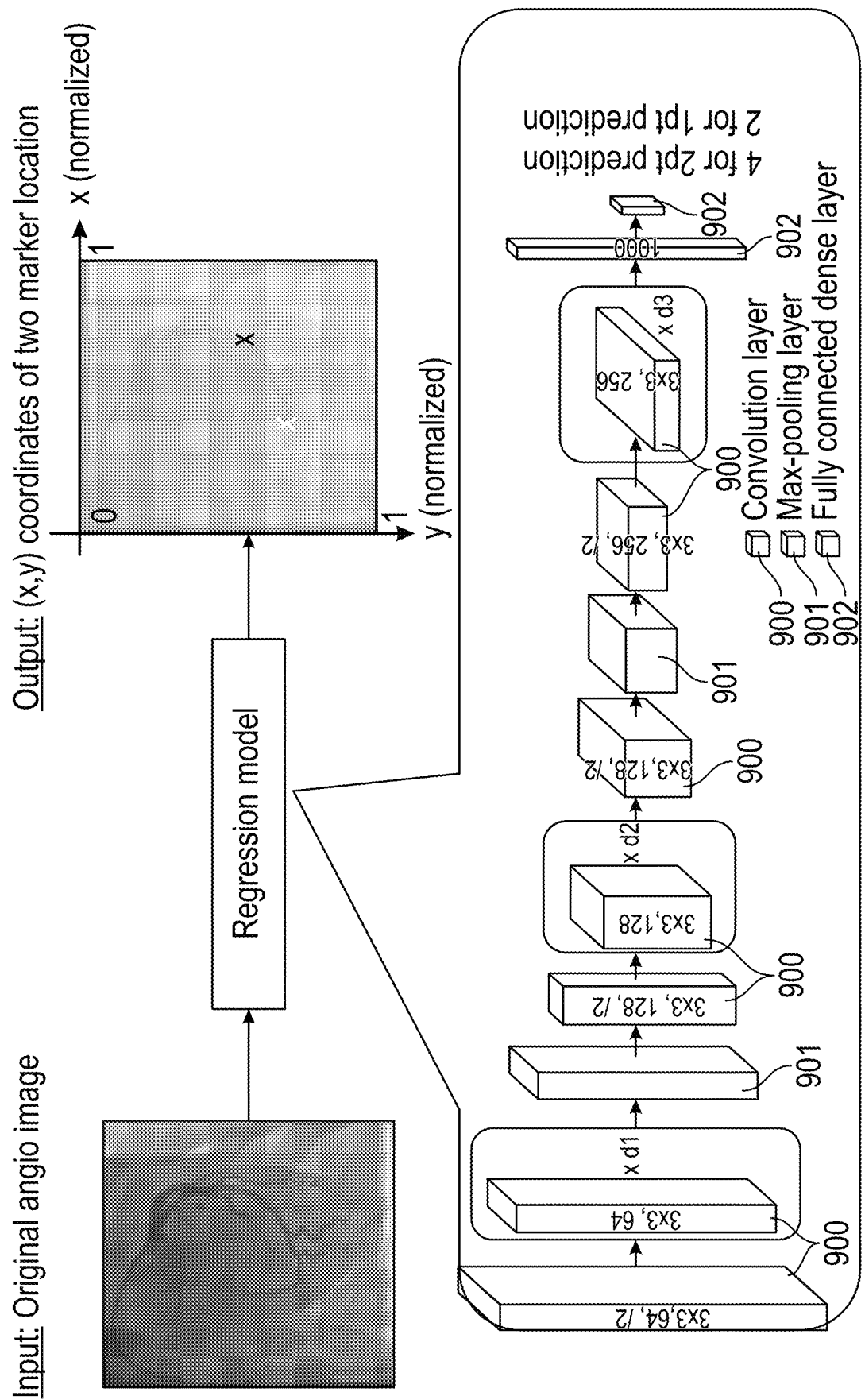
FIG. 9A is a diagram of at least one embodiment example of an object detection model architecture using regression in accordance with one or more aspects of the present disclosure.

Turning now to the details of FIG. 9A, at least one embodiment example of an object detection model architecture using regression is shown in accordance with one or more aspects of the present disclosure. In at least the embodiment of FIG. 9A, the regression model uses a combination of one or more convolution layers 900, one or more max-pooling layers 901, and one or more fully connected dense layers 902. While not limited to the Kernel size, Width/Number of filters (output size), and Stride sizes shown for each layer (e.g., in the left convolution layer of FIG. 9A, the Kernel size is "3×3", the Width/# of filters (output size) is "64", and the Stride size is "2"). Conducted experiments involved a depth (or total number) of about 4-20 convolutional layers. In one or more embodiments, an object detection model may be used with 10 or less than 10 convolution layers. In at least one embodiment, and while not limited to this example, preferably less than 10 convolution layers are used. The optimal number of layers also depends on the size of the available data sets; thus, if more data is available, larger number of layers may be optimal in one or more embodiments. Conducted experiments involved a batch size of about 4-16. In one or more embodiments, a batch size of 12 may be used (while not limited to this example, preferably a batch size of 12 may be used in one or more embodiments depending on the processing, imaging, application(s), etc. involved). The Stride controls how a filter convolves around an input or input volume. For example, a filter may convolve around an input volume by shifting a unit at a time. Stride size defines an amount by which the filter shifts. In a case, for example, where Stride size is "2", a filter may convolve around an input volume by shifting two units at a time. Conducted experiments involved a width (number of filters in each image) of one of: 16, 32, 64, and 128. In one or more embodiments, a width of 64 may be used (while not limited to this example, preferably a width of 64 may be used in one or more embodiments depending on the processing, imaging, application(s), etc. involved). Conducted experiments involved a learning rate in the range of $10^{-1}$-$10^{-8}$. In one or more embodiments, a learning rate of $10^{-5}$ may be used (while not limited to this example, preferably a learning rate of $10^{-5}$ may be used in one or more embodiments depending on the processing, imaging, application(s), etc. involved). Conducted experiments involved a dropout value in the range of $10^{-1}$-$10^{-3}$. In one or more embodiments, a dropout value on the order of $10^{-2}$ may be used (while not limited to this example, preferably a dropout value of $10^{-2}$ may be used in one or more embodiments depending on the processing, imaging, application(s), etc. involved). In one or more embodiments, an optimizer, such as, but not limited to, Stochastic Gradient Descent (SGD), Adaptive Moment Estimation (Adam), etc., may be used. One or more evaluation term(s) may be used, such as, but not limited to, Root Mean Square Error (RMSE) (see e.g., FIGS. 10-11 discussed below). Steps/epoch may be 10, and the number of epochs may be >500 in one or more embodiments.

One or more embodiments may use convolutional neural network architectures with residual connections as discussed in "Deep Residual Learning for Image Recognition" by Kaiming He, et al., Microsoft Research, Dec. 10, 2015 (https://arxiv.org/pdf/1512.03385.pdf), which is incorporated by reference herein in its entirety.

In one or more embodiments, a different neural network architecture may be used, for example, and may be very different from the architecture shown in FIG. 9A. For example, one or more embodiment examples of a neural network architecture may use feature pyramids as described in "Feature Pyramid Networks for Object Detection" by Tsung-Yi Lin, et al., Facebook AI Research (FAIR), Apr. 19, 2017 (https://arxiv.org/abs/1612.03144). Again, the machine learning algorithm or model architecture is not limited to the structures or details discussed herein.

Figure 9B:
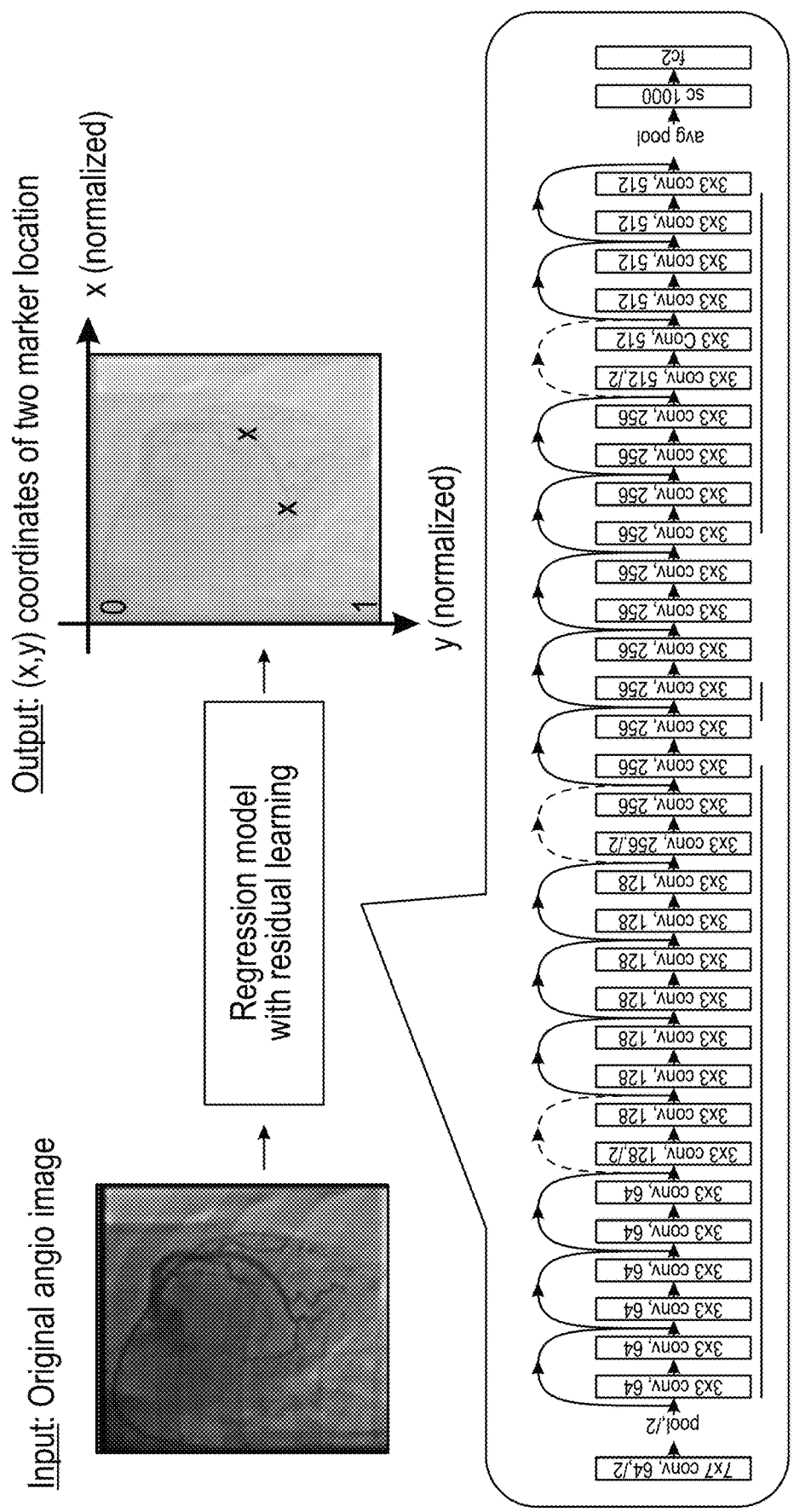
FIG. 9B is a diagram of at least one embodiment example of an object detection model architecture using regression with residual learning in accordance with one or more aspects of the present disclosure.

Turning now to the details of FIG. 9B, at least one embodiment example of an object detection model architecture using regression with residual learning is shown in accordance with one or more aspects of the present disclosure. Residual learning is a method that introduces skip connections to learn from one or more features that is/are created at the layers before the previous layer and to facilitate backpropagation of errors during model training. While not limited to this configuration, in a current setting, skip connections between blocks of convolution layer(s) are introduced as shown in FIG. 9B. As shown in at least the embodiment example of FIG. 9B, a depth (total number of convolutional layers) is 34 (smaller/bigger depths may be used, but, in one or more embodiments, a depth of 34 may be preferred), batch size is 12, a width (number of filters in each image) is 64 (in one or more embodiments, a smaller width may be used, and in one or more embodiments, a smaller width may be preferred), and a learning rate is $10^{-4}$. As aforementioned, in one or more embodiments, a convolutional autoencoder (CAE) may be used.

One or more embodiments may use a recurrent convolutional neural network object detection model with long short-term memory (see e.g., "long short-term memory" as discussed in "Long Short-Term Memory" by Hochreiter, et al., Neural Computation, Volume 9, Issue 8, November 1997 (https://dl.acm.org/doi/10.1162/neco.1997.9.81735); as discussed in "Fundamentals of Recurrent Neural Network (RNN) and Long Short-Term Memory (LSTM) Network" by Alex Sherstinsky, Elsevier Journal "Physica D: Nonlinear Phenomena", Volume 404, March 2020 (https://arxiv.org/abs/1808.03314); as discussed in "Sequence to Sequence Learning with Neural Networks", by Sutskeyer, et al., December 2014 (https://papers.nips.cc/paper/5346-sequence-to-sequence-learning-with-neural-networks.pdf); etc.) that enables consideration of spatial and temporal information for predicting maker locations. Since a radiopaque marker moves a certain direction during the pullback, utilizing that information may improve success rate of marker detection. In this case, model input is a sequence of multiple frames, and model output is a sequence of spatial coordinates for marker locations in each of the given images.

One or more embodiments may use a neural network model that is created by transfer learning. Transfer learning is a method of using a model with pre-trained (instead of randomly initialized) parameters, that have been optimized for the same or a different objective (e.g., to solve a different image recognition or computer vision issue) on a different data set with a potentially different underlying data distribution. The model architecture may be adapted or used to solve new objective(s) or issue(s), for example, by adding, removing, or replacing one or more layers of the neural network, and the potentially modified model is then further trained (fine-tuned) on the new data set. Under the assumption that lower-level features, such as edge detector(s), are transferrable from one objective or issue domain to another, this learning approach may help improve the performance of the model, especially when the size of the available data set is small. In this specific application, by using pre-trained model with residual learning, the success rate improves about 30%.

In one or more embodiments of an object detection model, the root mean square error (RMSE) between the actual location and the predicted location may be used as an evaluation metric for model evaluation. In one or more embodiments, a success rate may be computed by applying a threshold criterion and calculating the number of frame examples in each pullback for which the RMSE value is smaller than a predetermined or set threshold value (see e.g., details of FIGS. 10A, 10B, and 10C). The success rate may additionally be computed at different threshold values, for example, in the range from 0.1 mm to 10 mm with a step size of 0.1 mm. RMSE or the derived success rate may be used, individually or combined, for model evaluation. In experiments conducted, at least one reason why success rate was used here is to see how much improvement may be achieved with different threshold(s) and to link that information in a clinical setting or settings. For example, the success rate improves 10% with 0.1 mm bigger threshold value, and a 0.1 mm difference in an angio image may least likely affect a physician's plan of procedure such that use of a bigger threshold value may be chosen or selected.

In one or more embodiments of an object detection model, evaluation may be performed by assessing both root mean square error and difference of pullback paths between ground truth and prediction. Considering the movement of the marker from one frame to one after as a vector, the difference of pullback paths can be evaluated in terms of the differences of the magnitude (i.e., length) of the vectors (in ground truth and in prediction) and the angle differences of the vectors. Root mean square error helps understand the averaged frame-by-frame performance of entire pullback, while difference of pullback paths enables understanding the performance per pullback, i.e., whether the model can predict a movement of marker correctly or not.

In one or more embodiments of an object detection model, evaluation may be performed by assessing the movement of the detected/predicted marker location over a certain period of time. Since the marker should move in a certain direction, which can be defined by a user and/or with a given prior knowledge of anatomy of the vessel (from distal to proximal of the vessel), if the detected/predicted marker location does not move the appropriate direction, a model can be penalized. For example, if frame-by-frame prediction is performed, the movement of the detected/predicted marker location can be assessed by comparing the detected/predicted location in a certain number of frames prior to the frame that is currently used for training. If a model that uses a sequence of frames as input, the movement can be evaluated by comparing the detected/predicted marker locations at the first and the last frames of the sequence.

Since the data set is split into training, validation, and test sets or groups, success rate was evaluated for each subset in one or more embodiments as shown in FIGS. 10A-10C. "Longer training time" indicates more iteration(s) of training: 500 iterations (1000), 3500 iterations (1001), and 6500 iterations (1002), for example.

In a case where the data is split frame-basis, all three data sets show the similar success rate results. However, in a case where the data is split pullback-basis, and in a case where a system encounters to the data that is less correlated (or handles or processes data that is less correlated), the respective success rate on the validation data set and the test data set is significantly lower when compared to the success rate on the training data set (see FIGS. 10A-10C). The success rate difference indicates that the system is overfitting to the current data, which indicates that more data would be useful to train a model that can generalize better to unseen data.

FIG. 11 includes several examples of test and validation data along with root mean squared error calculations for one or more embodiments of an object detection model in accordance with one or more aspects of the present disclosure. Here, root mean squared error is used to evaluate the model performance. Smaller root mean squared error indicates better model structure. Although an increase of learning iterations over the full training data set (i.e., epochs) may help to improve performance on the validation set, it may not help to improve performance on the test set, which would be an indication that the model starts to overfit to the validation set. The difference between the two models of FIG. 11 may be due to the difference in the model architecture and/or due to other hyper-parameter settings.

Several non-limiting examples of differences between using a segmentation model and an object detection model are discussed herein. As discussed above, an object detection model may not have enough resolution for accurate prediction of the marker location. That said, in one or more embodiments, a sufficiently optimized object detection model may achieve better or maximized performance. On the other hand, while a segmentation model may provide better resolution than at least one embodiment of an object detection model, as aforementioned, at least one embodiment of a segmentation model may use post-processing to obtain a coordinate of predicted marker location (which may lead to a lower marker detection success rate in one or more embodiments).

As discussed further herein, there are multiple options that may be used to improve or address the above differences between segmentation and object detection models. By way of a couple of non-limiting, non-exhaustive examples: (i) a combination model may be employed, which, for example, involves running a semantic segmentation model and then applying an object detection model to an area with higher probability from the segmentation model (one or more features of such combined approaches may be used in one or more embodiments of the present disclosure, one or more features, including, but not limited to, those as discussed in "Mask R-CNN" to Kaiming He, et al., Facebook AI Research (FAIR), Jan. 24, 2018 (https://arxiv.org/pdf/1703.06870.pdf), which is incorporated by reference herein in its entirety); and/or (ii) running an object detection model with a bigger normalized range, applying the object detection model, and then applying the object detection model again with a higher probability area from the first object detection model.

After making improvements to one or more architecture models as discussed herein, specific advantages may include, but are not limited to, one or more of the following: higher resolution leading to a more accurate prediction result; lower computational memory and/or processing may be utilized (less resource(s) used, faster processing achieved, etc.); and no user interaction is needed (while one or more embodiments may involve user interaction).

The method of FIG. 3 involves such considerations in selecting a model to be used, and to use an identifier or detector to predict marker location. For example, step S204 of FIG. 3 regarding loading a trained model from a memory may involve one or more of the aforementioned to determine which model to load. Experiments have been and are continuing to be conducted to train multiple models and to gather information as to which models perform more efficiently or optimally than other models. For one or more embodiments of final implementation, a trained model may be selected from the models having the better or best performance on the validation data set, and the test set may be used to estimate the generalization error. However, it is possible to have multiple trained models and compare performances between such models to pick the "possibly" better or best one for a given application or applications in one or more embodiments. This selection may be done by a user, or may be done automatically with certain evaluation metrics. Evaluation metrics may be driven based on input image quality and/or any other error metric(s) that is/are used during prediction of the model. By way of a further example, the choice of the model may be made based on input image quality. There may be a possibility that a certain combination of input image quality and model has higher performance than another combination or combinations.

By way of another example, step S210 of FIG. 3 regarding displaying a result or modified result(s) may be done, but is not limited to, using one or more features as discussed in U.S. Pat. Pub. No. 2018/0271614, the disclosure of which is incorporated by reference herein in its entirety; as discussed in U.S. Pat. Pub. No. 2019/0029624, the disclosure of which is incorporated by reference herein in its entirety; as discussed in U.S. Pat. Pub. No. 2019/0029623, the disclosure of which is incorporated by reference herein in its entirety; and as discussed in U.S. Provisional Pat. App. No. 62/798,885, filed on Jan. 30, 2019, the disclosure of which is incorporated by reference herein in its entirety.

Additionally, in one or more embodiments, training data may be obtained using other imaging data and/or user feedback. For example, angio images that are acquired during balloon catheter and/or stent catheter delivery or other intravascular imaging (e.g., IVUS pullback) may potentially also be used as training data and may help in learning models that generalize better. Additionally or alternatively, as an example of user feedback, data may be captured by a graphical user interface (GUI) that is used to present model predictions to a user, and that captured data may allow the user to evaluate predicted marker locations and correct marker locations (if needed/useful). Validated and corrected samples may be used as additional training data to update (and further improve) the model in one or more embodiments.

In view of the above, and in view of other artificial intelligence details/features discussed below, one or more embodiments of the present disclosure may incorporate or use application of machine learning for automated detection of markers (e.g., radiodense markers, radiopaque markers, etc.) in one or more angiography images (e.g., in one or more embodiments, little or no user interaction may be a benefit/outcome). One or more embodiments may employ an object/keypoint detection model with higher resolution, and may result in a benefit/outcome of being able to predict object/keypoint coordinates at subpixel spatial resolution (e.g., in millimeter unit(s) in a patient coordinate system). One or more embodiments may employ introduction (e.g., intentional introduction) of a marker (e.g., radiodense marker, radiopaque marker, etc.) into angiography images to simplify computer vision task(s), and may result in a benefit/outcome of facilitating marker (object/keypoint) detection using machine learning. One or more embodiments may incorporate an ability to use additional, widely available images, in which a similar marker (the size and/or material may be different between markers) is introduced for model training (transfer learning).

Visualization, PCI procedure planning, and physiological assessment may be combined to perform complete PCI planning beforehand, and to perform complete assessment after the procedure. Once a 3D structure is constructed or reconstructed and a user specifies an interventional device, e.g., a stent, that is planned to be used, virtual PCI may be performed in a computer simulation (e.g., by one or more of the computers discussed herein, such as, but not limited to, the computer 2, the processor computer 1200, the processor or computer 1200', any other processor discussed herein, etc.). Then, another physiological assessment may be performed based on the result of the virtual PCI. This approach allows a user to find the best device (e.g., interventional device, implant, stent, etc.) for each patient before or during the procedure.

While a few examples of GUIs have been discussed herein and shown in one or more of the figures of the present disclosure, other GUI features, imaging modality features, or other imaging features, may be used in one or more embodiments of the present disclosure, such as the GUI feature(s), imaging feature(s), and/or imaging modality feature(s) disclosed in U.S. patent Ser. No. 16/401,390, filed May 2, 2019, and disclosed in U.S. Pat. Pub. No. 2019/0029624 and WO 2019/023375, which application(s) and publication(s) are incorporated by reference herein in their entireties.

One or more methods or algorithms for calculating stent expansion/underexpansion or apposition/malapposition may be used in one or more embodiments of the present disclosure, including, but not limited to, the expansion/underexpansion and apposition/malapposition methods or algorithms discussed in U.S. Pat. Pub. Nos. 2019/0102906 and 2019/0099080, which publications are incorporated by reference herein in their entireties.

One or more methods or algorithms for calculating or evaluating cardiac motion using an angiography image and/or for displaying anatomical imaging may be used in one or more embodiments of the present disclosure, including, but not limited to, the methods or algorithms discussed in U.S. Pat. Pub. No. 2019/0029623 and U.S. Pat. Pub. No. 2018/0271614 and WO 2019/023382, which publications are incorporated by reference herein in their entireties.

One or more methods or algorithms for performing co-registration and/or imaging may be used in one or more embodiments of the present disclosure, including, but not limited to, the methods or algorithms discussed in U.S. Pat. App. No. 62/798,885, filed on Jan. 30, 2019, and discussed in U.S. Pat. Pub. No. 2019/0029624, which application(s) and publication(s) are incorporated by reference herein in their entireties.

Such information and other features discussed herein may be applied to other applications, such as, but not limited to, co-registration, other modalities, etc. Indeed, the useful applications of the features of the present disclosure and of the aforementioned applications and patent publications are not limited to the discussed modalities, images, or medical procedures. Additionally, depending on the involved modalities, images, or medical procedures, one or more control bars may be contoured, curved, or have any other configuration desired or set by a user. For example, in an embodiment using a touch screen as discussed herein, a user may define or create the size and shape of a control bar based on a user moving a pointer, a finger, a stylus, another tool, etc. on the touch screen (or alternatively by moving a mouse or other input tool or device regardless of whether a touch screen is used or not).

One or more embodiments of the present disclosure may include taking multiple views (e.g., OCT image, ring view, tomo view, anatomical view, etc.), and one or more embodiments may highlight or emphasize NIRAF. In one or more embodiments, two handles may operate as endpoints that may bound the color extremes of the NIRAF data in or more embodiments. In addition to the standard tomographic view, the user may select to display multiple longitudinal views. When connected to an angiography system, the Graphical User Interface (GUI) may also display angiography images.

In accordance with one or more aspects of the present disclosure, the aforementioned features are not limited to being displayed or controlled using any particular GUI. In general, the aforementioned imaging modalities may be used in various ways, including with or without one or more features of aforementioned embodiments of a GUI or GUIs. For example, a GUI may show an OCT image with a tool or marker to change the image view as aforementioned even if not presented with a GUI (or with one or more other components of a GUI; in one or more embodiments, the display may be simplified for a user to display set or desired information).

The procedure to select the region of interest and the position of a marker, an angle, a plane, etc., for example, using a touch screen, a GUI (or one or more components of a GUI; in one or more embodiments, the display may be simplified for a user to display the set or desired information), a processor (e.g., processor or computer 2, 1200, 1200', or any other processor discussed herein) may involve, in one or more embodiments, a single press with a finger and dragging on the area to make the selection or modification. The new orientation and updates to the view may be calculated upon release of a finger, or a pointer.

For one or more embodiments using a touch screen, two simultaneous touch points may be used to make a selection or modification, and may update the view based on calculations upon release.

One or more functions may be controlled with one of the imaging modalities, such as the angiography image view or the OCT image view, to centralize user attention, maintain focus, and allow the user to see all relevant information in a single moment in time.

In one or more embodiments, one imaging modality may be displayed or multiple imaging modalities may be displayed.

One or more procedures may be used in one or more embodiments to select a region of choice or a region of interest for a view. For example, after a single touch is made on a selected area (e.g., by using a touch screen, by using a mouse or other input device to make a selection, etc.), the semi-circle (or other geometric shape used for the designated area) may automatically adjust to the selected region of choice or interest. Two (2) single touch points may operate to connect/draw the region of choice or interest. A single touch on a tomo or tomographic view (e.g., the OCT view 403 or 603) may operate to sweep around the tomo view, and may connect to form the region of choice or interest.

Figure 12A:
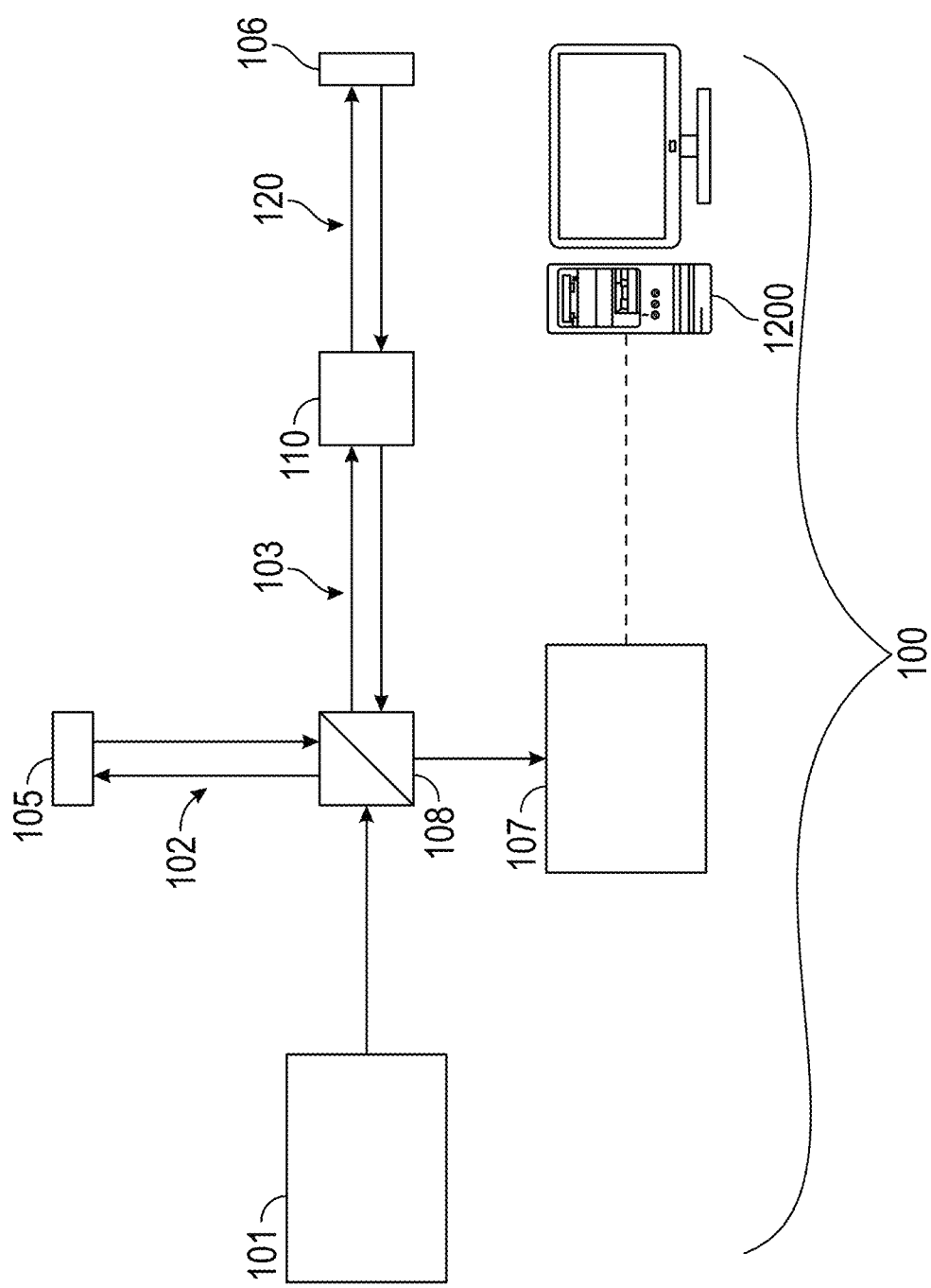
FIG. 12A shows at least one embodiment of an OCT apparatus or system for utilizing one or more imaging modalities and artificial intelligence for detecting marker(s) and/or performing coregistration in accordance with one or more aspects of the present disclosure.

FIG. 12A shows an OCT system 100 (as referred to herein as "system 100" or "the system 100") which may be used for one or more imaging modalities, such as, but not limited to, angiography, Optical Coherence Tomography (OCT), Multi-modality OCT (MM-OCT), near-infrared fluorescence (NIRAF), OCT-NIRAF, etc., and/or for employing one or more additional features discussed herein, including, but not limited to, artificial intelligence processes (e.g., machine or deep learning, residual learning, artificial intelligence ("AI") co-registration, marker detection, etc.) in accordance with one or more aspects of the present disclosure. The system 100 comprises a light source 101, a reference arm 102, a sample arm 103, a deflected or deflecting section 108, a reference mirror (also referred to as a "reference reflection", "reference reflector", "partially reflecting mirror" and a "partial reflector") 105, and one or more detectors 107 (which may be connected to a computer 1200). In one or more embodiments, the system 100 may include a patient interface device or unit ("PIU") no and a catheter 120 (see e.g., embodiment examples of a PIU and a catheter as shown in FIGS. 1A-1B, FIG. 4 and/or FIGS. 12A-12C), and the system 100 may interact with an object 106, a patient (e.g., a blood vessel of a patient) 106, etc. (e.g., via the catheter 120 and/or the PIU 110). In one or more embodiments, the system 100 includes an interferometer or an interferometer is defined by one or more components of the system 100, such as, but not limited to, at least the light source 101, the reference arm 102, the sample arm 103, the deflecting section 108 and the reference mirror 105.

Figure 12B:
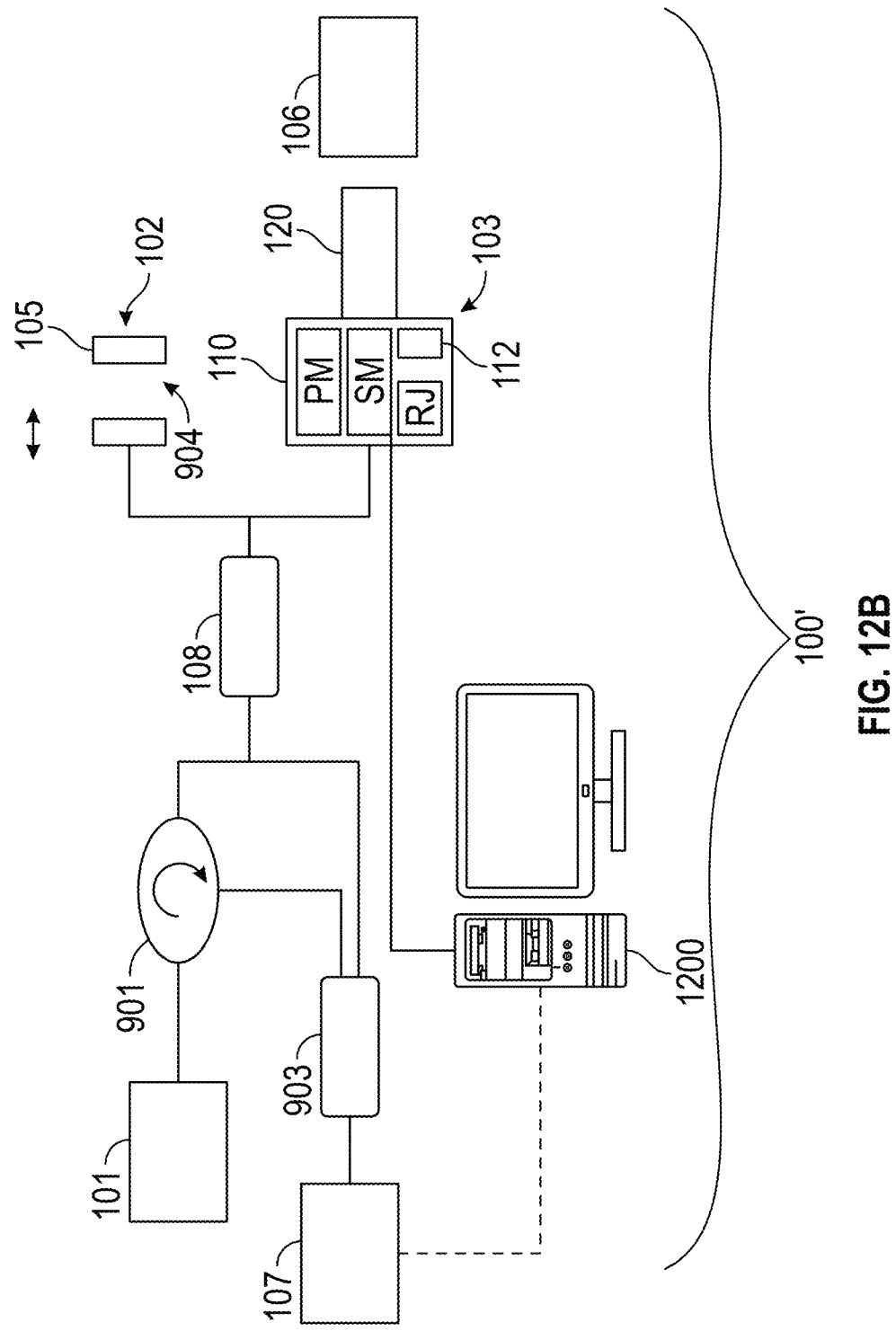
FIG. 12B shows at least another embodiment of an OCT apparatus or system for utilizing one or more imaging modalities and artificial intelligence for detecting marker(s) and/or performing coregistration in accordance with one or more aspects of the present disclosure.

In accordance with one or more further aspects of the present disclosure, bench top systems may be utilized for one or more imaging modalities, such as, but not limited to, angiography, Optical Coherence Tomography (OCT), Multimodality OCT (MM-OCT), near-infrared fluorescence (NI-RAF), OCT-NIRAF, etc., and/or for employing one or more additional features discussed herein, including, but not limited to, artificial intelligence processes (e.g., machine or deep learning, residual learning, artificial intelligence ("AI") co-registration, marker detection, etc.) in accordance with one or more aspects of the present disclosure. FIG. 12B shows an example of a system that can utilize the one or more imaging modalities, such as, but not limited to, angiography, Optical Coherence Tomography (OCT), Multi-modality OCT (MM-OCT), near-infrared fluorescence (NI-RAF), OCT-NIRAF, etc., and/or for employing one or more additional features discussed herein, including, but not limited to, artificial intelligence processes (e.g., machine or deep learning, residual learning, artificial intelligence ("AI") co-registration, marker detection, etc.) in accordance with one or more aspects of the present disclosure discussed herein for a bench-top such as for ophthalmic applications. A light from a light source 101 delivers and splits into a reference arm 102 and a sample arm 103 with a deflecting section 108. A reference beam goes through a length adjustment section 904 and is reflected from a reference mirror (such as or similar to the reference mirror or reference reflection 105 shown in FIG. 12A) in the reference arm 102 while a sample beam is reflected or scattered from an object, a patient (e.g., blood vessel of a patient), etc. 106 in the sample arm 103 (e.g., via the PIU no and the catheter 120). In one embodiment, both beams combine at the deflecting section 108 and generate interference patterns. In one or more embodiments, the beams go to the combiner 903, and the combiner 903 combines both beams via the circulator 901 and the deflecting section 108, and the combined beams are delivered to one or more detectors (such as the one or more detectors 107). The output of the interferometer is continuously acquired with one or more detectors, such as the one or more detectors 107. The electrical analog signals are converted to the digital signals to analyze them with a computer, such as, but not limited to, the computer 1200 (see FIGS. 12A-12C; also shown in FIG. 14 discussed further below), the computer 1200' (see e.g., FIG. 15 discussed further below), the computer 2 (see FIG. 1A), the processors 26, 36, 50 (see FIG. 1B), any other computer or processor discussed herein, etc. Additionally or alternatively, one or more of the computers, CPUs, processors, etc. discussed herein may be used to process, control, update, emphasize, and/or change one or more of imaging modalities, and/or process the related techniques, functions or methods, or may process the electrical signals as discussed above.

Figure 12C:
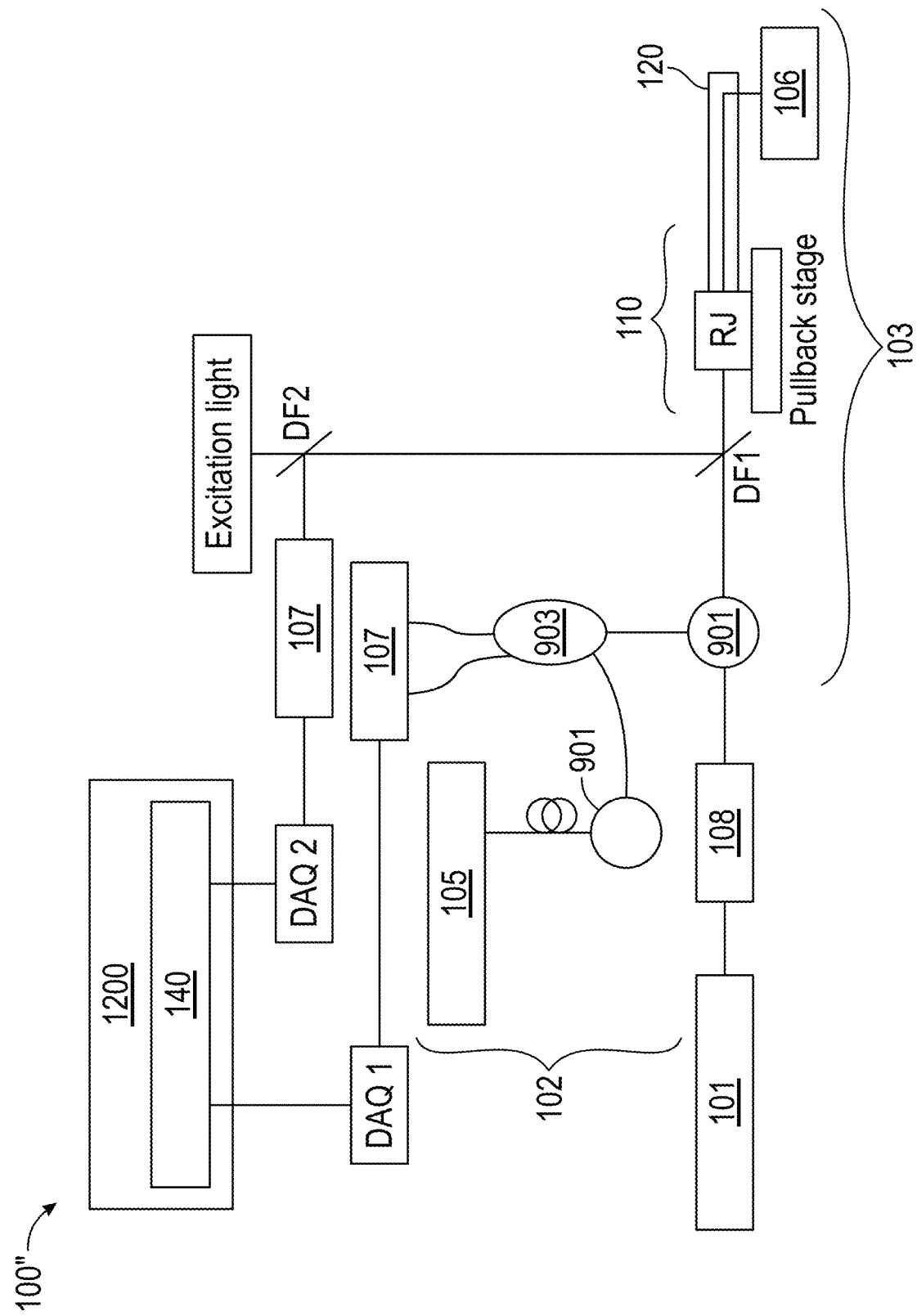
FIG. 12C shows at least a further embodiment of an OCT and NIRAF apparatus or system for utilizing one or more imaging modalities and artificial intelligence for detecting marker(s) and/or performing coregistration in accordance with one or more aspects of the present disclosure.

The electrical analog signals may be converted to the digital signals to analyze them with a computer, such as, but not limited to, the computer 1200 (see FIGS. 1B and 12A-12C; also shown in FIG. 14 discussed further below), the computer 1200' (see e.g., FIG. 15 discussed further below), the computer 2 (see FIG. 1A), any other processor or computer discussed herein, etc. Additionally or alternatively, one or more of the computers, CPUs, processors, etc. discussed herein may be used to process, control, update, emphasize, and/or change one or more imaging modalities, and/or process the related techniques, functions or methods, or may process the electrical signals as discussed above. In one or more embodiments (see e.g., FIG. 12B), the sample arm 103 includes the PIU no and the catheter 120 so that the sample beam is reflected or scattered from the object, patient (e.g., blood vessel of a patient), etc. 106 as discussed herein. In one or more embodiments, the PIU no may include one or more motors to control the pullback operation of the catheter 120 (or one or more components thereof) and/or to control the rotation or spin of the catheter 120 (or one or more components thereof) (see e.g., the motor M of FIG. 1B). For example, as best seen in FIG. 12B, the PIU no may include a pullback motor (PM) and a spin motor (SM), and/or may include a motion control unit 112 that operates to perform the pullback and/or rotation features using the pullback motor PM and/or the spin motor SM. As discussed herein, the PIU no may include a rotary junction (e.g., rotary junction RJ as shown in FIGS. 12B and 12C). The rotary junction RJ may be connected to the spin motor SM so that the catheter 120 may obtain one or more views or images of the object, patient (e.g., blood vessel of a patient), etc. 106. The computer 1200 (or the computer 1200', computer 2, any other computer or processor discussed herein, etc.) may be used to control one or more of the pullback motor PM, the spin motor SM and/or the motion control unit 112. An OCT system may include one or more of a computer (e.g., the computer 1200, the computer 1200', computer 2, any other computer or processor discussed herein, etc.), the PIU no, the catheter 120, a monitor (such as the display 1209), etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

In one or more embodiments including the deflecting or deflected section 108 (best seen in FIGS. 12A-12C), the deflected section 108 may operate to deflect the light from the light source 101 to the reference arm 102 and/or the sample arm 103, and then send light received from the reference arm 102 and/or the sample arm 103 towards the at least one detector 107 (e.g., a spectrometer, one or more components of the spectrometer, another type of detector, etc.). In one or more embodiments, the deflected section (e.g., the deflected section 108 of the system 100, 100', 100", any other system discussed herein, etc.) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 (or any other system discussed herein) such as, but not limited to, one or more of the light source 101, the deflected section 108, the rotary junction RJ, a PIU no, a catheter 120, etc. One or more features of the aforementioned configurations of at least FIGS. 1-12B may be incorporated into one or more of the systems, including, but not limited to, the system 100, 100', 100", discussed herein.

In accordance with one or more further aspects of the present disclosure, one or more other systems may be utilized with one or more of the multiple imaging modalities and related method(s) as disclosed herein. FIG. 12C shows an example of a system 100" that may utilize the one or more multiple imaging modalities, such as, but not limited to, angiography, Optical Coherence Tomography (OCT), Multimodality OCT (MM-OCT), near-infrared fluorescence (NI-RAF), OCT-NIRAF, etc., and/or for employing one or more additional features discussed herein, including, but not limited to, artificial intelligence processes (e.g., machine or deep learning, residual learning, artificial intelligence ("AI") co-registration, marker detection, etc.) and/or related technique(s) or method(s) such as for ophthalmic applications in accordance with one or more aspects of the present disclosure. FIG. 12C shows an exemplary schematic of an OCT-fluorescence imaging system 100", according to one or more embodiments of the present disclosure. An OCT light source 101 (e.g., with a 1.3 µm) is delivered and split into a reference arm 102 and a sample arm 103 with a deflector or deflected section (e.g., a splitter) 108, creating a reference beam and sample beam, respectively. The reference beam from the OCT light source 101 is reflected by a reference mirror 105 while a sample beam is reflected or scattered from an object (e.g., an object to be examined, an object, a patient, etc.) 106 through a circulator 901, a rotary junction 90 ("RJ") and a catheter 120. In one or more embodiments, the fiber between the circulator 901 and the reference mirror or reference reflection 105 may be coiled to adjust the length of the reference arm 102 (best seen in FIG. 12C). Optical fibers in the sample arm 103 may be made of double clad fiber ("DCF"). Excitation light for the fluorescence may be directed to the RJ 90 and the catheter 120, and illuminate the object (e.g., an object to be examined, an object, a patient, etc.) 106. The light from the OCT light source 101 may be delivered through the core of DCF while the fluorescence light emitted from the object (e.g., an object to be examined, an object, a patient, etc.) 106 may be collected through the cladding of the DCF. For pullback imaging, the RJ 90 may be moved with a linear stage to achieve helical scanning of the object (e.g., an object to be examined, an object, a patient, etc.) 106. In one or more embodiments, the RJ 90 may include any one or more features of an RJ as discussed herein. Dichroic filters DF1, DF2 may be used to separate excitation light and the rest of fluorescence and OCT lights. For example (and while not limited to this example), in one or more embodiments, DF1 may be a long pass dichroic filter with a cutoff wavelength of ~1000 nm, and the OCT light, which may be longer than a cutoff wavelength of DF1, may go through the DF1 while fluorescence excitation and emission, which are a shorter wavelength than the cut off, reflect at DF1. In one or more embodiments, for example (and while not limited to this example), DF2 may be a short pass dichroic filter; the excitation wavelength may be shorter than fluorescence emission light such that the excitation light, which has a wavelength shorter than a cutoff wavelength of DF2, may pass through the DF2, and the fluorescence emission light reflect with DF2. In one embodiment, both beams combine at the deflecting section 108 and generate interference patterns. In one or more embodiments, the beams go to the coupler or combiner 903, and the coupler or combiner 903 combines both beams via the circulator 901 and the deflecting section 108, and the combined beams are delivered to one or more detectors (such as the one or more detectors 107; see e.g., the first detector 107 connected to the coupler or combiner 903 in FIG. 12C).

In one or more embodiments, the optical fiber in the catheter 120 operates to rotate inside the catheter 120, and the OCT light and excitation light may be emitted from a side angle of a tip of the catheter 120. After interacting with the object or patient 106, the OCT light may be delivered back to an OCT interferometer (e.g., via the circulator 901 of the sample arm 103), which may include the coupler or combiner 903, and combined with the reference beam (e.g., via the coupler or combiner 903) to generate interference patterns. The output of the interferometer is detected with a first detector 107, wherein the first detector 107 may be photodiodes or multi-array cameras, and then may be recorded to a computer (e.g., to the computer 2, the computer 1200 as shown in FIG. 12C, the computer 1200', or any other computer discussed herein) through a first data-acquisition unit or board ("DAQ1").

Simultaneously or at a different time, the fluorescence intensity may be recorded through a second detector 107 (e.g., a photomultiplier) through a second data-acquisition unit or board ("DAQ2"). The OCT signal and fluorescence signal may be then processed by the computer (e.g., to the computer 2, the computer 1200 as shown in FIG. 12C, the computer 1200', or any other computer discussed herein) to generate an OCT-fluorescence data set 140, which includes or is made of multiple frames of helically scanned data. Each set of frames includes or is made of multiple data elements of co-registered OCT and fluorescence data, which correspond to the rotational angle and pullback position.

Detected fluorescence or auto-fluorescence signals may be processed or further processed as discussed in U.S. Pat. App. No. 62/861,888, filed on Jun. 14, 2019, the disclosure of which is incorporated herein by reference in its entirety, and/or as discussed in U.S. patent application Ser. No. 16/368,510, filed Mar. 28, 2019, the disclosure of which is incorporated herein by reference herein in its entirety.

While not limited to such arrangements, configurations, devices or systems, one or more embodiments of the devices, apparatuses, systems, methods, storage mediums, GUI's, etc. discussed herein may be used with an apparatus or system as aforementioned, such as, but not limited to, for example, the system 100, the system 100', the system 100", the devices, apparatuses, or systems of FIGS. 1A-1B and 12A-16, any other device, apparatus or system discussed herein, etc. In one or more embodiments, one user may perform the method(s) discussed herein. In one or more embodiments, one or more users may perform the method(s) discussed herein. In one or more embodiments, one or more of the computers, CPUs, processors, etc. discussed herein may be used to process, control, update, emphasize, and/or change one or more of the imaging modalities, and/or process the related techniques, functions or methods, or may process the electrical signals as discussed above.

The light source 101 may include a plurality of light sources or may be a single light source. The light source 101 may be a broadband lightsource, and may include one or more of a laser, an organic light emitting diode (OLED), a light emitting diode (LED), a halogen lamp, an incandescent lamp, supercontinuum light source pumped by a laser, and/or a fluorescent lamp. The light source 101 may be any light source that provides light which may then be dispersed to provide light which is then used for imaging, performing control, viewing, changing, emphasizing methods for imaging modalities, constructing or reconstructing 3D structure(s), and/or any other method discussed herein. The light source 101 may be fiber coupled or may be free space coupled to the other components of the apparatus and/or system 100, 100', 100", the devices, apparatuses or systems of FIGS. 1A-1B and 12A-16, or any other embodiment discussed herein. As aforementioned, the light source 101 may be a swept-source (SS) light source.

Additionally or alternatively, the one or more detectors 107 may be a linear array, a charge-coupled device (CCD), a plurality of photodiodes or some other method of converting the light into an electrical signal. The detector(s) 107 may include an analog to digital converter (ADC). The one or more detectors may be detectors having structure as shown in one or more of FIGS. 1A-1B and 12A-16 and as discussed herein.

Figure 13:
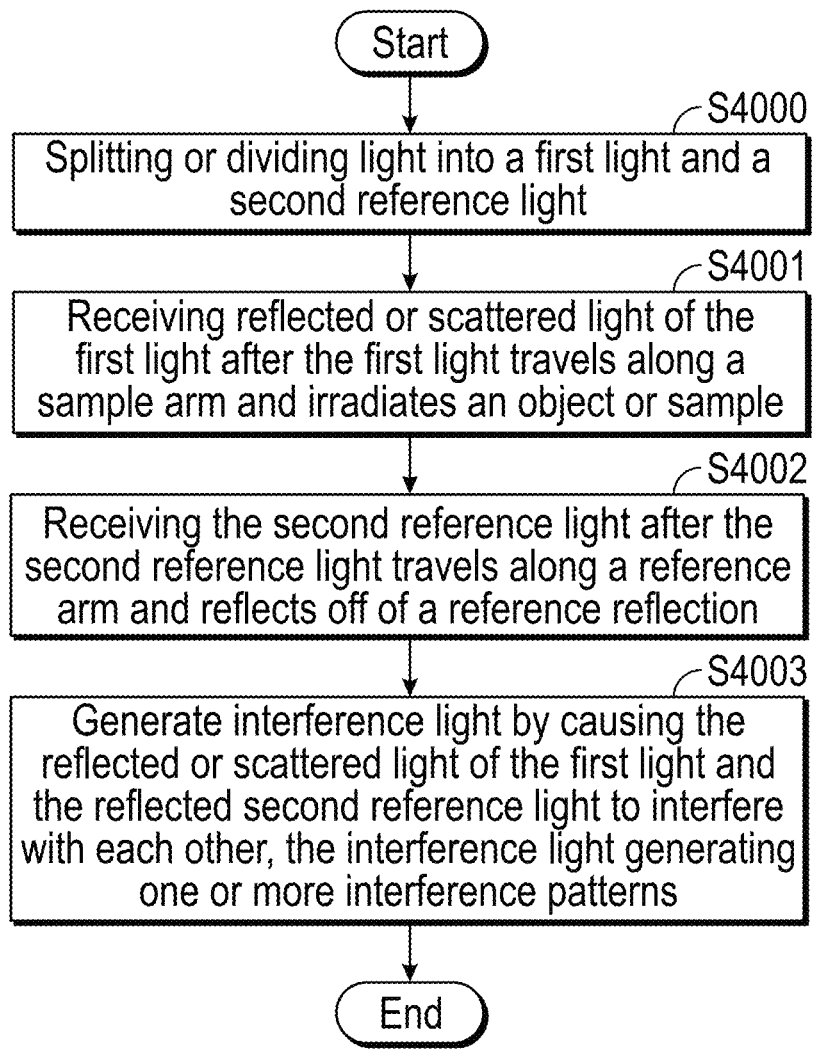
FIG. 13 is a flow diagram showing a method of performing an imaging feature, function or technique in accordance with one or more aspects of the present disclosure.

In accordance with one or more aspects of the present disclosure, one or more methods for performing imaging are provided herein. FIG. 13 illustrates a flow chart of at least one embodiment of a method for performing imaging. The method(s) may include one or more of the following: (i) splitting or dividing light into a first light and a second reference light (see step S4000 in FIG. 13); (ii) receiving reflected or scattered light of the first light after the first light travels along a sample arm and irradiates an object (see step S4001 in FIG. 13); (iii) receiving the second reference light after the second reference light travels along a reference arm and reflects off of a reference reflection (see step S4002 in FIG. 13); and (iv) generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 13). One or more methods may further include using low frequency monitors to update or control high frequency content to improve image quality. For example, one or more embodiments may use multiple imaging modalities, related methods or techniques for same, etc. to achieve improved image quality. In one or more embodiments, an imaging probe may be connected to one or more systems (e.g., the system 100, the system 100', the system 100", the devices, apparatuses or systems of FIGS. 1A-1B and 12A-16, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', the computer 2, any other computer or processor discussed herein, etc. The detection fibers may surround the illumination fiber, and the detection fibers may or may not be covered by a grating, a spacer, a lens, an end of a probe or catheter, etc.

The one or more detectors 107 may transmit the digital or analog signals to a processor or a computer such as, but not limited to, an image processor, a processor or computer 1200, 1200' (see e.g., FIGS. 12A-12C and 14-15), a computer 2 (see e.g., FIG. 1A), any other processor or computer discussed herein, a combination thereof, etc. The image processor may be a dedicated image processor or a general purpose processor that is configured to process images. In at least one embodiment, the computer 1200, 1200', 2 or any other processor or computer discussed herein may be used in place of, or in addition to, the image processor. In an alternative embodiment, the image processor may include an ADC and receive analog signals from the one or more detectors 107. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the devices, apparatuses or systems of FIGS. 1-12C, the computer 1200, the computer 1200', the computer 2, the image processor, may also include one or more components further discussed herein below (see e.g., FIGS. 14-15).

Figure 14:
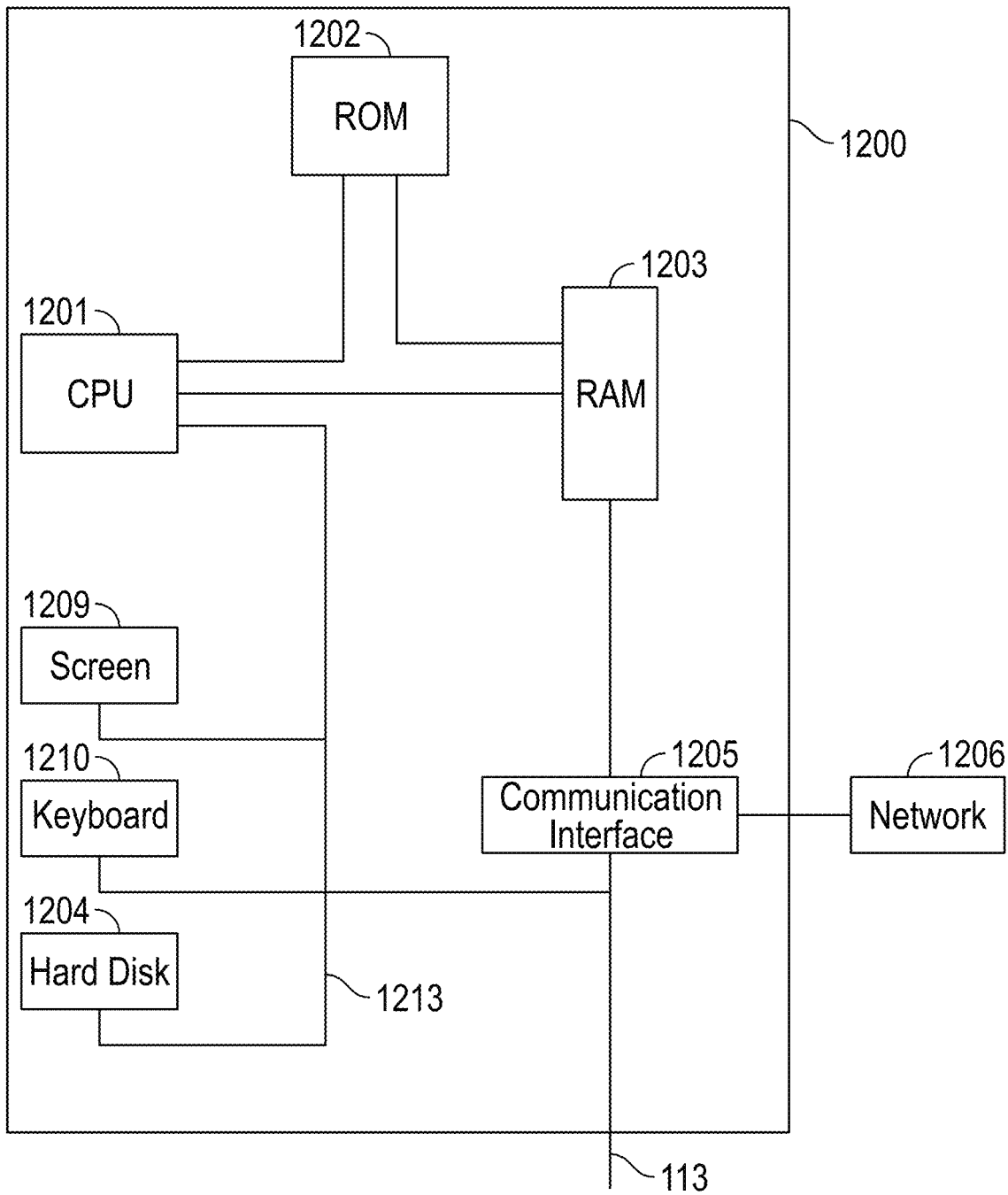
FIG. 14 shows a schematic diagram of an embodiment of a computer that may be used with one or more embodiments of an apparatus or system or one or more methods discussed herein in accordance with one or more aspects of the present disclosure.
Figure 15:
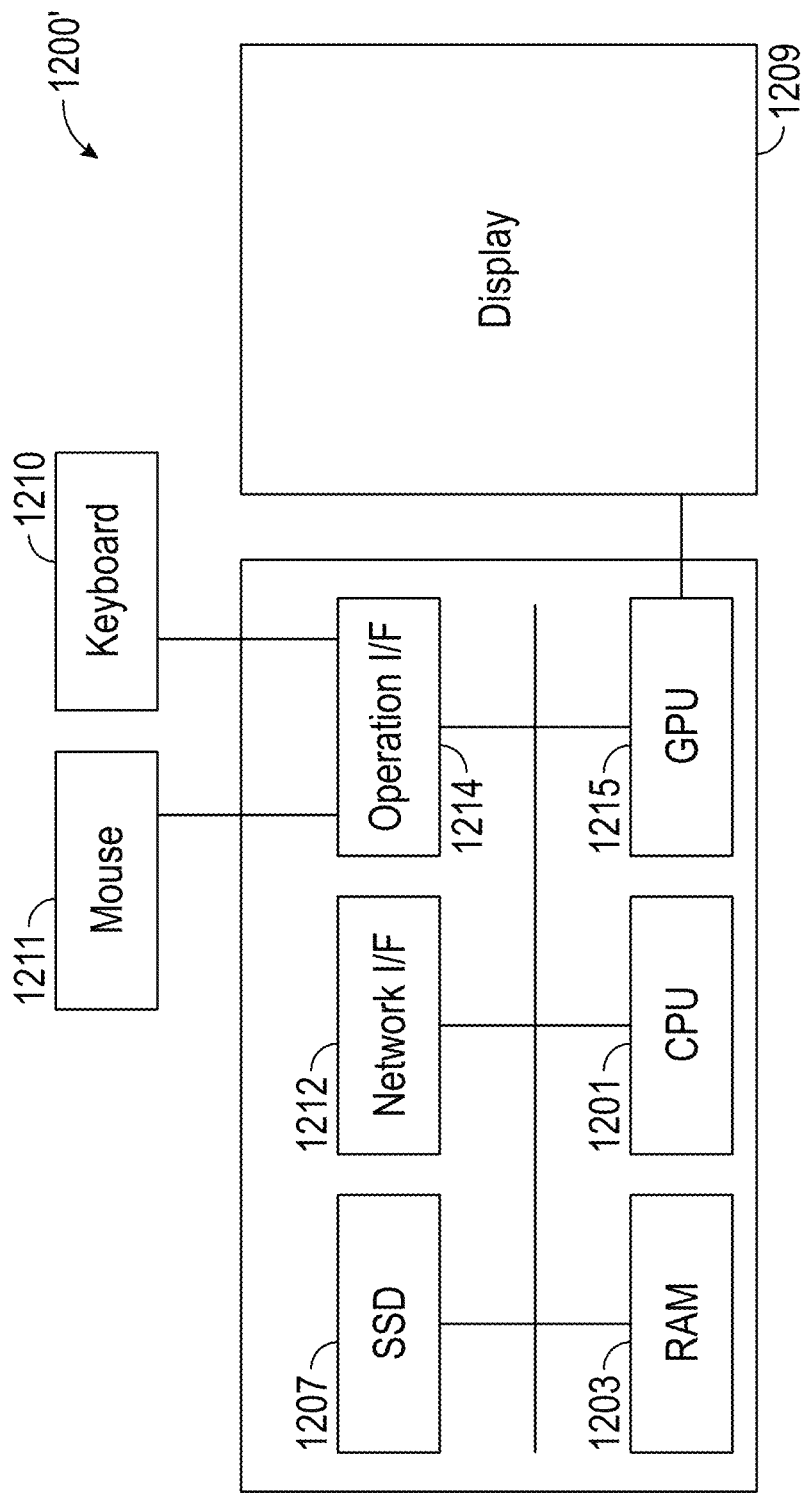
FIG. 15 shows a schematic diagram of another embodiment of a computer that may be used with one or more embodiments of an imaging apparatus or system or methods discussed herein in accordance with one or more aspects of the present disclosure.

In at least one embodiment, a console or computer 1200, 1200', a computer 2, any other computer or processor discussed herein, etc. operates to control motions of the RJ via the motion control unit (MCU) 112 or a motor M, acquires intensity data from the detector(s) in the one or more detectors 107, and displays the scanned image (e.g., on a monitor or screen such as a display, screen or monitor 1209 as shown in the console or computer 1200 of any of FIGS. 12A-12C and FIG. 14 and/or the console 1200' of FIG. 15 as further discussed below; the computer 2 of FIG. 1A; any other computer or processor discussed herein; etc.). In one or more embodiments, the MCU 112 or the motor M operates to change a speed of a motor of the RJ and/or of the RJ. The motor may be a stepping or a DC servo motor to control the speed and increase position accuracy (e.g., compared to when not using a motor, compared to when not using an automated or controlled speed and/or position change device, compared to a manual control, etc.).

The output of the one or more components of any of the systems discussed herein may be acquired with the at least one detector 107, e.g., such as, but not limited to, photodiodes, Photomultiplier tube(s) (PMTs), line scan camera(s), or multi-array camera(s). Electrical analog signals obtained from the output of the system 100, 100', 100", and/or the detector(s) 107 thereof, and/or from the devices, apparatuses, or systems of FIGS. 1-12C, are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Unless otherwise discussed herein, like numerals indicate like elements. For example, while variations or differences exist between the systems, such as, but not limited to, the system 100, the system 100', the system 100", or any other device, apparatus or system discussed herein, one or more features thereof may be the same or similar to each other, such as, but not limited to, the light source 101 or other component(s) thereof (e.g., the console 1200, the console 1200', etc.). Those skilled in the art will appreciate that the light source 101, the motor or MCU 112, the RJ, the at least one detector 107, and/or one or more other elements of the system 100 may operate in the same or similar fashion to those like-numbered elements of one or more other systems, such as, but not limited to, the devices, apparatuses or systems of FIGS. 1-12C, the system 100', the system 100", or any other system discussed herein. Those skilled in the art will appreciate that alternative embodiments of the devices, apparatuses or systems of FIGS. 1-12C, the system 100', the system 100", any other device, apparatus or system discussed herein, etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100 of FIG. 12A and one or more embodiments shown in any of FIGS. 1-11 and 12B-12C, for example, as discussed herein, there are similarities. Likewise, while the console or computer 1200 may be used in one or more systems (e.g., the system 100, the system 100', the system 100", the devices, apparatuses or systems of any of FIGS. 1-16, or any other system discussed herein, etc.), one or more other consoles or computers, such as the console or computer 1200', any other computer or processor discussed herein, etc., may be used additionally or alternatively.

There are many ways to compute intensity, viscosity, resolution (including increasing resolution of one or more images), etc., to use one or more imaging modalities, to construct or reconstruct 3D structure(s), and/or related methods for same, discussed herein, digital as well as analog. In at least one embodiment, a computer, such as the console or computer 1200, 1200', may be dedicated to control and monitor the imaging (e.g., OCT, single mode OCT, multimodal OCT, multiple imaging modalities, etc.) devices, systems, methods and/or storage mediums described herein.

The electric signals used for imaging may be sent to one or more processors, such as, but not limited to, a computer or processor 2 (see e.g., FIG. 1A), a computer 1200 (see e.g., FIGS. 12A-12B, 14 and 16), a computer 1200' (see e.g., FIGS. 15 and 16), etc. as discussed further below, via cable(s) or wire(s), such as, but not limited to, the cable(s) or wire(s) 113 (see FIG. 14). Additionally or alternatively, the electric signals, as aforementioned, may be processed in one or more embodiments as discussed above by any other computer or processor or components thereof. The computer or processor 2 as shown in FIG. 1A may be used instead of any other computer or processor discussed herein (e.g., computer or processors 1200, 1200', etc.), and/or the computer or processor 1200, 1200' may be used instead of any other computer or processor discussed herein (e.g., computer or processor 2). In other words, the computers or processors discussed herein are interchangeable, and may operate to perform any of the multiple imaging modalities feature(s) and method(s) discussed herein, including using, controlling, and changing a GUI or multiple GUI's.

Various components of a computer system 1200 are provided in FIG. 14. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS (or "Bus") or other connection lines (e.g., connection line 1213) between one or more of the aforementioned components (e.g., including but not limited to, being connected to the console, the probe, the imaging apparatus or system, any motor discussed herein, a light source, etc.). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a device or system, such as, but not limited to, an apparatus or system using one or more imaging modalities and related method(s) as discussed herein), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for tissue or object characterization, diagnosis, evaluation, imaging and/or construction or reconstruction. The system 1200 may further include one or more processors connected via a network connection (e.g., via network 1206). The CPU 1201 and any additional processor being used by the system 1200 may be located in the same telecom network or in different telecom networks (e.g., performing feature(s), function(s), technique(s), method(s), etc. discussed herein may be controlled remotely).

The I/O or communication interface 1205 provides communication interfaces to input and output devices, which may include a light source, a spectrometer, a microphone, a communication cable and a network (either wired or wireless), a keyboard 1210, a mouse (see e.g., the mouse 1211 as shown in FIG. 15), a touch screen or screen 1209, a light pen and so on. The communication interface of the computer 1200 may connect to other components discussed herein via line 113 (as diagrammatically shown in FIG. 14). The Monitor interface or screen 1209 provides communication interfaces thereto.

Any methods and/or data of the present disclosure, such as the methods for performing tissue or object characterization, diagnosis, examination, imaging (including, but not limited to, increasing image resolution, performing imaging using one or more imaging modalities, viewing or changing one or more imaging modalities and related methods (and/or option(s) or feature(s)), etc.), and/or construction or reconstruction, for example, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 15), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 14. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 14), the processor or computer 2 (as shown in FIG. 1A) and/or the computer or processor 1200' (as shown in FIG. 15) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium. The computers or processors (e.g., 2, 1200, 1200', etc.) may include the aforementioned CPU structure, or may be connected to such CPU structure for communication therewith.

As aforementioned, hardware structure of an alternative embodiment of a computer or console 1200' is shown in FIG. 15. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. The computer or console 1200' may include a display 1209. The computer 1200' may connect with a motor, a console, or any other component of the device(s) or system(s) discussed herein via the operation interface 1214 or the network interface 1212 (e.g., via a cable or fiber, such as the cable or fiber 113 as similarly shown in FIG. 14). A computer, such as the computer 1200', may include a motor or motion control unit (MCU) in one or more embodiments. The operation interface 1214 is connected with an operation unit such as a mouse device 1211, a keyboard 1210 or a touch panel device. The computer 1200' may include two or more of each component.

At least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

The computer, such as the computer 2, the computer 1200, 1200', (or other component(s) such as, but not limited to, the PCU, etc.), etc. may communicate with an MCU, an interferometer, a spectrometer, a detector, etc. to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate any system discussed herein. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs any system discussed herein to set or change the imaging condition (e.g., improving resolution of an image or images), and to start or end the imaging. A light or laser source and a spectrometer and/or detector may have interfaces to communicate with the computers 1200, 1200' to send and receive the status information and the control signals.

Figure 16:
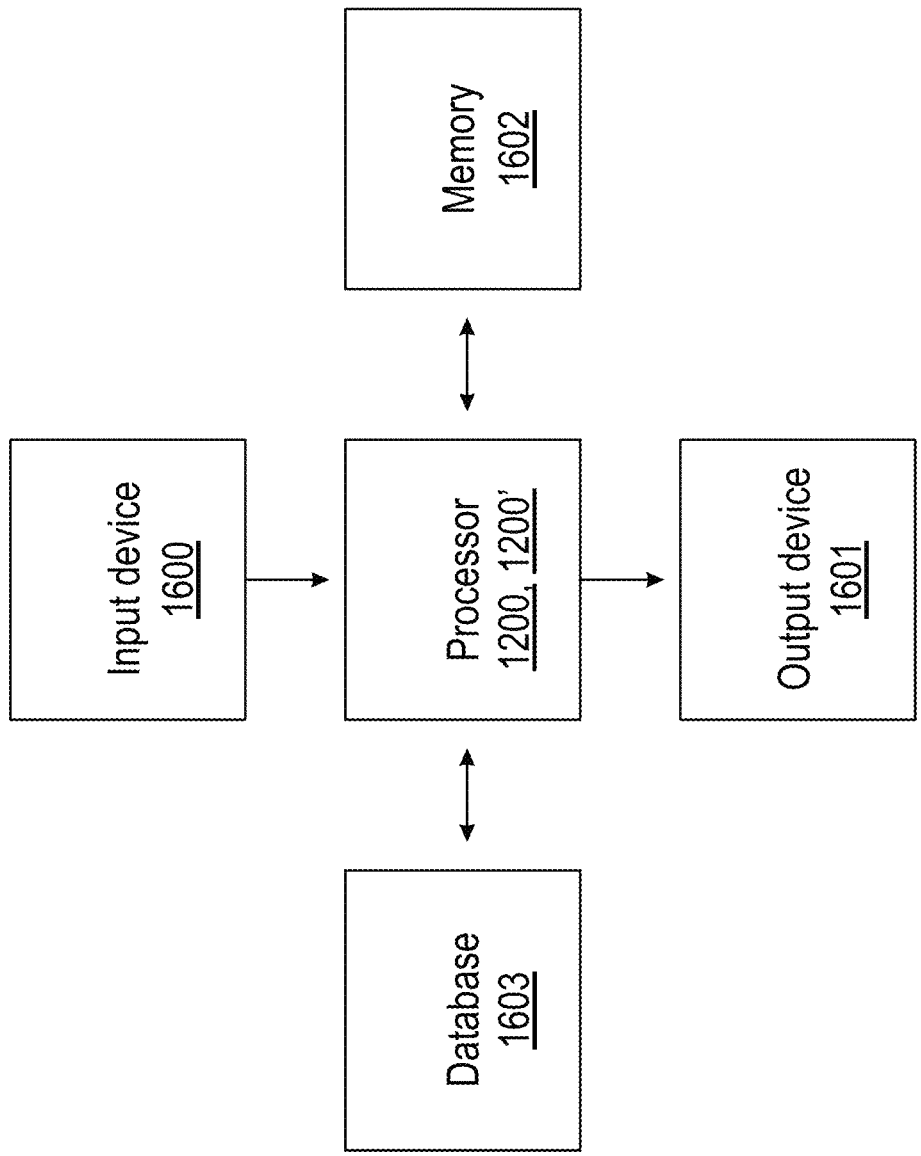
FIG. 16 shows a schematic diagram of at least an embodiment of a system using a computer or processor, a memory, a database, and input and output devices in accordance with one or more aspects of the present disclosure.

As shown in FIG. 16, one or more processors or computers 1200, 1200' (or any other processor discussed herein) may be part of a system in which the one or more processors or computers 1200, 1200' (or any other processor discussed herein) communicate with other devices (e.g., a database 1603, a memory 1602 (which may be used with or replaced by any other type of memory discussed herein or known to those skilled in the art), an input device 1600, an output device 1601, etc.). In one or more embodiments, one or more models may have been trained previously and stored in one or more locations, such as, but not limited to, the memory 1602, the database 1603, etc. In one or more embodiments, it is possible that one or more models and/or data discussed herein (e.g., training data, testing data, validation data, imaging data, etc.) may be input or loaded via a device, such as the input device 1600. In one or more embodiments, a user may employ an input device 1600 (which may be a separate computer or processor, a keyboard such as the keyboard 1210, a mouse such as the mouse 1211, a microphone, a screen or display 1209 (e.g., a touch screen or display), or any other input device known to those skilled in the art). In one or more system embodiments, an input device 1600 may not be used (e.g., where user interaction is eliminated by one or more artificial intelligence features discussed herein). In one or more system embodiments, the output device 1601 may receive one or more outputs discussed herein to perform the marker detection, the co-registration, and/or any other process discussed herein. In one or more system embodiments, the database 1603 and/or the memory 1602 may have outputted information (e.g., trained model(s), detected marker information, image data, test data, validation data, training data, coregistration result(s), segmentation model information, object detection/regression model information, combination model information, etc.) stored therein. That said, one or more embodiments may include several types of data stores, memory, storage media, etc. as discussed above, and such storage media, memory, data stores, etc. may be stored locally or remotely.

Additionally, unless otherwise specified, the term "subset" of a corresponding set does not necessarily represent a proper subset and may be equal to the corresponding set.

While one or more embodiments of the present disclosure include various details regarding a neural network model architecture and optimization approach, in one or more embodiments, any other model architecture, machine learning algorithm, or optimization approach may be employed. One or more embodiments may utilize hyper-parameter combination(s). One or more embodiments may employ data capture, selection, annotation as well as model evaluation (e.g., computation of loss and validation metrics) since data may be domain and application specific. In one or more embodiments, the model architecture may be modified and optimized to address a variety of computer visions issues (discussed below).

One or more embodiments of the present disclosure may automatically detect (predict a spatial location of) a radiodense OCT marker in a time series of X-ray images to co-register the X-ray images with the corresponding OCT images (at least one example of a reference point of two different coordinate systems). One or more embodiments may use deep (recurrent) convolutional neural network(s), which may improve marker detection and image co-registration significantly. One or more embodiments may employ segmentation and/or object/keypoint detection architectures to solve one or more computer vision issues in other domain areas in one or more applications. One or more embodiments employ several novel materials and methods to solve one or more computer vision or other issues (e.g., radiodense OCT marker detection in time series of X-ray images, for instance).

One or more embodiments employ data capture and selection. In one or more embodiments, the data is what makes such an application unique and distinguishes this application from other applications. For example, images may include a radiodense marker that is specifically used in one or more procedures (e.g., added to the OCT capsule, used in catheters/probes with a similar marker to that of an OCT marker, used in catheters/probes with a similar or same marker even in a case where the catheters/probes use an imaging modality different from OCT, etc.) to facilitate computational detection of the marker in one or more images (e.g., X-ray images). One or more embodiments couple a software device or features (model) to hardware (e.g., an OCT probe, a probe/catheter using an imaging modality different from OCT while using a marker that is the same as or similar to the marker of an OCT probe/catheter, etc.). One or more embodiments may utilize animal data in addition to patient data. Training deep learning may use a large amount of data, which may be difficult to obtain from clinical studies. Inclusion of image data from pre-clinical studies in animals into a training set may improve model performance. Training and evaluation of a model may be highly data dependent (e.g., a way in which frames are selected (e.g., pullback only), split into training/validation/test sets, and grouped into batches as well as the order in which the frames, sets, and/or batches are presented to the model, any other data discussed herein, etc.). In one or more embodiments, such parameters may be more important or significant than some of the model hyper-parameters (e.g., batch size, number of convolution layers, any other hyper-parameter discussed herein, etc.). One or more embodiments may use a collection or collections of user annotations after introduction of a device/apparatus, system, and/or method(s) into a market, and may use post market surveillance, retraining of a model or models with new data collected (e.g., in clinical use), and/or a continuously adaptive algorithm/method(s).

One or more embodiments employ data annotation. For example, one or more embodiments may label pixel(s) representing a marker as well as pixels representing a blood vessel(s) at different phase(s) of a procedure/method (e.g., different levels of contrast due to intravascular contrast agent) of frame(s) acquired during pullback.

One or more embodiments employ incorporation of prior knowledge. For example, in one or more embodiments, a marker location may be known inside a vessel. As such, simultaneous localization of the vessel and marker may be used to improve marker detection. In one or more embodiments, a marker may move during a pullback inside a vessel, and such prior knowledge may be incorporated into the machine learning algorithm or the loss function.

One or more embodiments employ loss (cost) and evaluation function(s)/metric(s). For example, use of temporal information for model training and evaluation may be used in one or more embodiments. One or more embodiments may evaluate a distance between prediction and ground truth per frame as well as consider a trajectory of predictions across multiple frames of a time series.

Additional features that may be used in one or more embodiments of the present disclosure are discussed below:
Experiment #1

At least one embodiment of an overall process of machine learning is shown below:
  i. Create a dataset that contains both input and output;
  ii. Split the dataset into a training set and a testing set;
  iii. Select a model architecture and other hyper-parameters;
  iv. Train the model with the training set;
  v. Evaluate the trained model with the testing set; and
  vi. Repeat iv and v with new dataset(s).

Based on the testing results, steps i and iii may be revisited in one or more embodiments.

Step i: Create a Dataset that Contains Both Input and Output

To apply machine learning to marker detection or radiopaque marker detection in an angio image, input may be an original angio data, and output may be a marker-segmented image in one or more embodiments as aforementioned. In conducted experiments, segmentation was first performed by focusing only on the targeted radiopaque marker (i.e., the marker that is located or disposed at the distal optics) (see FIG. 17 showing an example input image on the left of FIG. 17 and a corresponding output image on the right of FIG. 17).

However, since one or more embodiments of a machine/device, system, method, storage medium, etc. may not be able to distinguish one marker from other markers (e.g., the marker on the catheter tip and/or the additional markers on the drive cable), the image in which all the markers in the frame were segmented was used as an output in experiment(s) (see FIG. 18 showing an example input image on the left of FIG. 18 and a corresponding output image after updating the segmentation on the right of FIG. 18).

Step ii: Split the Dataset into a Training Set and a Testing Set

To make this step easier, the frames in only one pullback were first segmented and used as the training set in at least one experiment. The frames from another pullback were used as the testing set in the experiment(s). While one or more embodiments may split the datasets in this way, one or more embodiments are not limited to this configuration.

Step iii: Select a Network Architecture and/or Architecture Model

At first, a U-net architecture, which may be used for image segmentation in a 2D image, was selected as a network architecture. One or more embodiments may incorporate or utilize a U-net architecture as discussed in "U-Net: Convolutional Networks for Biomedical Image Segmentation" to Olaf Ronnenberger, et al., Computer Science Department and BIOSS Centre for Biological Signalling Studies, In: Navab N., Hornegger J., Wells W., Frangi A. (eds) Medical Image Computing and Computer-Assisted Intervention, MICCAI 2015, Lecture Notes in Computer Science, vol 9351, Springer, Cham, published May 18, 2015 (https://arxiv.org/pdf/1505.04597.pdf), which is incorporated by reference herein in its entirety. However, in one or more experiments, the input and the output image size was downsized from 1024 pixel×1024 pixel to 512 pixel×512 pixel, and the trained network did not segment any markers in the testing data. However, while such experiment(s) were performed in such a fashion, one or more embodiments of the present disclosure are not limited to this configuration.

Then, another architecture "one hundred layers tiramisu" was selected as discussed above and as discussed in "The One Hundred Layers Tiramisu: Fully Convolutional DenseNets for Semantic Segmentation" to Simon Jégou, et al., Montreal Institute for Learning Algorithms, IEEE Conference on Computer Vision and Pattern Recognition Workshops (CVPRW), Honolulu, HI, pp. 1175-1183, published Oct. 31, 2017 (https://arxiv.org/pdf/1611.09326.pdf; doi: 10.1109/CVPRW.2017.156), which is incorporated by reference herein in its entirety. One of the advantages of this architecture in one or more embodiments is that it may be trained on a smaller region (224 pixel×224 pixel) and may be applied onto a bigger size when testing.

Figure 19:
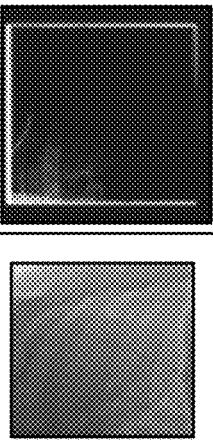
FIG. 19 shows original angio image frames with respective prediction results in accordance with one or more aspects of the present disclosure.

Step iv: Train the Network with the Training Set & Step v: Evaluate the Trained Network with the Testing Set First, the tiramisu network was trained with the training set, of which example is shown in FIG. 17. Although the trained network detected the markers, it detected the marker at the catheter tip with higher probability than the targeted markers in an experiment (FIG. 19, second column, where FIG. 19 shows original angio image frames with respective prediction results). As discussed above, since a machine, device, system, storage medium, method, etc. may not distinguish the different markers in the images, the network was re-trained with the training set, of which example is shown in FIG. 18. The trained network detected the markers better with less detection of background noise, but it still detected the marker at the catheter tip with higher probability than the targeted markers (FIG. 19, third column).

To improve the network, variations were added to the training set. As the variations used, vertical flip, horizontal flip, and image contrast adjustment were performed to the training set. In addition to this, the number of iterations was increased. An improvement was observed: the re-trained network detected the targeted marker with similar probability as the one for the marker at the catheter tip (FIG. 19, fourth column). While the network detected other markers (the additional markers on the drive cable), the network also detected the guidewire and/or the dense contrast media location with relatively-high probability. Therefore, it would be useful to include these images more in the training set in one or more embodiments.

Experiment #2

At least one embodiment of an overall process of machine learning is shown below:
  i. Create a dataset that contains both input and output;
  ii. Split the dataset into a training set and a testing set;
  iii. Select a model architecture and other hyper-parameters;
  iv. Train the model with the training set;
  v. Evaluate the trained model with the testing set; and
  vi. Repeat iv and v with new dataset(s).

Based on the testing results, steps i and iii may be revisited in one or more embodiments.

Observations and details regarding additional experiments conducted are discussed below.

Step i: Create a Dataset that Contains Both Input and Output

To apply machine learning to radiopaque marker detection in the angio image, input may be an original angio data, and output may be the marker-segmented image as aforementioned. The image that all the markers in the frame were segmented was used as an output (FIG. 20 showing at least one embodiment example of an input image on the left side of FIG. 20 and the corresponding output image on the right side of FIG. 20).

Step ii: Split the Dataset into a Training Set and a Testing Set

First, the frames in three pullbacks (different C-arm setting, different vessel) were used as training data. Then, the frames in all 20 pullbacks were used as training data.

Step iii: Select a Network Architecture and/or an Architecture Model

Architecture "one hundred layers tiramisu" was selected as discussed in "The One Hundred Layers Tiramisu: Fully Convolutional DenseNets for Semantic Segmentation" to Simon Jégou, et al., Montreal Institute for Learning Algorithms, IEEE Conference on Computer Vision and Pattern Recognition Workshops (CVPRW), Honolulu, HI, pp. 1175-1183, published Oct. 31, 2017 (https://arxiv.org/pdf/1611.09326.pdf; doi: 10.1109/CVPRW.2017.156), which is incorporated by reference herein in its entirety. One of the advantages of this architecture in one or more embodiments is that it may be trained on a smaller region (224 pixel×224 pixel) and may be applied onto a bigger size when testing.

Step iv: Train the Network with the Training Set & Step v: Evaluate the Trained Network or Trained Model with the Testing Set <3 Pullbacks Data>

Different parameters were used for training:
  Batch size: 16 or 4
  Training image size: 224 pixel×224 pixel (see e.g., "The One Hundred Layers Tiramisu: Fully Convolutional DenseNets for Semantic Segmentation" to Simon Jégou, et al.), 128 pixel×128 pixel, 448 pixel×448 pixel
  Steps/epoch (iteration): 100
  Epochs (iterations): 1000

Figure 21:
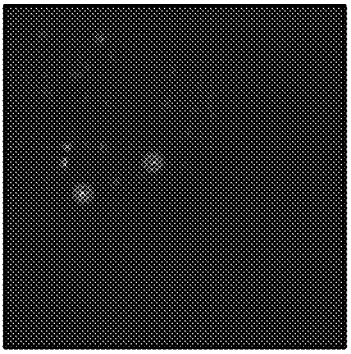
FIG. 21 shows example prediction results with different trained models in accordance with one or more aspects of the present disclosure.

FIG. 21 shows examples of prediction result(s) with different training models. When the batch size was decreased, the model appeared to have reduced prediction accuracy. To improve the prediction with a smaller batch size, the model may be trained longer (e.g., increase the number of steps/epoch and the number of epochs). On the other hand, when the training image size was changed, the prediction result had less noise, but may have missed the targeted marker (the marker at the distal optics) more often than the original training image size. Therefore, for further training, the batch size and the training image size was set as 16 and 224 pixel×224 pixel.

<20 Pullbacks Data>

When a model was started training with 20 pullbacks data, its estimated time was >2 weeks. Therefore, the training was performed by splitting the input data into 3-4 pullbacks data and by training the same model over and over with different input data for 6 rounds. Table 1 below shows which pullback data was used for which round of training. Each round of training needed about 12-15 hours in the experiments conducted.

TABLE 1

Information of pullbacks that are assigned for each training

| Animal # | Pullback name | Angle | Training round | | | | |
|---|---|---|---|---|---|---|---|
| 49263 | RCA08 | LAO 20, CRA 0 | 2 | | | | |
| 49263 | RCA09 | LAO 20, CRA 0 | | 3 | | | |
| 49263 | RCA10 | LAO 20, CRA 0 | | | 4 | | |
| 49263 | RCA12 | LAO 20, CRA 0 | | | | 5 | |
| 49263 | RCA16 | LAO 20, CRA 0 | 2 | | | | |
| 49263 | RCA21 | LAO 20, CRA 0 | | | | | 6 |
| 49263 | RCA27 | LAO 20, CRA 0 | | | | 5 | |
| 49263 | RCA30 | LAO 20, CRA 0 | | | | | 6 |
| 49263 | RCA31 | LAO 20, CRA 0 | | 3 | | | |
| 49263 | RCA36 | LAO 20, CRA 0 | | | 4 | | |
| 49263 | RCA40 | RAO 1, CAU 34 | 1 | | | | |
| 49263 | RCA41 | LAO 22, CRA 0 | 1 | | | | |
| 49263 | LCX43 | RAO 60, CAU 0 | 1 | | | | |
| 49263 | LCX44 | LAO 48, CRA 25 | 1 | | | | |
| 49263 | LCX45 | RAO 54, CRA 10 | | 3 | | | |
| 49263 | LCX46 | LAO 52, CRA 24 | | | 4 | | |
| 49263 | LCX47 | LAO 52, CRA 24 | | | | 5 | |
| 49263 | LCX54 | RAO 62, CRA 0 | | | | | 6 |
| 49263 | LCX55 | RAO 62, CRA 0 | 2 | | | | |
| 49263 | LCX57 | LAO 52, CRA 25 | 2 | | | | |

Figure 22:
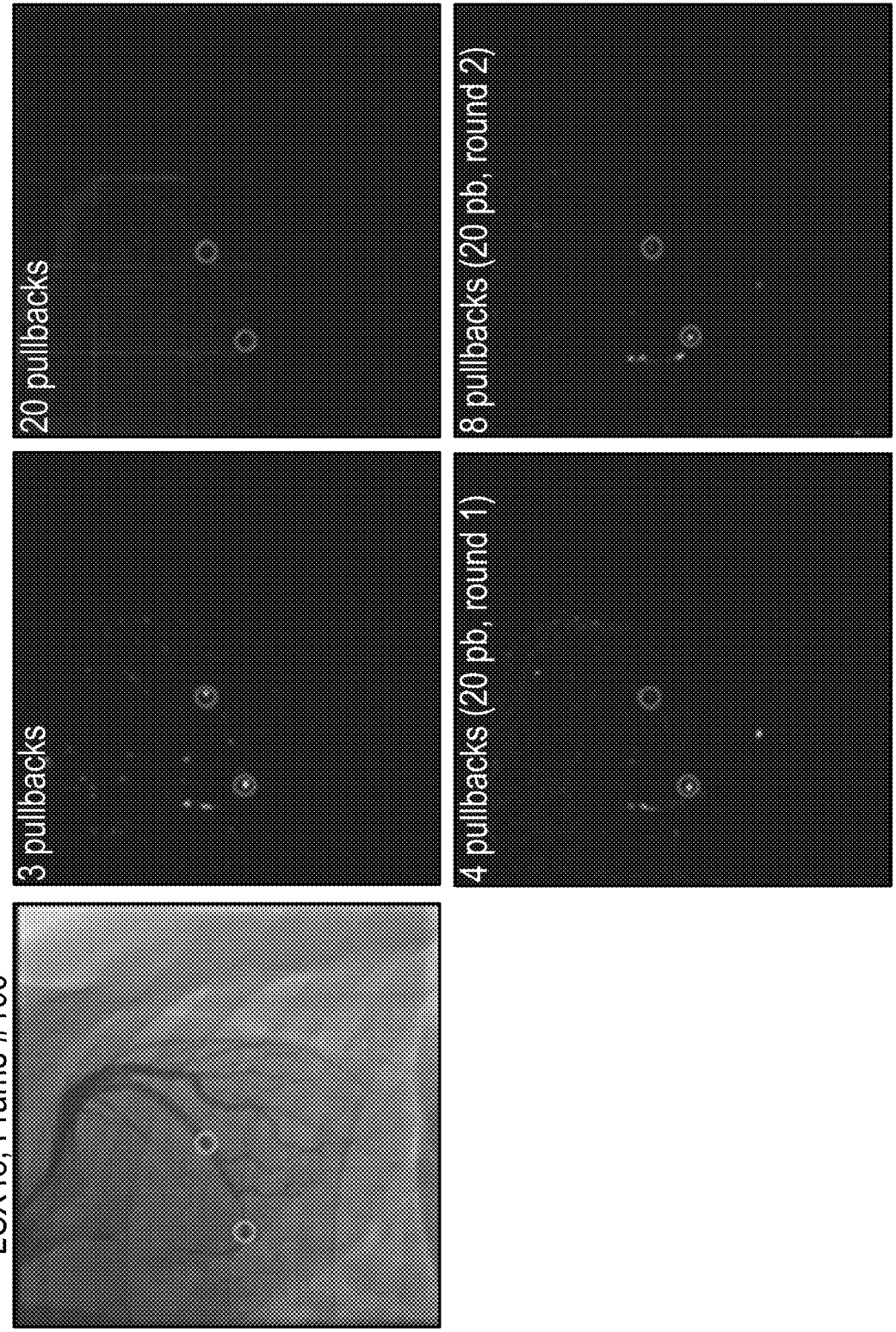
FIG. 22 shows example prediction results with four different models in accordance with one or more aspects of the present disclosure.
Figure 24:
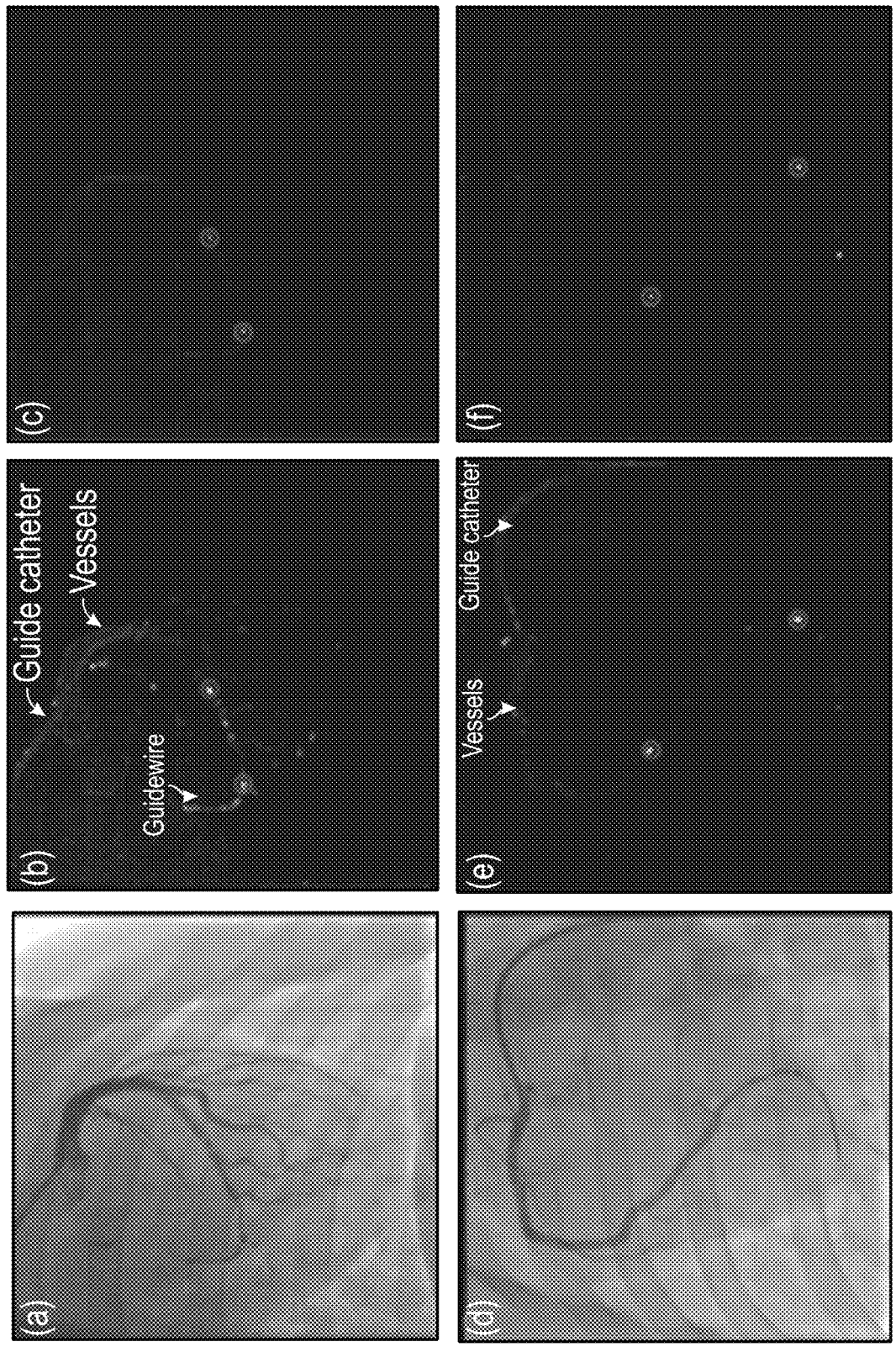
FIGS. 24 (a)-(f) show respective example figures of prediction results in accordance with one or more aspects of the present disclosure.

FIG. 22 shows at least one embodiment example of prediction results with four different models. Top row of FIG. 22 shows the example prediction results with the models trained with 3 pullbacks data and with 20 pullbacks data. As shown here, the prediction result with the model with 20 pullbacks data predicted the marker with less accuracy. This may be because of overfitting. As summarized in Table 1, out of 20 pullbacks, 12 pullbacks were performed in right coronary artery (RCA) with same C-arm setting for ii pullbacks. Out of 8 pullbacks in a left circumflex branch (LCX), half of them were acquired in the same C-arm setting and the other half were acquired in another C-arm setting. To understand the influence of this, the prediction was performed using the models after round 1 and round 2. The example prediction results are shown in the bottom row of FIG. 22. These images in FIG. 22 suggest the possibility of overfitting of the model with a lot of data that contains quite similar images.

Experiment #3

At least one embodiment of an overall process of machine learning is shown below:
 i. Create a dataset that contains both input and output;
 ii. Split the dataset into a training set and a testing set;
 iii. Select a model architecture and other hyper-parameters;
 iv. Train the model with the training set;
 v. Evaluate the trained model with the testing set; and
 vi. Repeat iv and v with new dataset(s).

Based on the testing results, steps i and iii may be revisited in one or more embodiments.

Observations and details regarding additional experiments conducted are discussed below.

[Segmentation Model] Example

Step i: Create a Dataset that Contains Both Input and Output

For segmentation model(s), input is an original angio data, and output is the marker-segmented image. The image that all the markers in the frame were segmented was used as an output (FIG. 23 shows at least one embodiment example of an input image on the left side of FIG. 23 and a corresponding output image on the right side of FIG. 23).

Step ii: Split the Dataset into Training Set and Testing Set

The frames in all 20 pullbacks from animal study #1 were used as training data.

Step iii: Select a Network Architecture and/or Architecture Model

Architecture "one hundred layers tiramisu" was selected as discussed in "The One Hundred Layers Tiramisu: Fully Convolutional DenseNets for Semantic Segmentation" to Simon Jégou, et al., Montreal Institute for Learning Algorithms, IEEE Conference on Computer Vision and Pattern Recognition Workshops (CVPRW), Honolulu, HI, pp. 1175-1183, published Oct. 31, 2017 (https://arxiv.org/pdf/1611.09326.pdf; doi: 10.1109/CVPRW.2017.156), which is incorporated by reference herein in its entirety. One of the advantages of this architecture in one or more embodiments is that it may be trained on a smaller region (224 pixel×224 pixel) and may be applied onto a bigger size when testing.

Step iv: Train the Network with the Training Set & Step v: Evaluate the Trained Network or Trained Model with the Testing Set <20 Pullbacks Data from Animal Study #1>

Different parameters were used for training:
 Batch size: 16
 Training image size: 224 pixel×224 pixel (see e.g., "The One Hundred Layers Tiramisu: Fully Convolutional DenseNets for Semantic Segmentation" to Simon Jégou, et al.)
 Steps/iteration: 200
 Iterations: 5000 (Iterations may be limited based on memory size resources available or processing preferences (e.g., a preferred timeline for completed processing, a success rate threshold, etc.). For example, while the iterations used was set to 5000, the success rate obtained used training that was terminated at the $4,923^{rd}$ iteration.)

Example prediction results are shown in FIGS. 24(a)-(f). As shown in FIGS. 24(a)-(f), better prediction with less noise may be obtained with longer training time. Similar result(s) was/were observed when testing with angio data from animal study #2. FIGS. 24 (a) and (d) show Original images (Image contrast has been adjusted to show markers better). FIGS. 24 (b) and (e) show Predicted result(s) (i.e., probability map(s)) with the model trained 1000 iterations. FIGS. 24 (c) and (f) show Predicted result(s) (i.e., probability map(s)) with the model trained over 4500 iterations. At least one circle "0" in FIG. 24 represents a stationary marker at the catheter tip (where this O is the low right circles in FIGS. 24 (d)-(f), and the left circles in FIGS. 24 (a)-(c)). At least one circle "O" in FIG. 24 represents a targeted marker at the distal optics (where this O is the top left circles in FIGS. 24 (d)-(f), and the right circles in FIGS. (a)-(c)).

[Regression Model] Example

Step i: Create a Dataset that Contains Both Input and Output

For one or more regression model embodiments, input may be the original angio data (1024 pixel×1024 pixel), and the output may be the centroid coordinates of two markers (target marker and stationary marker) (FIG. 25 showing an example input image on the left side of FIG. 25 and showing a corresponding output image on the right side of FIG. 25).

Step ii: Split the Dataset into a Training Set, a Validation Set, and a Testing Set Since there is a limited number of data available in one or more embodiments, all the data may be used either as a training set or a validation set. To evaluate the efficiency of each model that has different parameters, the separation of the training set from the validation set was performed before training any model, and was used for all the models to be trained.

Step iii: Select a Network Architecture

Architecture was originally created by the inventor(s) based on Residual Network (ResNet) architecture (see e.g., "The One Hundred Layers Tiramisu: Fully Convolutional DenseNets for Semantic Segmentation" to Simon Jégou, et al., which is incorporated by reference herein in its entirety). The model itself has/included hyper-parameters (i.e., parameters of the model architecture) to be tested at Step iv. The created architecture of a regression model is shown in FIG. 26 (see also, FIG. 9A and aforementioned discussion of FIG. 9A).

Step iv: Train the Network with the Training Set & Step v: Evaluate the Trained Network or Model with the Testing Set <31 Pullbacks Data for Training, 7 Pullbacks for Validation; from Animal Studies #1 and/or #2>

Hyper-parameters:

Depth (i.e., # of layers)

Width (i.e., # of filters): Fixed in one or more embodiments

Batch size (i.e., # of training images/step): In one or more embodiments, may be >4

Learning rate (i.e., a hyper-parameter that controls how fast the weights of a neural network (the coefficients of regression model) are adjusted with respect to the loss gradient)

Dropout (i.e., % of neurons (filters) that are dropped at each layer)

Optimizer: for example, Adam optimizer or Stochastic gradient descent (SGD) optimizer Other fixed hyper-parameters (constants):

Input size: 1024 pixel×1024 pixel (Original image size)

Epochs: 500

Number of models trained with different hyper-parameter configurations: 10

FIG. 27 shows the results of at least one hyper-parameter search. Model a04 shows the decrease both in training loss and validation loss. By comparing the hyper-parameters (Table 2 shown below), Model a04 and Model a05, both of which have lower training loss and validation loss than others, used a similar value for dropout and used the same optimizer (SGD optimizer). Therefore, it may be concluded that this regression model should use an SGD optimizer with dropout feature. The line for am is slightly above the line for a03 in the training loss graph on the left side of FIG. 27. Also, a07-a09 are overlapping each other in the graph on the right side of FIG. 27. As a next step, another hyper-parameter search with a fixed optimizer and with a different width may be performed. A model architecture for this scenario is shown in FIG. 28.

TABLE 2

List of hyper-parameters that are used for each model

| Model ID | Depth d1 | d2 | d3 | Width (fixed) | Dropout Yes/No | % | Optimizer | Learning rate |
|---|---|---|---|---|---|---|---|---|
| a01 | 1 | 5 | 2 | 64 | Yes | 42.4 | 'adam' | 0.0410 |
| a02 | 5 | 5 | 3 | 64 | No | n/a | 'adam' | 0.9023 |
| a03 | 3 | 0 | 0 | 64 | No | n/a | 'adam' | 0.1201 |
| a04 | 1 | 0 | 3 | 64 | Yes | 60.9 | 'sgd' | 0.7303 |
| a05 | 4 | 2 | 4 | 64 | Yes | 60.2 | 'sgd' | 0.9252 |
| a06 | 3 | 3 | 4 | 64 | No | n/a | 'adam' | 0.1244 |
| a07 | 4 | 1 | 1 | 64 | No | n/a | 'adam' | 0.9662 |
| a08 | 2 | 1 | 5 | 64 | No | n/a | 'adam' | 0.0680 |
| a09 | 3 | 4 | 4 | 64 | No | n/a | 'adam' | 0.4356 |
| a10 | 2 | 5 | 2 | 64 | Yes | 94.6 | 'sgd' | 0.4084 |

One or more embodiments may use one or more features for a regression model as discussed in "Deep Residual Learning for Image Recognition" to Kaiming He, et al., Microsoft Research, Dec. 10, 2015 (https://arxiv.org/pdf/1512.03385.pdf), which is incorporated by reference herein in its entirety.

Experiment #4

Coregistration

Available Dataset

The following tables 3A and 3B show the data set that was used for this experiment:

| | # of pullbacks | # of frames with contrast | # of frames during pullback |
|---|---|---|---|
| ANIMAL | | | |
| TOTAL | 38 | 4496 | 2265 |
| RCA | 17 (44.7%) | 2109 (46.9%) | 1033 (45.6%) |
| LCX | 11 (28.9%) | 1309 (29.1%) | 657 (29.0%) |
| LAD | 5 (13.2%) | 599 (13.3%) | 313 (13.8%) |
| Left subclavian | 5 (13.2%) | 479 (10.7%) | 262 (11.6%) |
| CLINICAL | | | |
| TOTAL | 45 | 2470 | 2531 |
| RCA | 12 (26.7%) | 502 (20.3%) | 657 (26.0%) |
| LCX | 4 (8.9%) | 151 (6.1%) | 108 (4.3%) |
| LAD | 29 (64.4%) | 1817 (73.6%) | 1766 (69.8%) |

1. An Image Processing-Based Algorithm with a User-Specified Pullback Region

An image processing-based algorithm where a user specifies a pullback region on one (i) frame was tested on the clinical data. The marker detection success rate was compared to that of animal study data. The marker detection success rate on clinical data was not as high as that on animal study data (see Method 1 of FIG. 5). The observation revealed that at least one of the candidate points was located close enough to the actual location in 70-80% of the frames in each pullback; therefore, the subject image processing-based algorithm needs to be improved to select the best point from the candidate points.

As aforementioned, examples of different marker detection success rate are shown in FIG. 5. While marker detection success rate may be calculate in various ways, one example of a marker detection success rate is to calculate a number of frames that the detected and the actual radiopaque marker locations are the same divided by the number of total frames obtained, received, or imaged during the OCT pullback. According to a first method where a user specifies a pullback region on one frame, according to a second method where a user points out marker location on several or multiple frames, and according to a third method where a user specifies a pullback region on multiple frames, several success rates are shown for three categories of data in FIG. 5 to highlight success rate variation(s). Additionally, coregistration success rates (based on user interviews) may be successful in 80% of cases or higher. From experiments, candidate points include the actual marker location in at least 80-90% of total clinical angiography images using one or more features of the present disclosure. Indeed, by applying machine or deep learning as discussed herein, marker detection success rates and coregistration success rates may be improved or maximized. The success rate of marker detection (and leading to success rate of coregistration) may depend on how good the estimation of a marker location is. As such, by improving estimation of the marker location, the success rate of the marker detection may be improved and likewise the success rate of co-registration may be improved.

Application of Machine Learning

At least one embodiment of an overall process of machine learning is shown below:
  i. Create a dataset that contains both images and corresponding ground truth labels;
  ii. Split the dataset into a training set and a testing set;
  iii. Select a model architecture and other hyper-parameters;
  iv. Train the model with the training set;
  v. Evaluate the trained model with the validation set; and
  vi. Repeat iv and v with new dataset(s).

Based on the testing results, steps i and iii may be revisited in one or more embodiments.

Observations and details regarding additional experiments conducted are discussed below.

[2A. Segmentation Model]

Since the output from this model, in one or more embodiments, is a "probability" of each pixel that may be categorized as a marker or not, post-processing after prediction via the trained segmentation model may be developed to better define, determine, or locate the final coordinate of marker location.

After predicting the probability on clinical data using the previously trained segmentation model (the training was performed using all animal study data), the post-processing algorithm shown in FIG. 7 and as discussed above was applied to the predicted probability result. In this post-processing algorithm, a user is asked to define where in the vessel OCT pullback was performed in a manner similar to the aforementioned Method 1 for the image processing-based algorithm, where a user specifies a pullback region on one (i) frame was tested on the clinical data.

One or more embodiments of a semantic segmentation model may be performed using the One-Hundred Layers Tiramisu method discussed in "The One Hundred Layers Tiramisu: Fully Convolutional DenseNets for Semantic Segmentation" to Simon Jégou, et al., Montreal Institute for Learning Algorithms, published Oct. 31, 2017 (https://arxiv.org/pdf/1611.09326.pdf), which is incorporated by reference herein in its entirety.

The marker detection success rate was assessed after post-processing in a manner similar to the aforementioned Method 1 for the image processing-based algorithm, where a user specifies a pullback region on one (i) frame was tested on the clinical data. As shown in FIG. 8 (which compares marker detection success rates on clinical data between machine learning-based algorithm (segmentation model) and other image processing-based algorithms not using machine learning), the marker detection success rate was increased about 16% on average of or for all the pullbacks. For each pullback, the marker detection success rate was increased in 40 out of 45 pullbacks (88.9%) compared with Method 1 and in 39 out of 45 pullbacks (86.7%) compared with Method 3 (see FIG. 8).

Although the post-processing algorithm may be refined or further refined and the segmentation model may be trained to include clinical data, this result shows that the critical improvement of a marker detection success rate(s) may be achieved using machine learning/deep learning in accordance with one or more features of the present disclosure.

[2B. Regression Model]

Step i: Create a Dataset that Contains Both Input and Output

For regression model(s), the input may be the entire angiography image frame, and the output may be the centroid coordinates of radiopaque markers (target marker and stationary marker, if necessary/desired) (FIG. 29 shows an example of an input image on the left side of FIG. 29 and a corresponding output image on the right side of FIG. 29).

Step ii: Split the Dataset into a Training Set, a Validation Set, and a Testing Set Since there is a limited number of data available in one or more embodiments, all the data may be used either as part of a training set or a validation set (For this experiment, only animal study data was used, so test data set was not set apart). To evaluate the efficiency of each model that has different parameters, the separation of the training set from the validation set was performed before training any model, and the same separation was used for all the models to be trained.

Step iii: Select a Network Architecture

Figure 30:
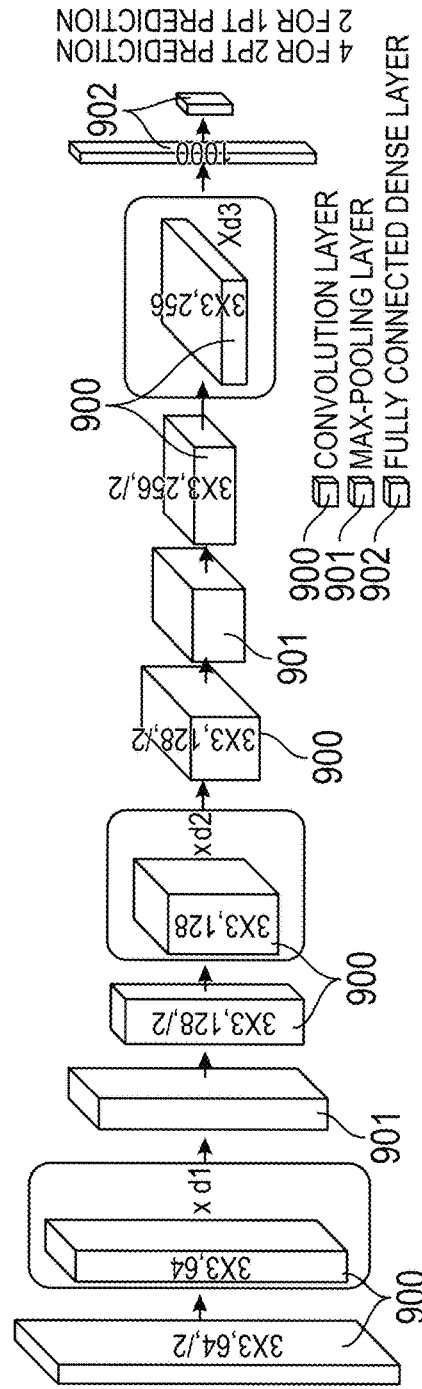
FIG. 30 shows a created architecture of or for a regression model(s) in accordance with one or more aspects of the present disclosure.

Architecture was originally created by the inventor(s) based on Residual Network (ResNet) architecture (see e.g., "The One Hundred Layers Tiramisu: Fully Convolutional DenseNets for Semantic Segmentation" to Simon Jégou, et al., which is incorporated by reference herein in its entirety). The model itself has/included hyper-parameters (i.e., parameters of the model architecture) to be tested at Step iv. The created architecture of the regression model is shown in FIG. 30 (see also, aforementioned discussion of FIG. 9A and FIG. 9A).

Step iv: Train the Network and/or Model with the Training Set

Data Split
    Training: 30 pullbacks of animal study, 37 pullbacks of clinical data
    Validation: 400 frames from 8 pullbacks of animal study and 8 pullbacks of clinical data
  Hyper-parameters:
    Depth (i.e., # of layers)
    Width (i.e., # of filters)
    Batch size (i.e., # of training images/step): May be >4 in one or more embodiments
    Learning rate (i.e., a hyper-parameter that controls how fast the weights of a neural network (the coefficients of regression model) are adjusted with respect the loss gradient)
    Dropout (i.e., % of neurons (filters) that are dropped at each layer)
    Optimizer: for example, Adam optimizer or Stochastic gradient descent (SGD) optimizer
  Other fixed hyper-parameters (constants):
    Input size: 1024 pixel×1024 pixel or 512 pixel×512 pixel
    Epochs: 500 (for additional training, iteration was set as 3000)
    Number of models trained with different hyper-parameter configurations: 10

Since the image sizes are different between animal study data (1024 pixel×1024 pixel) and clinical data (512 pixel× 512 pixel), the input image may be upsampled (for clinical data) or downsampled (for animal data) to match all the input image size to include clinical data as part of training and validation.

Figure 31:
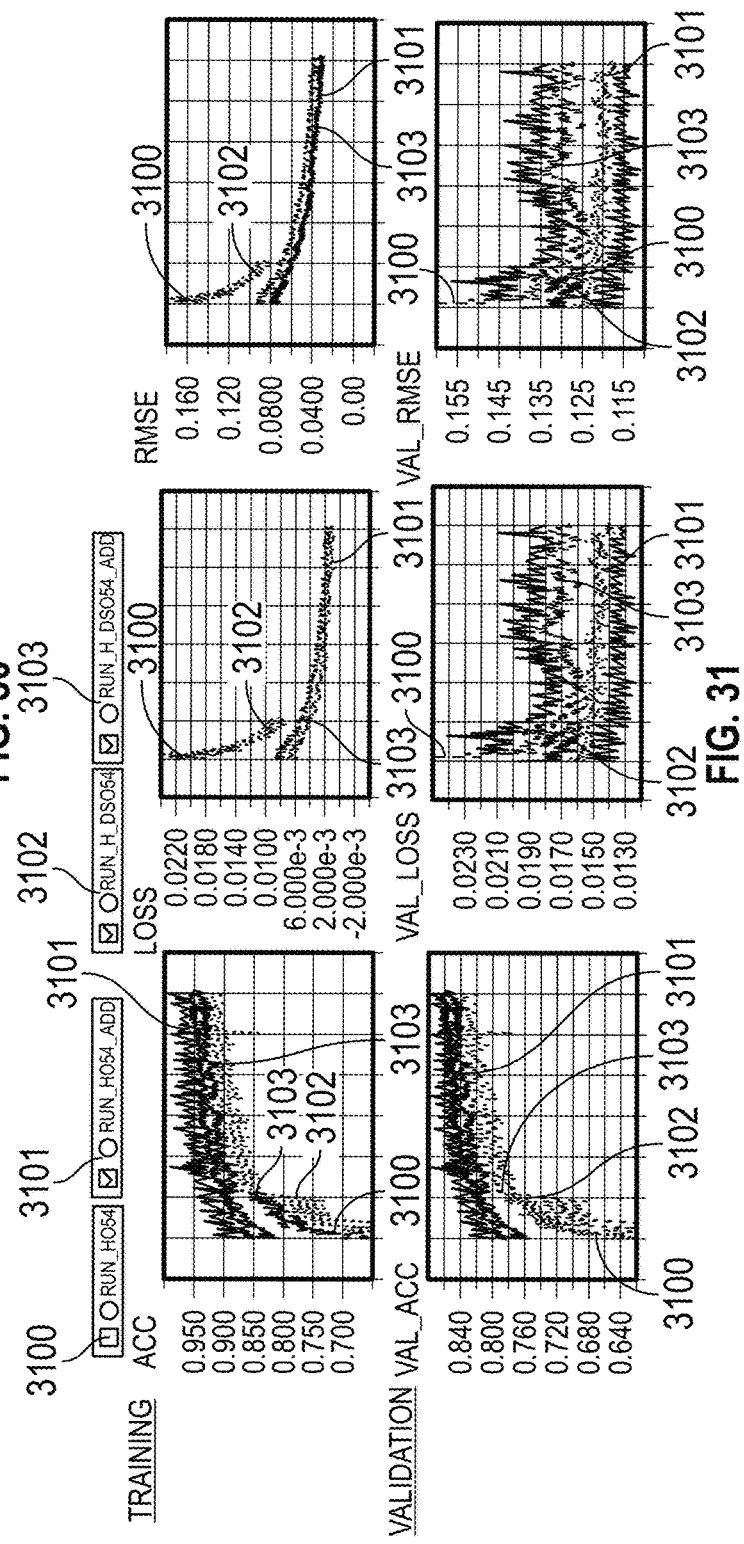
FIG. 31 shows training and validation result(s) over iterations in accordance with one or more aspects of the present disclosure.
Figure 32:
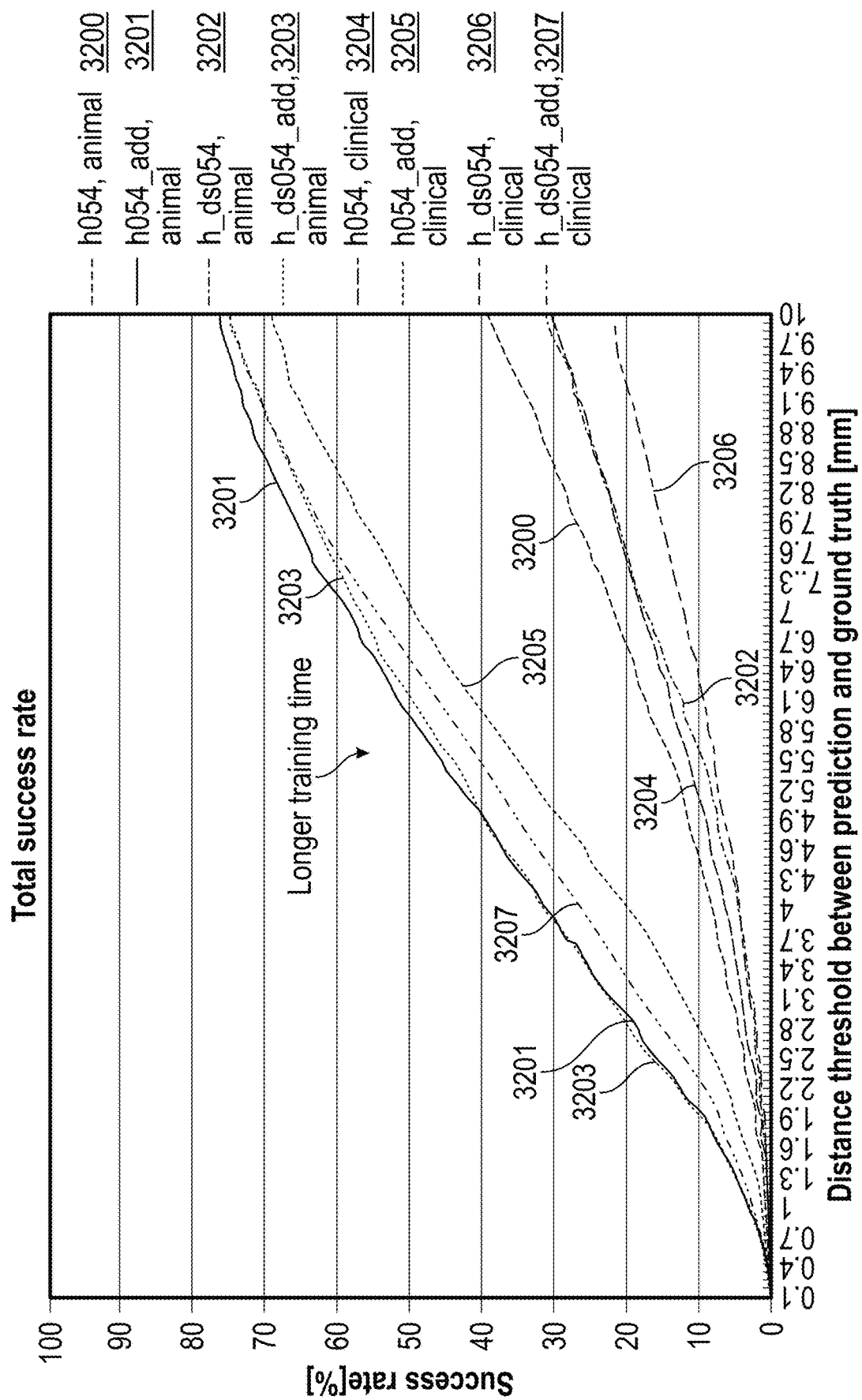
FIG. 32 shows total marker detection success rate with different distance threshold(s) between prediction and ground truth in accordance with one or more aspects of the present disclosure.

Step v: Evaluate the Trained Network or Model with the Testing Set (1) Influence of Upsampling and Downsampling As shown in Table 3, FIG. 31, and FIG. 32, no significant difference was observed between upsampling and downsampling in the conducted experiment(s). Since downsampling is similar to max-pooling (one of image processing methods that is often used in machine learning model architecture; gray layer(s) 901 in FIG. 30), further training may be performed with downsampling, e.g., the input image size may be 512 pixel×512 pixel. FIG. 31 shows training and validation result(s) over iterations in experiments performed (see run_h054 results 3100, see run_h054_add results 3101, see run_h_ds054 results 3102, and see run_h_ds054_add results 3103 in FIG. 31). FIG. 32 shows total marker detection success rate with a different distance threshold between prediction and ground truth (see h054, animal data 3200; h054_add, animal data 3201; h_ds054, animal data 3202; h_ds054_add, animal data 3203; h054, clinical data 3204; h054_add, clinical data 3205; h_ds054, clinical data 3206; and h_ds054_add, clinical data 3207).

software or one or more programs allow a processor or computer to carry out operation(s) of the processes described in the present disclosure.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/0101374, and 2016/0228097, and WO 2016/144878, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative

TABLE 4

Training result of h054, h054_add (upsampling), h_ds054, h_ds054_add (downsampling)

| Model ID | Data for training | D1 | D2 | D3 | Total # of conv layers | Width | Dropout value | Optimizer | Learning rate | Batch size | Loss (MSE) | RMSE | Validation loss (MSE) | Validation RMSE |
|---|---|---|---|---|---|---|---|---|---|---|---|---|---|---|
| h054 Upsample | animal + clinical | 4 | 0 | 0 | 8 | 64 | 0.071 | Adam | 7.71E−05 | 12 | 0.0071 | 0.0826 | 0.0158 | 0.1240 |
| h054_add Upsample | animal + clinical | 4 | 0 | 0 | 8 | 64 | 0.071 | Adam | 7.71E−05 | 12 | 8.0E−04 | 0.0272 | 0.0150 | 0.1211 |
| h_ds054 Downsample | animal + clinical | 4 | 0 | n/a | 8 | 64 | 0.071 | Adam | 7.71E−05 | 12 | 0.0081 | 0.0886 | 0.0170 | 0.1290 |
| h_ds054_add Downsample | animal + clinical | 4 | 0 | n/a | 8 | 64 | 0.071 | Adam | 7.71E−05 | 12 | 0.0018 | 0.0409 | 0.0169 | 0.1279 |

Other Parameters:

[Next Steps] As aforementioned, next steps may include, but are not limited to, the following:

For Segmentation model(s): Train a model with clinical data

For Regression model(s): Split the dataset into training, validation, and test, and assess to which extent the model may/can generalize to unseen data.

One or more features discussed herein may be determined using a convolutional auto-encoder, Gaussian filters, Haralick features, and/or thickness or shape of the sample or object.

One or more embodiments of the present disclosure may use machine learning to determine marker location, to perform coregistration and/or to perform any other feature discussed herein. Machine learning is a field of computer science that gives processors the ability to learn, via artificial intelligence. Machine learning may involve one or more algorithms that allow processors or computers to learn from examples and to make predictions for new unseen data points. In one or more embodiments, such one or more algorithms may be stored as software or one or more programs in at least one memory or storage medium, and the embodiments and that other arrangements may be devised without departing from the spirit and scope of the present disclosure. The scope of the following claims is to be accorded the broadest interpretation so as to encompass all such modifications and equivalent structures and functions.

What is claimed is:

1. A detection apparatus using artificial intelligence, the apparatus comprising:
one or more processors that operate to:
acquire or receive angiography image data;
receive a trained model or load a trained model from a memory, the trained model being trained using artificial intelligence;
apply the trained model to the acquired or received angiography image data;
select one angiography frame of one or more angiography frames of the acquired or received angiography image data after the trained model has been applied;
detect a marker location on the selected angiography frame with the trained model, the detected marker location defining detected results;
check whether the marker location is correct or accurate based on the trained model or based on an input or inputs received or obtained by the apparatus;

in an event that the marker location is not correct or accurate, then modify the detected results or the detected marker location based on the trained model or based on an input or inputs received or obtained by the apparatus, and repeat the check as to whether the marker location is correct or accurate, or in an event that the marker location is correct or accurate, then check whether all of the angiography frames of the one or more angiography frames have been checked for correctness or accuracy; and in an event that all of the angiography frames have not been checked for correctness or accuracy, then select another angiography frame of the one or more angiography frames and repeat the detection of a marker location and the check of whether the marker location is correct or accurate or not for the another angiography frame.

2. The apparatus of claim 1, wherein the one or more processors further operate to one or more of the following:
(i) in an event that all of the angiography frames have been checked for correctness or accuracy, then perform coregistration based on the detected marker location;
(ii) display the detected marker location on a display;
(iii) display the detected marker location on the display such that the detected marker location is overlayed on angiography data;
(iv) display the modified detected results and/or the modified marker location on the display;
(v) control an intravascular imaging catheter that has a marker or radiopaque marker such that the intravascular imaging catheter is inserted into an object or sample; and/or
(vi) acquire or receive the angiography image data during a pullback operation of an intravascular imaging catheter that has a marker or radiopaque marker where the pullback operation is controlled by the one or more processors operating to control the intravascular imaging catheter.

3. The apparatus of claim 2, wherein the object or sample includes one or more of the following: a vessel, a target specimen or object, and/or a patient.

4. The apparatus of claim 2, wherein the one or more processors further operate to use one or more neural networks or convolutional neural networks to perform one or more of the following: the load of the trained model, the selection of the angiography frame, the detection of the marker location for each frame, the determination of whether the detected marker location is accurate or correct based on the trained model or based on an input or inputs received or obtained by the apparatus, the modification of the detected results or the detected marker location for each frame, the display of the detected marker location on the display, the performance of the coregistration, the control of an intravascular imaging catheter such that the intravascular imaging catheter is inserted into the object or sample, and/or the acquiring or receiving of the angiography image data during the pullback operation.

5. The apparatus of claim 2, wherein the one or more processors further operate to perform the coregistration by co-registering the acquired or received angiography image and an obtained one or more Optical Coherence Tomography (OCT) or Intravascular Ultrasound (IVUS) images or frames or an obtained one or more images or frames of another imaging modality.

6. The apparatus of claim 2, wherein the loaded, trained model is one or a combination of the following: a segmentation model, a segmentation model with post-processing, a model with pre-processing, a model with post-processing, a segmentation model with pre-processing, a deep learning or machine learning model, a semantic segmentation model or classification model, an object detection or regression model, an object detection or regression model with pre-processing or post-processing, a combination of a semantic segmentation model and an object detection or regression model, a model using repeated segmentation model technique(s), a model using feature pyramid(s), a model using repeated object detection or regression model technique(s), a deep convolutional neural network model, a recurrent neural network model with long short-term memory that can take temporal relationships across images or frames into account, a model that can take temporal relationships across images or frames into account, a model that can take temporal relationships into account including marker movement(s) or location(s) during pullback in a vessel, a model that can use prior knowledge about a procedure and incorporate the prior knowledge into the machine learning algorithm or loss function, a model using feature pyramid(s) that can take different image resolutions into account, and/or a model using residual learning technique(s).

7. The apparatus of claim 2, wherein the one or more processors further operate to perform one or more of the following:
(i) display the angiography data along with an image for each of one or more imaging modalities on the display, wherein the one or more imaging modalities include one or more of the following: a tomography image; an Optical Coherence Tomography (OCT) image; a fluorescence image; a near-infrared fluorescence (NIRAF) image; a near-infrared fluorescence (NIRAF) in a predetermined view, a carpet view, and/or an indicator view; a three-dimensional (3D) rendering; a 3D rendering of a vessel; a 3D rendering of a vessel in a half-pipe view or display; a 3D rendering of the object; a lumen profile; a lumen diameter display; a longitudinal view; computer tomography (CT); Magnetic Resonance Imaging (MRI); Intravascular Ultrasound (IVUS); an X-ray image or view; and/or an angiography view; and/or
(ii) change or update the displays for the angiography data along with each of the one or more imaging modalities based on the modified detection results and/or the modified marker location.

8. A method for training a model using artificial intelligence, the trained model to be used by a detection apparatus using artificial intelligence, the method comprising:
acquiring or receiving angiography image data;
establishing ground truth for at least one or more markers, one or more radiopaque markers, or one or more marker locations in the acquired angiography image data;
splitting the acquired angiography image data into training, validation, and test sets or groups;
choosing one or more hyper-parameter values for model training, the one or more hyper-parameter values including at least one or more of the following: model architecture, learning rate, and initialization of parameter values;
training a model with data in the training set or group and evaluate the model with data in the validation set or group;
determining whether the performance of the trained model is sufficient; and
in the event that the performance of the trained model is not sufficient, then repeating the procedures for choosing one or more hyper-parameter values, model training and evaluating, and determining, or, in the event that the performance of the trained model is sufficient, selecting the trained model and saving the trained model to a memory, wherein the method further includes or uses:

a detection apparatus using artificial intelligence, the apparatus comprising:
one or more processors that operate to:
acquire or receive angiography image data;
receive the trained model or load the trained model from the memory, the trained model being trained using artificial intelligence;
apply the trained model to the acquired or received angiography image data;
select one angiography frame of one or more angiography frames of the acquired or received angiography image data after the trained model has been applied;
detect a marker location on the selected angiography frame with the trained model, the detected marker location defining detected results;
check whether the marker location is correct or accurate based on the trained model or based on an input or inputs received or obtained by the apparatus;
in an event that the marker location is not correct or accurate, then modify the detected results or the detected marker location based on the trained model or based on an input or inputs received or obtained by the apparatus, and repeat the check as to whether the marker location is correct or accurate, or in an event that the marker location is correct or accurate, then check whether all of the angiography frames of the one or more angiography frames have been checked for correctness or accuracy; and
in an event that all of the angiography frames have not been checked for correctness or accuracy, then select another angiography frame of the one or more angiography frames and repeat the detection of a marker location and the check of whether the marker location is correct or accurate or not for the another angiography frame.

9. The method of claim 8, wherein one or more of the following:
(i) the parameters include one or more hyper-parameters;
(ii) the saved, trained model is used as a created identifier or detector for identifying or detecting a marker(s) or radiopaque marker(s) in angiography image data;
(iii) the model is one or a combination of the following: a segmentation model, a segmentation model with post-processing, a model with pre-processing, a model with post-processing, a segmentation model with pre-processing, a deep learning or machine learning model, a semantic segmentation model or classification model, an object detection or regression model, an object detection or regression model with pre-processing or post-processing, a combination of a semantic segmentation model and an object detection or regression model, a model using repeated segmentation model technique(s), a model using feature pyramid(s), a model using repeated object detection or regression model technique(s), a deep convolutional neural network model, a recurrent neural network model with long short-term memory that can take temporal relationships across images or frames into account, a model that can take temporal relationships across images or frames into account, a model that can take temporal relationships into account including marker movement(s) or location(s) during pullback in a vessel, a model that can use prior knowledge about the procedure and incorporate the prior knowledge into the machine learning algorithm or loss function, a model using feature pyramid(s) that can take different image resolutions into account, and/or a model using residual learning technique(s);
(iv) the ground truth includes one or more of the following: locations of two endpoints of a major axis of a target marker in each angiography frame, locations of two endpoints of a major axis of a target marker in each angiography frame captured during Optical Coherence Tomography (OCT) pullback, a mask including a line that connects the two endpoint locations with a certain width as a positive area for the segmentation model, all of the markers included in an the acquired or received angiography image data, a centroid of two edge locations, a centroid of two edge locations for the object detection or regression model, and two marker locations in each frame of the acquired or received angiography image data graphically noted or annotated by a user or an expert of the apparatus;
(v) the one or more processors further operate to use one or more neural networks or convolutional neural networks to one or more of: train a model, evaluate a model, determine whether the performance of the trained model is sufficient or not, and/or to detect the marker(s) or radiopaque marker(s), select a model, and estimate the generalization error of the model;
(vi) the method further comprises estimating a generalization error of the trained model with data in the test set or group; and/or
(vii) the method further comprises estimating a generalization error of multiple trained models with data in the test set or group, and selects one model based on its performance on the validation set or group.

10. A method for detecting a marker or a radiopaque marker in angiography image data and/or for performing coregistration using artificial intelligence, the method comprising:
acquiring or receiving angiography image data;
receiving a trained model or loading a trained model from a memory, the trained model being trained using artificial intelligence;
applying the trained model to the acquired or received angiography image data;
selecting one angiography frame of one or more angiography frames of the acquired or received angiography image data after the trained model has been applied;
detecting a marker location on the selected angiography frame with the trained model, the detected marker location defining detected results;
checking whether the marker location is correct or accurate based on the trained model or based on a received or obtained input or inputs;
in an event that the marker location is not correct or accurate, then modifying the detected results or the detected marker location based on the trained model or based on a received or obtained input or inputs, and repeating the check as to whether the marker location is correct or accurate, or in an event that the marker location is correct or accurate, then checking whether all of the angiography frames of the one or more angiography frames have been checked for correctness or accuracy; and in an event that all of the angiography frames have not been checked for correctness or accuracy, then selecting another angiography frame of the one or more angiography frames and repeating the detection of a marker location and the check of whether the marker location is correct or accurate or not for the another angiography frame.

11. The method of claim 10, further comprising one or more of the following:
   (i) in an event that all of the angiography frames have been checked for correctness or accuracy, performing coregistration based on the detected marker location;
   (ii) displaying the detected marker location on a display;
   (iii) displaying the detected marker location on the display such that the detected marker location is overlayed on angiography data;
   (iv) displaying the modified detected results and/or the modified marker location on the display;
   (v) instructing or commanding an intravascular imaging catheter that has a marker or radiopaque marker while inside an object or sample; and/or
   (vi) acquiring or receiving the angiography image data during a pullback operation of an intravascular imaging catheter that has a marker or radiopaque marker where the pullback operation is controlled by one or more processors operating to control the intravascular imaging catheter.

12. The method of claim 10, further including or using one or more of the following:
   (i) an apparatus comprising:
      a memory;
      one or more processors in communication with the memory, the one or more processors operating to:
      acquire or receive angiography image data;
      establish ground truth for at least one or more markers, one or more radiopaque markers, or one or more marker locations in all the acquired angiography image data;
      split the acquired angiography image data into training, validation, and test sets or groups;
      choose one or more hyper-parameter values for model training, the one or more hyper-parameter values including at least one or more of: model architecture, learning rate, and initialization of parameter values;
      train a model with data in the training set or group and evaluate the model with data in the validation set or group;
      determine whether the performance of the trained model is sufficient; and
      in the event that the performance of the trained model is not sufficient, then repeat the procedure of choosing one or more hyper-parameter values, model training and evaluating, and determining, or, in the event that the performance of the trained model is sufficient, select the trained model and save the trained model to the memory;
   (ii) an apparatus comprising:
      one or more processors that operate to:
      acquire or receive angiography image data;
      receive a trained model or load a trained model from a memory, the trained model being trained using artificial intelligence;
      apply the trained model to the acquired or received angiography image data;
      select one angiography frame of one or more angiography frames of the acquired or received angiography image data after the trained model has been applied;
      detect a marker location on the selected angiography frame with the trained model, the detected marker location defining detected results;
      check whether the marker location is correct or accurate based on the trained model or based on an input or inputs received or obtained by the apparatus;
      in an event that the marker location is not correct or accurate, then modify the detected results or the detected marker location based on the trained model or based on an input or inputs received or obtained by the apparatus, and repeat the check as to whether the marker location is correct or accurate, or in an event that the marker location is correct or accurate, then check whether all of the angiography frames of the one or more angiography frames have been checked for correctness or accuracy; and
      in an event that all of the angiography frames have not been checked for correctness or accuracy, then select another angiography frame of the one or more angiography frames and repeat the detection of a marker location and the check of whether the marker location is correct or accurate or not for the another angiography frame;
      additional method steps such that the method further comprises:
      acquiring or receiving angiography image data;
      establishing ground truth for at least one or more markers, one or more radiopaque markers, or one or more marker locations in the acquired angiography image data;
      splitting the acquired angiography image data into training, validation, and test sets or groups;
      choosing one or more hyper-parameter values for model training, the one or more hyper-parameter values including at least one or more of the following: model architecture, learning rate, and initialization of parameter values;
      training a model with data in the training set or group and evaluate the model with data in the validation set or group;
      determining whether the performance of the trained model is sufficient; and
      in the event that the performance of the trained model is not sufficient, then repeating the procedures for choosing one or more hyper-parameter values, model training and evaluating, and determining, or, in the event that the performance of the trained model is sufficient, selecting the trained model and saving the trained model to a memory; or
   (iv) a non-transitory computer-readable storage medium storing at least one program for causing a computer to execute the method, the method further comprising:
      acquiring or receiving angiography image data;
      establishing ground truth for at least one or more markers, one or more radiopaque markers, or one or more marker locations in the acquired angiography image data;
      splitting the acquired angiography image data into training, validation, and test sets or groups;
      choosing one or more hyper-parameters for model training, the one or more hyper-parameters including at least one or more of: model architecture, learning rate, and initialization of parameter values;

training a model with data in the training set or group and evaluate the model with data in the validation set or group;

determining whether the performance of the trained model is sufficient; and in the event that the performance of the trained model is not sufficient, then repeating the procedures for choosing one or more hyper-parameter values, training the model, evaluating the model, and the determining, or, in the event that the performance of the trained model is sufficient, selecting the trained model and saving the trained model to a memory.

13. A non-transitory computer-readable storage medium storing at least one program for causing a computer to execute a method for detecting a marker or a radiopaque marker in angiography image data and/or for performing coregistration, the method comprising:

acquiring or receiving angiography image data;

receiving a trained model or loading a trained model from a memory, the trained model being trained using artificial intelligence;

applying the trained model to the acquired or received angiography image data;

selecting one angiography frame of one or more angiography frames of the acquired or received angiography image data after the trained model has been applied;

detecting a marker location on the selected angiography frame with the trained model, the detected marker location defining detected results;

checking whether the marker location is correct or accurate based on the trained model or based on an input or inputs received or obtained by the apparatus;

in an event that the marker location is not correct or accurate, then modifying the detected results or the detected marker location based on the trained model or based on an input or inputs received or obtained by the apparatus, and repeating the check as to whether the marker location is correct or accurate, or in an event that the marker location is correct or accurate, then checking whether all of the angiography frames of the one or more angiography frames have been checked for correctness or accuracy; and in an event that all of the angiography frames have not been checked for correctness or accuracy, then selecting another angiography frame of the one or more angiography frames and repeating the detection of a marker location and the check of whether the marker location is correct or accurate or not for the another angiography frame.

14. The storage medium of claim 13, wherein the method further comprises one or more of the following:

(i) in an event that all of the angiography frames have been checked for correctness or accuracy, performing coregistration based on the detected marker location;

(ii) displaying the detected marker location on a display;

(iii) displaying the detected marker location on the display such that the detected marker location is overlayed on angiography data;

(iv) displaying the modified detected results and/or the modified marker location on the display;

(v) controlling an intravascular imaging catheter that has a marker or radiopaque marker by inserting the intravascular imaging catheter into an object or sample; and/or (vi) acquiring or receiving the angiography image data during a pullback operation of an intravascular imaging catheter that has a marker or radiopaque marker where the pullback operation is controlled by one or more processors operating to control the intravascular imaging catheter.

* * * * *